United States Patent [19]

Brown

[11] Patent Number: 5,121,337
[45] Date of Patent: Jun. 9, 1992

[54] METHOD FOR CORRECTING SPECTRAL DATA FOR DATA DUE TO THE SPECTRAL MEASUREMENT PROCESS ITSELF AND ESTIMATING UNKNOWN PROPERTY AND/OR COMPOSITION DATA OF A SAMPLE USING SUCH METHOD

[75] Inventor: James M. Brown, Flemington, N.J.

[73] Assignee: Exxon Research and Engineering Company, Florham Park, N.J.

[21] Appl. No.: 597,910

[22] Filed: Oct. 15, 1990

[51] Int. Cl.⁵ .................................... G01N 31/08
[52] U.S. Cl. .......................... 364/498; 364/571.01; 364/571.04; 364/578
[58] Field of Search ............ 364/498, 571.01, 571.02, 364/571.03, 571.04, 571.05, 571.06, 571.07, 571.08, 574, 578

[56] References Cited

U.S. PATENT DOCUMENTS 4,807,148 2/1989 Lacey .................................. 364/498

Primary Examiner—Salvatore Cangialosi
Attorney, Agent, or Firm—Jay Simon

[57] ABSTRACT

For correcting measured spectral data of n samples for data due to the measurement process itself, e.g. due to spectral baseline variations and/or water vapor and carbon dioxide present in the atmosphere of the spectrometer used to make the spectral measurements, the spectral being quantified at f discrete frequencies to produce a matrix X (of dimension f by n) of calibration data, matrix X is orthogonalized with respect to a correction matrix $U_m$ of dimension f by m comprising m quantified correction spectra, at the discrete frequencies f, which simulate data arising from the measurement process itself. The correction method is preferably included in a method of estimating unknown property and/or composition data of a sample under consideration, in which the n samples are calibration samples and a predictive model is developed interrelating known property and composition data of the calibration samples to their spectral data corrected for the data due to the measurement process itself. Then, the unknown property and/or composition data of the example under consideration is estimated from the predictive model on the basis of its measured spectrum.

20 Claims, 31 Drawing Sheets

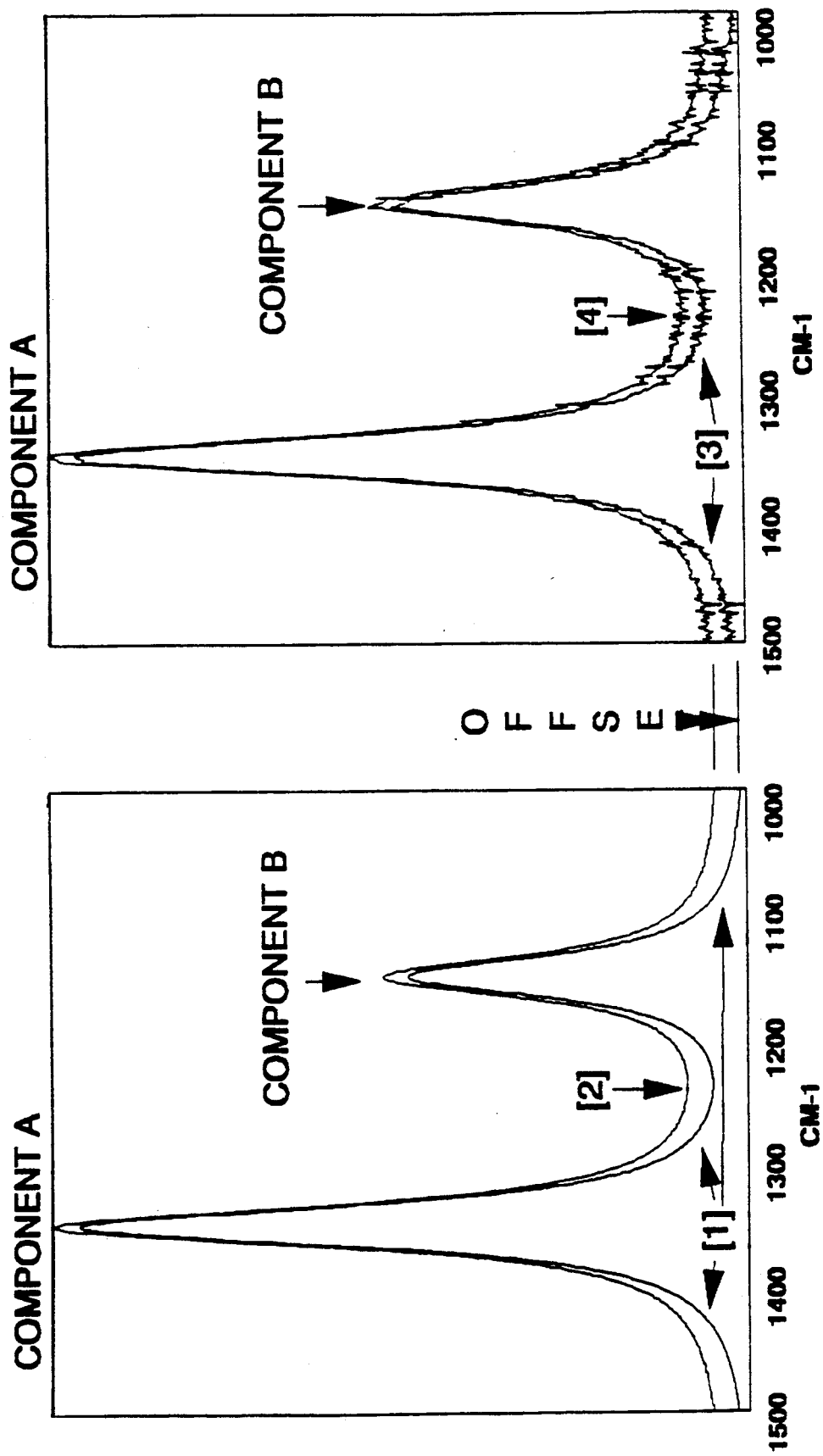

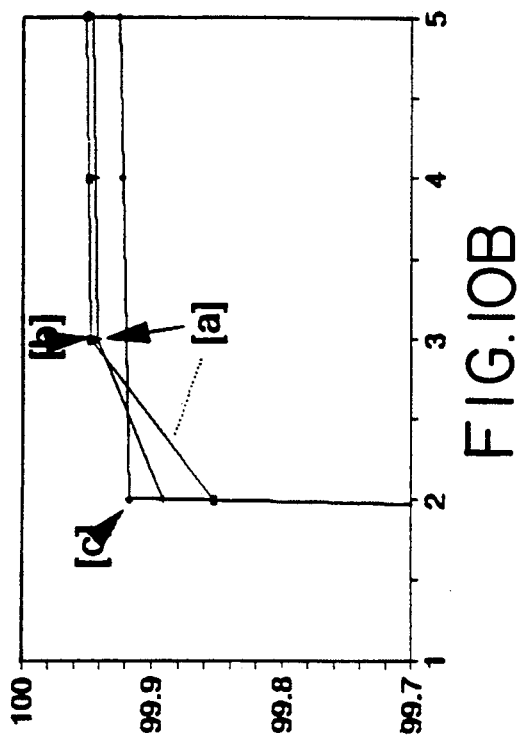
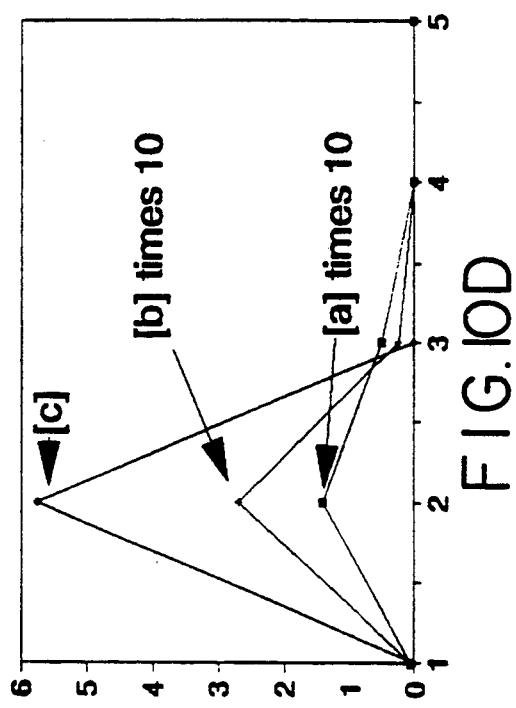
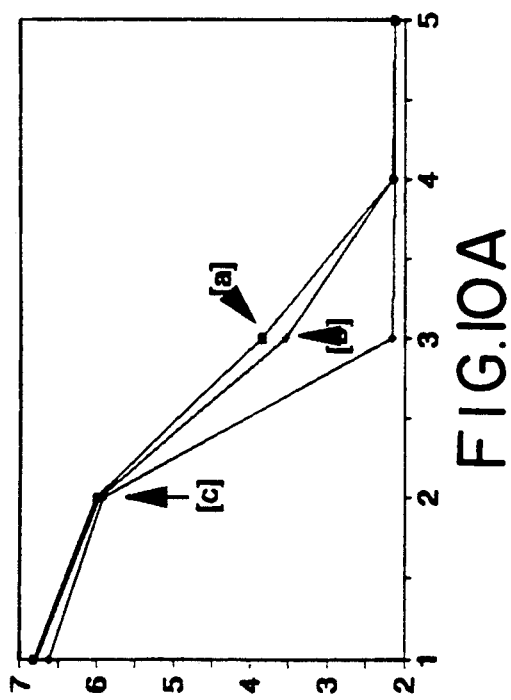
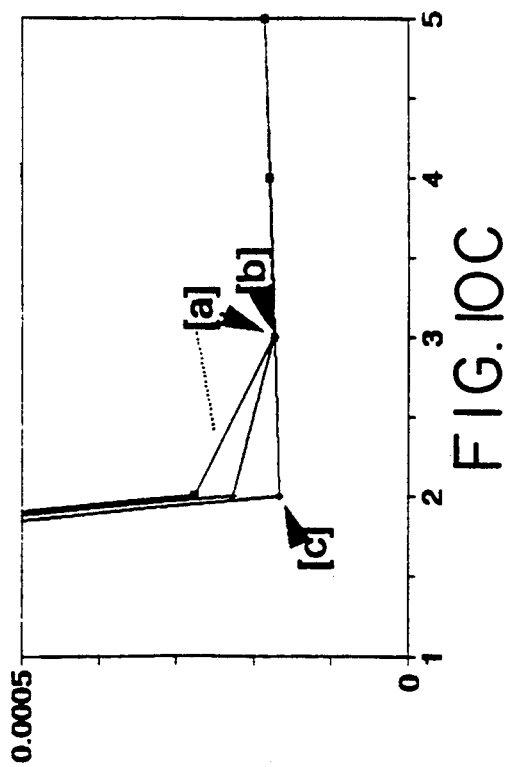

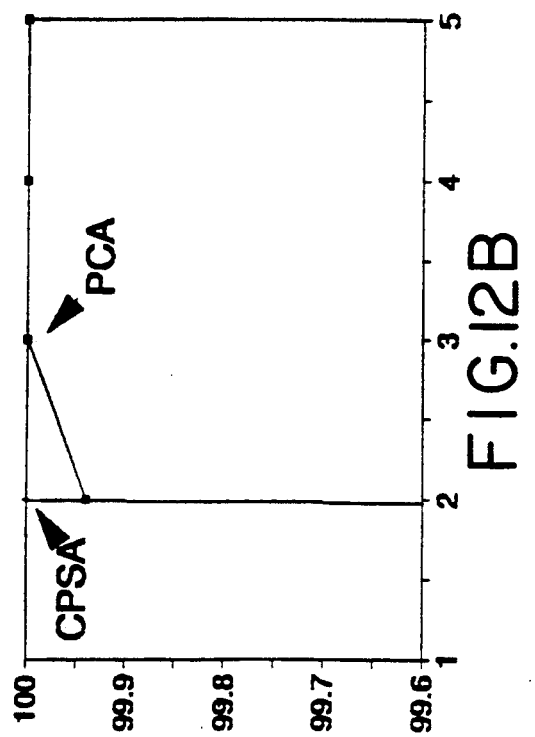
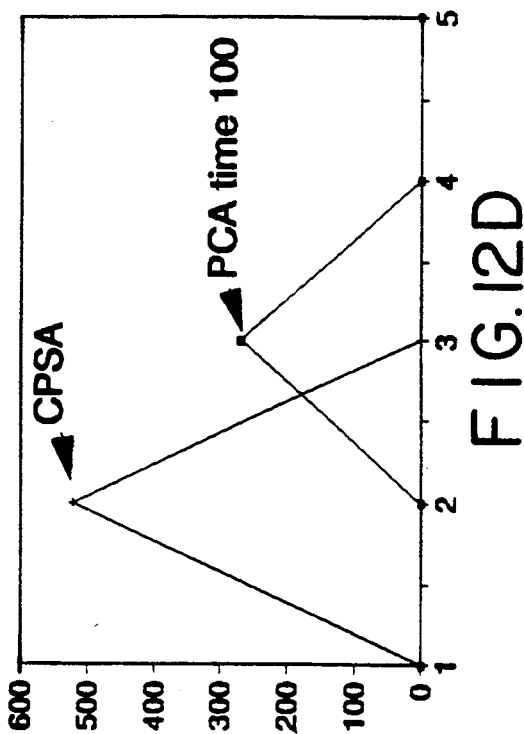
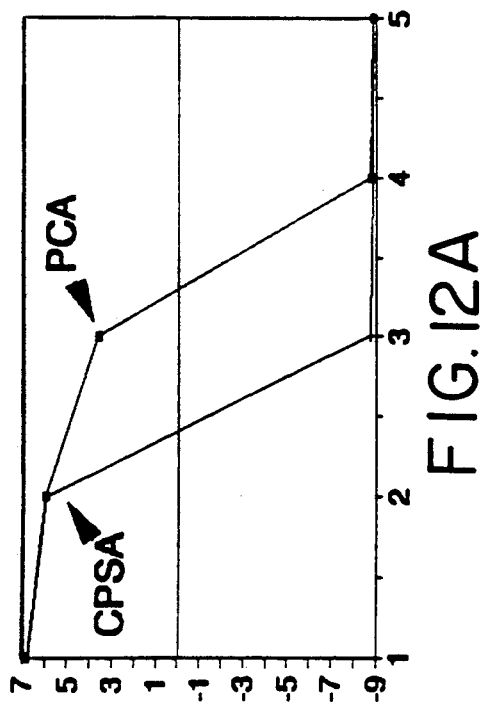
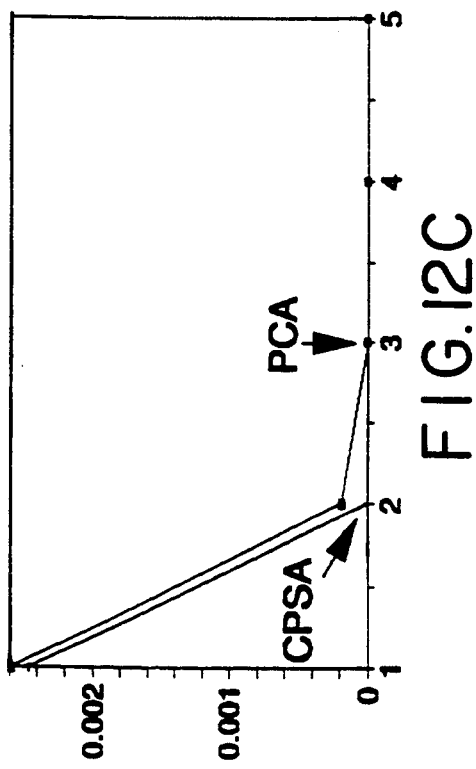

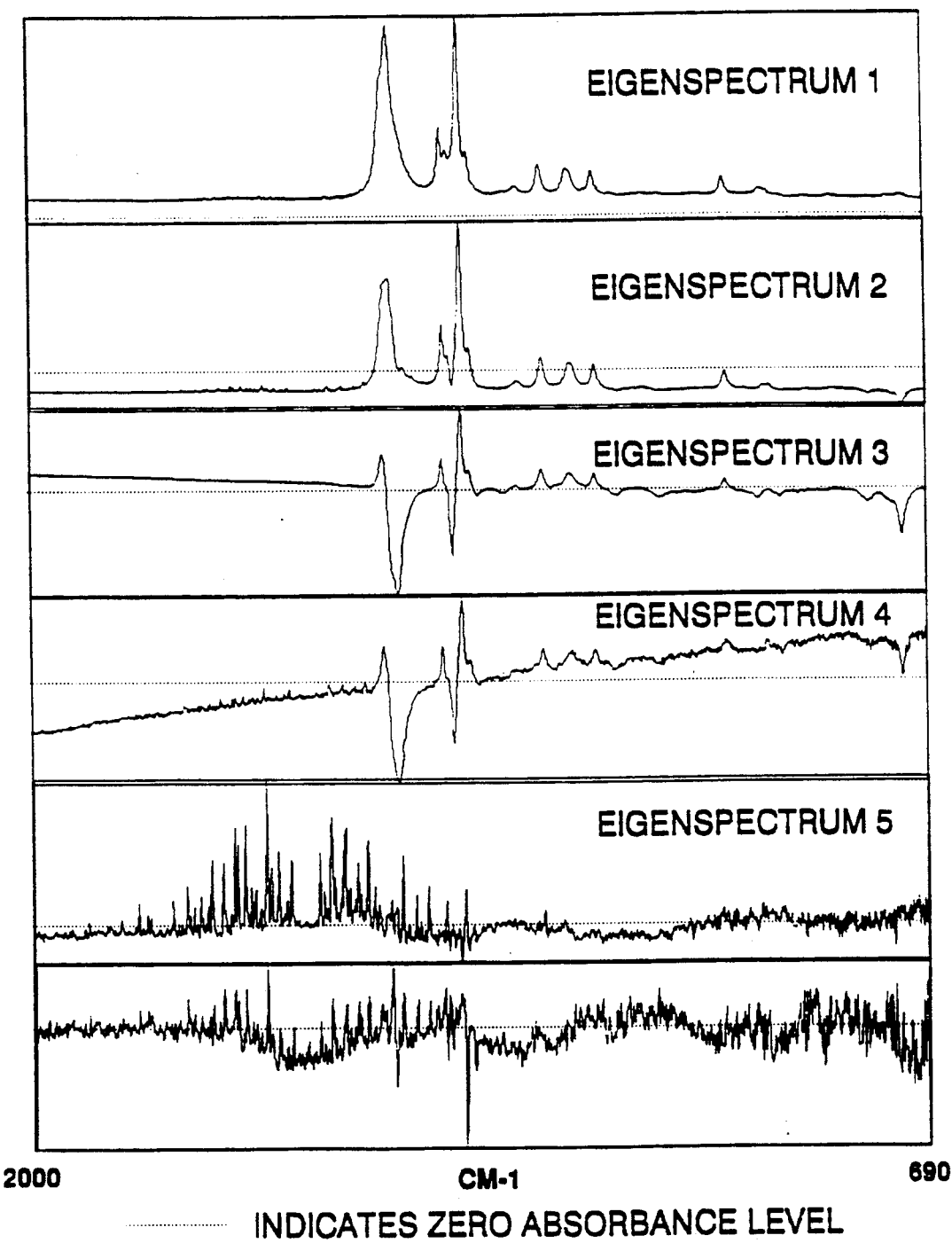

METHOD FOR CORRECTING SPECTRAL DATA FOR DATA DUE TO THE SPECTRAL MEASUREMENT PROCESS ITSELF AND ESTIMATING UNKNOWN PROPERTY AND/OR COMPOSITION DATA OF A SAMPLE USING SUCH METHOD

BACKGROUND OF THE INVENTION

This invention relates, in its broadest aspect, to correcting measured spectral data of a number of samples for the effects of data arising from the measurement process itself (rather than from the sample components). However, it finds particular application to a method of estimating unknown property and/or composition data of a sample, incorporating steps to provide correction for such measurement process spectral data. Examples of property and composition data are chemical composition measurements (such as the concentration of individual chemical components as, for example, benzene, toluene, xylene, or the concentrations of a class of compounds as, for example, paraffin), physical property measurements (such as density, index of refraction, hardness, viscosity, flash point, pour point, vapor pressure), performance property measurement (such as octane number, cetane number, combustibility), and perception (smell/odor, color).

The infrared ($12500-400$ cm$^{-1}$) spectrum of a substance contains absorption features due to the molecular vibrations of the constituent molecules. The absorptions arise from both fundamentals (single quantum transitions occurring in the mid-infrared region from $4000-400$ cm$^{-1}$) and combination bands and overtones (multiple quanta transitions occurring in the mid- and the near-infrared region from $12500-4000$ cm$^{-1}$). The position (frequency or wavelength) of these absorptions contain information as to the types of molecular structures that are present in the material, and the intensity of the absorptions contains information about the amounts of the molecular types that are present. To use the information in the spectra for the purpose of identifying and quantifying either components or properties requires that a calibration be performed to establish the relationship between the absorbances and the component or property that is to be estimated. For complex mixtures, where considerable overlap between the absorptions of individual constituents occurs, such calibrations must be accomplished using multivariate data analysis methods.

In complex mixtures, each constituent generally gives rise to multiple absorption features corresponding to different vibrational motions. The intensities of these absorptions will all vary together in a linear fashion as the concentration of the constituent varies. Such features are said to have intensities which are correlated in the frequency (or wavelength) domain. This correlation allows these absorptions to be mathematically distinguished from random spectral measurement noise which shows no such correlation. The linear algebra computations which separate the correlated absorbance signals from the spectral noise form the basis for techniques such as Principal Components Regression (PCR) and Partial Least Squares (PLS). As is well known, PCR is essentially the analytical mathematical procedure of Principal Components Analysis (PCA), followed by regression analysis. Reference is directed to "An Introduction to Multivariate Calibration and Analysis", Analytical Chemistry Vol. 59, No. 17, September, 1987, pages 1007 to 1017, for an introduction to Multiple Linear Regression (MLR), PCR, and PLS PCR and PLS have been used to estimate elemental and chemical compositions and to a lesser extent physical or thermodynamic properties of solids and liquids based on their mid- or near-infrared spectra. These methods involve: [1] the collection of mid- or near-infrared spectra of a set of representative samples; [2] mathematical treatment of the spectral data to extract the Principal Components or latent variables (e.g. the correlated absorbance signals described above); and [3] regression of these spectral variables against composition and/or property data to build a multivariate model. The analysis of new samples then involves the collection of their spectra, the decomposition of the spectra in terms of the spectral variables, and the application of the regression equation to calculate the composition/properties.

The mathematical/statistical treatment of spectral data using PCR or PLS does not differentiate among possible sources of signals which are correlated in the frequency domain. In particular, PCR and PLS do not differentiate between signals arising from variations in sample components and signals arising from variations in the spectral measurement process. For mid- and near-infrared spectra, common measurement process signals include, but are not limited to, variations in the spectral baseline due to changes in instrument performance or changes in cell window transmittance, and signals due to water vapor and/or carbon dioxide in the spectrometer light path. These measurement process signals can contribute to the Principal Components or latent variables obtained by PCR or PLS, and may be correlated to the composition/property data during the regression. The resultant regression model will then be sensitive to variations in these measurement process variables, and measured compositions or properties can be in error.

In addition to sensitivity to measurement process signals, methods based on PCR or PLS do not correct for variations in the overall scaling of the spectral data. Such scaling variations can result from a variety of factors including variations in cell pathlength due to positioning of the cell in the spectrometer, and expansion or contraction of the cell during use. For situations where the sample flows through the cell during the measurement, variations in flow can also cause variations in the scaling of the spectral data which are equivalent in effect to variations in pathlength. PCR and PLS models require that spectral data be scaled to a specified pathlength prior to analysis, thus requiring that the pathlength be separately measured. The separate measurement of the cell pathlength prior to the use of the cell in collection of the sample spectrum is not convenient or in some cases (e.g. for an on-line flow cell) not possible, nor does such separate measurement necessarily account for the sources of variation mentioned above. Errors in the measured pathlength produce proportional errors in the composition/property data estimated by PCR and PLS models.

SUMMARY OF THE INVENTION

The present invention addresses in particular the problem of how to correct the measured spectral data of the calibration samples so that the data is substantially insensitive to measurement process signals. In general, the invention also seeks to provide a generally improved method which estimates unknown property and/or compositional data of a sample under consideration but which is essentially insensitive to spectral data due to the measurement process itself. It also addresses the problem of scaling variations, referred to in the preceding paragraph.

Therefore, the invention relates, in its broadest aspect, to a method of correcting spectral data of a number of samples for the effects of data arising from the measurement process itself (rather than from the sample components), but it finds particular application to estimating unknown property and/or composition data of a sample where the estimation includes steps to effect the aforesaid correction for the measurement process spectral data. The spectral data for n calibration samples is quantified at f discrete frequencies to produce a matrix X (of dimension f by n) of calibration data. The first step in the method involves producing a correction matrix $U_m$ of dimension f by m comprising m digitised correction spectra at the discrete frequencies f, the correction spectra simulating data arising from the measurement process itself. The other step involves orthoganalizing X with respect to $U_m$ to produce a corrected spectra matrix $X_c$ whose spectra are orthogonal to all the spectra in $U_m$. Due to this orthogonality, the spectra in matrix $X_c$ are statistically independent of spectra arising from the measurement process itself. If (as would normally be the case) the samples are calibration samples used to build a predictive model interrelating known property and composition data of the n samples and their measured spectra so that the model can be used to estimate unknown property and/or composition data of a sample under consideration from its measured spectrum, the estimated property and/or composition data will be unaffected by the measurement process itself. In particular, neither baseline variations nor spectra due for example to water vapor or carbon dioxide vapor in the atmosphere of the spectrometer will introduce any error into the estimates. Although the samples used to produce the spectral data forming the matrix X will usually be calibration samples and the description of the preferred embodiment relates to correcting spectral data of calibration samples for the effects of data arising from the measurement process itself for developing a predictive model, the steps of the data correction method could be used on spectra for a spectral library, with the objective of performing spectral library searching for sample identification using the corrected spectra as reference spectra. It is also remarked that the spectra can be absorption spectra and the preferred embodiments described below all involve measuring absorption spectra. However, this is to be considered as exemplary and not limiting on the scope of the invention as defined by the appended claims, since the method disclosed herein can be applied to other types of spectra such as reflection spectra and scattering spectra (such as Raman scattering). Although the description given herein and with reference to the drawings relate to NIR (near-infrared) and MIR (mid-infrared), nevertheless, it will be understood that the method finds applications in other spectral measurement wavelength ranges including, for example, ultraviolet, visible spectroscopy and Nuclear Magnetic Resonance (NMR) spectroscopy.

Generally, the data arising from the measurement process itself are due to two effects. The first is due to baseline variations in the spectra. The baseline variations arise from a number of causes such as light source temperature variations during the measurement, reflectance, scattering or absorption by the cell windows, and changes in the temperature (and thus the sensitivity) of the instrument detector. These baseline variations generally exhibit spectral features which are broad (correlate over a wide frequency range). The second type of measurement process signal is due to ex-sample chemical compounds present during the measurement process, which give rise to sharper line features in the spectrum. For current applications, this type of correction generally includes absorptions due to water vapor and/or carbon dioxide in the atmosphere in the spectrometer. Absorptions due to hydroxyl groups in optical fibers could also be treated in this fashion. Corrections for contaminants present in the samples can also be made, but generally only in cases where the concentration of the contaminant is sufficiently low as to not significantly dilute the concentrations of the sample components, and where no significant interactions between the contaminant and sample component occurs. It is important to recognize that these corrections are for signals that are not due to components in the sample. In this context, "sample" refers to that material upon which property and/or component concentration measurements are conducted for the purpose of providing data for the model development. By "contaminant", we refer to any material which is physically added to the sample after the property/component measurement but before or during the spectral measurement.

The present inventive method can be applied to correct only for the effect of baseline variations, in which case these variations can be modelled by a set of preferably orthogonal, frequency (or wavelength) dependent polynomials which form the matrix $U_m$ of dimension f by m where m is the order of the polynomials and the columns of $U_m$ are preferably orthogonal polynomials, such as Legendre polynomials. Alternatively the inventive method can be applied to correct only for the effect of ex-sample chemical compounds (e.g. due to the presence in the atmosphere of carbon dioxide and/or water vapor). In this case, the spectra that form the columns of $U_m$ are preferably orthogonal vectors that are representative of the spectral interferences produced by such chemical compounds. It is preferred, however, that both baseline variations and ex-sample chemical compounds are modelled in the manner described to form two correction matrices $U_p$ of dimension f by p and $X_s$, respectively. These matrices are then combined into the single matrix $U_m$, whose columns are the columns of $U_p$ and $X_s$ arranged side-by-side.

In a preferred way of performing the invention, in addition to matrix X of spectral data being orthogonalized relative to the correction matrix $U_m$, the spectra or columns of $U_m$ are all mutually orthogonal. The production of the matrix $U_m$ having mutually orthogonal spectra or columns can be achieved by firstly modelling the baseline variations by a set of orthogonal frequency (or wavelength) dependent polynomials which are computer generated simulations of the baseline variations and form the matrix $U_p$, and then at least one, and usually a plurality, of spectra of ex-sample chemical compounds (e.g. carbon dioxide and water vapor) which are actual spectra collected on the instrument, are supplied to form the matrix $X_s$. Next the columns of $X_s$ are orthogonalized with respect to $U_p$ to form a new matrix $X_s'$. This removes baseline effects from ex-sample chemical compound corrections. Then, the columns of $X_s'$ are orthogonalized with respect to one another to form a new matrix $U_s$, and lastly $U_p$ and $U_s$ are combined to form the correction matrix $U_m$, whose columns are the columns of $U_p$ and $U_s$ arranged side-by-side. It would be possible to change the order of the steps such that firstly the columns of $X_s$ are orthogonalized to form a new matrix of vectors and then the (mutually orthogonal) polynomials forming the matrix $U_p$ are orthogonalized relative to these vectors and then combined with them to form the correction matrix $U_m$. However, this is less preferred because it defeats the advantage of generating the polynomials as being orthogonal in the first place, and it will also mix the baseline variations in with the spectral variations due to ex-sample chemical compounds and make them less useful as diagnostics of instrument performance.

In a real situation, the sample spectral data in the matrix X will include not only spectral data due to the measurement process itself but also data due to noise. Therefore, once the matrix X (dimension f by n) has been orthogonalized with respect to the correction matrix $U_m$ (dimension f by m), the resulting corrected spectral matrix $X_c$ will still contain noise data. This can be removed in the following way. Firstly, a singular value decomposition is performed on matrix $X_c$ in the form $X_c = U\Sigma V^t$, where U is a matrix of dimension f by n and contains the principal component spectra as columns, $\Sigma$ is a diagonal matrix of dimension n by n and contains the singular values, and V is a matrix of dimension n by n and contains the principal component scores, $V^t$ being the transpose of V. In general, the principal components that correspond to noise in the spectral measurements in the original n samples will have singular values which are small in magnitude relative to those due to the wanted spectral data, and can therefore be distinguished from the principal components due to real sample components. Accordingly, the next step in the method involves removing from U, $\Sigma$ and V the k+1 through n principal components that correspond to the noise, to form the new matrices U', $\Sigma'$ and V' of dimensions f by k, k by k and n by k, respectively. When these matrices are multiplied together, the resulting matrix, corresponding with the earlier corrected spectra matrix $X_c$, is free of spectral data due to noise.

For the selection of the number (k) of principal components to keep in the model, a variety of statistical tests suggested in the literature could be used but the following steps have been found to give the best results. Generally, the spectral noise level is known from experience with the instrument. From a visual inspection of the eigenspectra (the columns of matrix U resulting from the singular value decomposition), a trained spectroscopist can generally recognise when the signal levels in the eigenspectra are comparable with the noise level. By visual inspection of the eigenspectra, an approximate number of terms, k, to retain can be selected. Models can then be built with, for example, k−2, k−1, k, k+1, k+2 terms in them and the standard errors and PRESS (Predictive Residual Error Sum of Squares) values are inspected. The smallest number of terms needed to obtain the desired precision in the model or the number of terms that give the minimum PRESS value is then selected. This choice is made by the spectroscopist, and is not automated. A Predicted Residual Error Sum of Squares is calculated by applying a predictive model for the estimation of property and/or component values for a test set of samples which were not used in the calibration but for which the true value of the property or component concentration is known. The difference between the estimated and true values is squared, and summed for all the samples in the test set (the square root of the quotient of the sum of squares and the number of test samples is sometimes calculated to express the PRESS value on a per sample basis). A PRESS value can be calculated using a cross validation procedure in which one or more of the calibration samples are left out of the data matrix during the calibration, and then analyzed with the resultant model, and the procedure is repeated until each sample has been left out once.

The polynomials that are used to model background variations are merely one type of correction spectrum. The difference between the polynomials and the other "correction spectra" modelling ex-sample chemical compounds is twofold. First, the polynomials may conveniently be computer-generated simulations of the background (although this is not essential and they could instead be simple mathematical expressions or even actual spectra of background variations) and can be generated by the computer to be orthogonal. The polynomials may be Legendre polynomials which are used in the actual implementation of the correction method since they save computation time. There is a specific recursion algorithm to generate the Legendre polynomials that is disclosed in the description hereinafter. Generally, each row of the $U_p$ matrix corresponds to a given frequency (or wavelength) in the spectrum. The columns of the $U_p$ matrix will be related to this frequency. The elements of the first column would be a constant, the elements of the second column would depend linearly on the frequency, the elements of the third column would depend on the square of the frequency, etc. The exact relationship is somewhat more complicated than that if the columns are to be orthogonal. The Legendre polynomials are generated to be orthonormal, so that it is not necessary to effect a singular value decomposition or a Gram-Schmidt orthogonalization to make them orthogonal. Alternatively, any set of suitable polynomial terms could be used, which are then orthogonalized using singular value decomposition or a Gram-Schmidt orthogonalization. Alternatively, actual spectra collected on the instrument to simulate background variation can be used and orthogonalized via one of these procedures. The other "correction spectra" are usually actual spectra collected on the instrument to simulate interferences due to ex-sample chemical compounds, e.g. the spectrum of water vapor, the spectrum of carbon dioxide vapor, or the spectrum of the optical fiber of the instrument. Computer generated spectra could be used here if the spectra of water vapor, carbon dioxide, etc. can be simulated. The other difference for the implementation of the correction method is that these "correction spectra" are not orthogonal initially, and therefore it is preferred that they be orthogonalized as part of the procedure. The polynomials and the ex-sample chemical compound "correction spectra" could be combined into one matrix, and orthogonalized in one step to produce the correction vectors. In practice, however, this is not the best procedure, since the results would be sensitive to the scaling of the polynomials relative to the ex-sample chemical compound "correction spectra". If the ex-sample chemical compound "correction spectra" are collected spectra, they will include some noise. If the scaling on the polynomials is too small, the contribution of the noise in these "correction spectra" to the total variance in the correction matrix $U_m$ would be larger than that of the polynomials, and noise vectors would end up being included in the ex-sample chemical compound correction vectors. To avoid this, preferably the polynomials are generated first, the ex-sample chemical compound "correction spectra" are orthogonalized to the polynomials, and then the correction vectors are generated by performing a singular value decomposition (described below) on the orthogonalized "correction spectra".

As indicated above, a preferred way of performing the correction for measurement process spectral data is firstly to generate the orthogonal set of polynomials which model background variations, then to orthoganalize any "correction spectra" due to ex-sample chemical compounds (e.g. carbon dioxide and/or water vapor) to this set to produce a set of "correction vectors", and finally to orthogonalize the resultant "correction vectors" among themselves using singular value decomposition. If multiple examples of "correction spectra", e.g. several spectra of water vapor, are used, the final number of "correction vectors" will be less than the number of initial "correction spectra". The ones eliminated correspond with the measurement noise. Essentially, principal components analysis (PCA) is being performed on the orthogonalized "correction spectra" to separate the real measurement process data being modelled from the random measurement noise.

It is remarked that the columns of the correction matrix $U_m$ do not have to be mutually orthogonal for the correction method to work, as long as the columns of the data matrix X are orthogonalized to those of the correction matrix $U_m$. However, the steps for generating the $U_m$ matrix to have orthogonal columns is performed to simplify the computations required in the orthogonalization of the spectral data X of the samples relative to the correction matrix $U_m$, and to provide a set of statistically independent correction terms that can be used to monitor the measurement process. By initially orthogonalizing the correction spectra $X_s$ due to ex-sample chemical compounds to $U_p$ which models background variations, any background contribution to the resulting correction spectra is removed prior to the orthogonalization of these correction spectra among themselves. This procedure effectively achieves a separation of the effects of background variations from those of ex-sample chemical compound variations, allowing these corrections to be used as quality control features in monitoring the performance of an instrument during the measurement of spectra of unknown materials, as will be discussed hereinbelow.

When applying the technique for correcting for the effects of measurement process spectral data in the development of a method of estimating unknown property and/or composition data of a sample under consideration, the following steps are performed. Firstly, respective spectra of n calibration samples are collected, the spectra being quantified at f discrete frequencies (or wavelengths) and forming a matrix X of dimension f by n. Then, in the manner described above, a correction matrix $U_m$ of dimension f by m is produced. This matrix comprises m digitised correction spectra at the discrete frequencies f, the correction spectra simulating data arising from the measurement process itself. The next step is to orthogonalize X with respect to $U_m$ to produce a corrected spectra matrix $X_c$ whose spectra are each orthogonal to all the spectra in $U_m$. The method further requires that c property and/or composition data are collected for each of the n calibration samples to form a matrix Y of dimension n by c ($c \geq 1$). Then, a predictive model is determined correlating the elements of matrix Y to matrix $X_c$. Different predictive models can be used, as will be explained below. The property and/or composition estimating method further requires measuring the spectrum of the sample under consideration at the f discrete frequencies to form a matrix of dimension f by 1. The unknown property and/or composition data of the samples is then estimated from its measured spectrum using the predictive model. Generally, each property and/or component is treated separately for building models and produces a separate f by 1 prediction vector. The prediction is just the dot product of the unknown spectrum and the prediction vector. By combining all the prediction vectors into a matrix P of dimension f by c, the prediction involves multiplying the spectrum matrix (a vector of dimension f can be considered as a 1 by f matrix) by the prediction matrix to produce a 1 by c vector of predictions for the c properties and components.

As mentioned in the preceding paragraph, various forms of predictive model are possible. The predictive model can be determined from a mathematical solution to the equation $Y = X_c^t P + E$, where $X_c^t$ is the transpose of the corrected spectra matrix $X_c$, P is the predictive matrix of dimension f by c, and E is a matrix of residual errors from the model and is of dimension n by c. The validity of the equation $Y = X_c^t P + E$ follows from the inverse statement of Beer's law, which itself can be expressed in the form that the radiation-absorbance of a sample is proportional to the optical pathlength through the sample and the concentration of the radiation-absorbing species in that sample. Then, for determining the vector $y_u$ of dimension 1 by c containing the estimates of the c property and/or composition data for the sample under consideration, the spectrum $x_u$ of the sample under consideration, $x_u$ being of dimension f by 1, is measured and $y_u$ is determined from the relationship $y_u = x_u^t P$, $x_u^t$ being the transpose of matrix $x_u$.

Although, in a preferred implementation of this invention, the equation $Y = X_c^t P + E$ is solved to determine the predictive model, the invention could also be used in developing models where the equation is represented (by essentially the statement of Beer's law) as $X_c = AY^t + E$, where A is an f by c matrix. In this case, the matrix A would first be estimated as $A = X_c Y(Y^t Y)^{-1}$. The estimation of the vector $y_u$ of dimension 1 by c containing the c property and/or composition data for the sample under consideration from the spectrum $x_u$ of the sample under consideration would then involve using the relationship $y_u = x_u A(A^t A)^{-1}$. This calculation, which is a constrained form of the K-matrix method, is more restricted in application, since the required inversion of $Y^t Y$ requires that Y contain concentration values for all sample components, and not contain property data.

The mathematical solution to the equation $Y = X_c^t P + E$ (or $X_c = AY^t + E$) can be obtained by any one of a number of mathematical techniques which are known per se, such as linear least squares regression, sometimes otherwise known as multiple linear regression (MLR), principal components analysis/regression (PCA/PCR) and partial least squares (PLS). As mentioned above, an introduction to these mathematical techniques is given in "An Introduction to Multivariate Calibration and Analysis", Analytical Chemistry, Vol. 59, No. 17, Sep. 1, 1987, Pages 1007 to 1017.

The purpose of generating correction matrix $U_m$ and in orthogonalizing the spectral data matrix X to $U_m$ is twofold: Firstly, predictive models based on the resultant corrected data matrix $X_c$ are insensitive to the effects of background variations and ex-sample chemical components modeled in $U_m$, as explained above. Secondly, the dot (scalar) products generated between the columns of $U_m$ and those of X contain information about the magnitude of the background and ex-sample chemical component interferences that are present in the calibration spectra, and as such, provide a measure of the range of values for the magnitude of these interferences that were present during the collection of the calibration spectral data. During the analysis of a spectrum of a material having unknown properties and/or composition, similar dot products can be formed between the unknown spectrum, $x_u$, and the columns of $U_m$, and these values can be compared with those obtained during the calibration as a means of checking that the measurement process has not changed significantly between the time the calibration is accomplished and the time the productive model is applied for the estimation of properties and components for the sample under test. These dot products thus provide a means of performing a quality control assessment on the measurement process.

The dot products of the columns of $U_m$ with those of the spectral data matrix X contain information about the degree to which the measurement process data contribute to the individual calibration spectra. This information is generally mixed with information about the calibration sample components. For example, the dot product of a constant vector (a first order polynomial) with a spectrum, will contain information about the total spectral integral, which is the sum of the integral of the sample absorptions, and the integral of the background. The information about calibration sample components is, however, also contained in the eigenspectra produced by the singular value decomposition of $X_c$. It is therefore possible to remove that portion of the information which is correlated to the sample components from the dot products so as to recover values that are uncorrelated to the sample components, i.e. values that represent the true magnitude of the contributions of the measurement process signals to the calibration spectra. This is accomplished by the following steps:

(1) A matrix $V_m$ of dimension n by m is formed as the product of $X^tU_m$, the individual elements of $V_m$ being the dot products of the columns of X with those of $U_m$;

(2) The corrected data matrix $X_c$ is formed, and its singular value decomposition is computed as $U\Sigma V^t$;

(3) A regression of the form $V_m = VZ + R$ is calculated to establish the correlation between the dot products and the scores of the principal components: VZ represents the portion of the dot products which is correlated to the sample components and the regression residuals R represent the portion of the dot products that are uncorrelated to the sample components, which are in fact the measurement process signals for the calibration samples;

(4) In the analysis of a sample under test, the dot products of the unknown spectrum with each of the correction spectra (columns of $U_m$) are calculated to form a vector $v_m$, the corrected spectrum $x_c$ is calculated, the scores for the corrected spectrum are calculated as $v = x_c^t U\Sigma^{-1}$, and the uncorrelated measurement process signal values are calculated as $r = v_m - vZ$. The magnitude of these values is then compared to the range of values in R as a means of comparing the measurement process during the analysis of the unknown to that during the calibration.

It will be appreciated that the performance of the above disclosed correction method and method of estimating the unknown property and/or composition data of the sample under consideration involves extensive mathematical computations to be performed. In practice, such computations would be made by computer means comprising a computer or computers, which would be connected to the instrument in a measurement mode so as to receive the measured output spectrum of the calibration sample, ex-sample chemical compound or test sample. In a correction mode in conjunction with the operator, the computer means stores the calibration spectra to form the matrix X, calculates the correction matrix $U_m$, and orthogonalizes X with respect to the correction matrix $U_m$. In addition, the computers means operates in a storing mode to store the c known property and/or composition data for the n calibration samples to form the matrix Y of dimension n by c ($c \geq 1$). In a mode building mode, the computer means determines, in conjunction with the operator, a predictive model correlating the elements of matrix Y to those of matrix $X_c$. Lastly, the computer means is arranged to operate in a prediction mode in which it estimates the unknown property and/or compositional data of the sample under consideration from its measured spectrum using the determined predictive model correlating the elements of matrix Y to those of matrix $X_c$.

In more detail, the steps involved according to a preferred way of making a prediction of property and/or composition data of a sample under consideration can be set out as follows. Firstly, a selection of samples for the calibrating is made by the operator or a laboratory technician. Then, in either order, the spectra and properties/composition of these samples need to be measured, collected and stored in the computer means by the operator and/or laboratory technician, together with spectra of ex-sample chemical compounds to be used as corrections. In addition, the operator selects the computer-generated polynomial correction used to model baseline variations. The computer means generates the correction matrix $U_m$ and then orthogonalizes the calibration sample spectra (matrix X) to produce the corrected spectra matrix $X_c$ and, if PCR is used, performs the singular value decomposition on matrix $X_c$. The operator has to select (in PCR) how many of the principal components to retain as correlated data and how many to discard as representative of (uncorrelated) noise. Alternatively, if the PLS technique is employed, the operator has to select the number of latent variables to use. If MLR is used to determine the correlation between the corrected spectra matrix $X_c$ and the measured property and/or composition data Y, then a selection of frequencies needs to be made such that the number of frequencies at which the measured spectra are quantised is less than the number of calibration samples. Whichever technique is used to determine the correlation (i.e. the predictive model) interrelating $X_c$ and Y, having completed the calibration, the laboratory technician measures the spectrum of the sample under consideration which is used by the computer means to compute predicted property and/or composition data based on the predictive model.

These and other features and advantages of the invention will now be described, by way of example, with reference to the drawings.

BRIEF DESCRIPTION OF THE DRAWINGS

FIG. 1 is a plot of benzene wt% by infrared (abscissa) v. benzene wt% by gas chromatography;

FIG. 2 is a plot of API gravity by MID-IR (abscissa) v. API gravity by ASTM D-1298;

FIG. 3 is a plot of cetane number by NIR (abscissa) v. cetane number by ASTM D-613;

FIG. 4 is a plot of wt% hydrogen by MID-IR (abscissa) v. wt% hydrogen by NMR;

FIG. 5 is a plot of wt% ZDDP by MID-IR (abscissa) v. wt% ZDDP as prepared;

FIGS. 6A to 10D illustrate various spectra and statistics relating to binary system with variable offset; more specifically, FIGS. 6A and 6B are spectra from data sets [B-[4] for example 1, spectra for 1, spectra for 50/50 A/B samples;

FIGS. 10A-10D are statistics for analysis of data set [4], the abscissa and ordinate for each of 10A, 10B, 10C, and 10D being the same as for FIG. 7;

FIGS. 11 and 12D illustrate various spectra and statistics relating to removal of a sharp-lined, overlapping spectral interference; more specifically FIGS. 12A-12D are statistics for data including spectral interference, the abscissa and ordinate for FIGS. 12A, 12B, 12C and 12D being the same as for FIG. 7;

FIGS. 13A to 17 show various graphical depictions and spectra relating to binary blends of isooctane and heptane; more specifically, FIGS. 13A-13D are statistics for isooctane/heptane binary system the abscissa and ordinate for FIGS. 13A, 13B, 13C, and 13D being the same as for FIG. 7;

FIG. 14 are average (14A) and standard (14B) deviation spectra for isooctane/heptane blends;

FIG. 15 is the eigenspectra for PCA analysis of heptane/octane blends;

FIG. 16 is the eigenspectra for CPSA analysis of heptane/isooctane blends;

FIG. 17 is the comparison of the effect of frequency dependent background variation of PCA and CPSA isooctane predictions; the abscissa being predicted isooctane content (vol%);

FIGS. 18 to 24 show various graphical depictions and eigenspectra relating to the analysis of a 5-component additive package and to a comparison with the K Matrix Method; more specifically, FIG. 18 is the average and standard deviation spectra for five component add pack blends;

FIG. 20 is the eigen spectra for PCA analysis of five component add pack;

FIG. 21 is the eigen spectra for PCA analysis of five component add pack;

FIG. 22 is the eigen spectra for PCA analysis of five component add pack and cyclohexane;

FIG. 23 is the eigen spectra for CPSA analysis of five component add pack and cyclohexane;

FIG. 24 is the eigen spectra for CPSA analysis of five component add pack and cyclohexane;

FIG. 25 shows the constrained principal components model for research octane number of Powerformates: initial model without water vapor correction, where the abscissa is NIR estimated research octane number plotted against time on line;

FIG. 26 is shows the initial Powerformate spectrum minus spectrum at indicated time, where the abscissa is adsorbance plotted against wavelength in nanometers;

FIG. 27 shows NIR Powerformate spectrum (top) and NIR water vapor spectrum (bottom) plotted against wavelength in nanometers;

FIG. 28 shows the constrained principal components model for research octane number of Powerformates: final model with water vapor correction, where the abscissa is NIR estimated research octane number plotted against time on line.

FIG. 29 shows an example of measurement process quality control of water vapor correction for isooctane/heptane spectra, where the absissa is DOT product with water correction spectrum;

FIG. 30 shows an example of measurement process quality control of chloroform correction for add pack spectra, where the abscissa is DOT product with chloroform correction spectrum.

Figure 1:
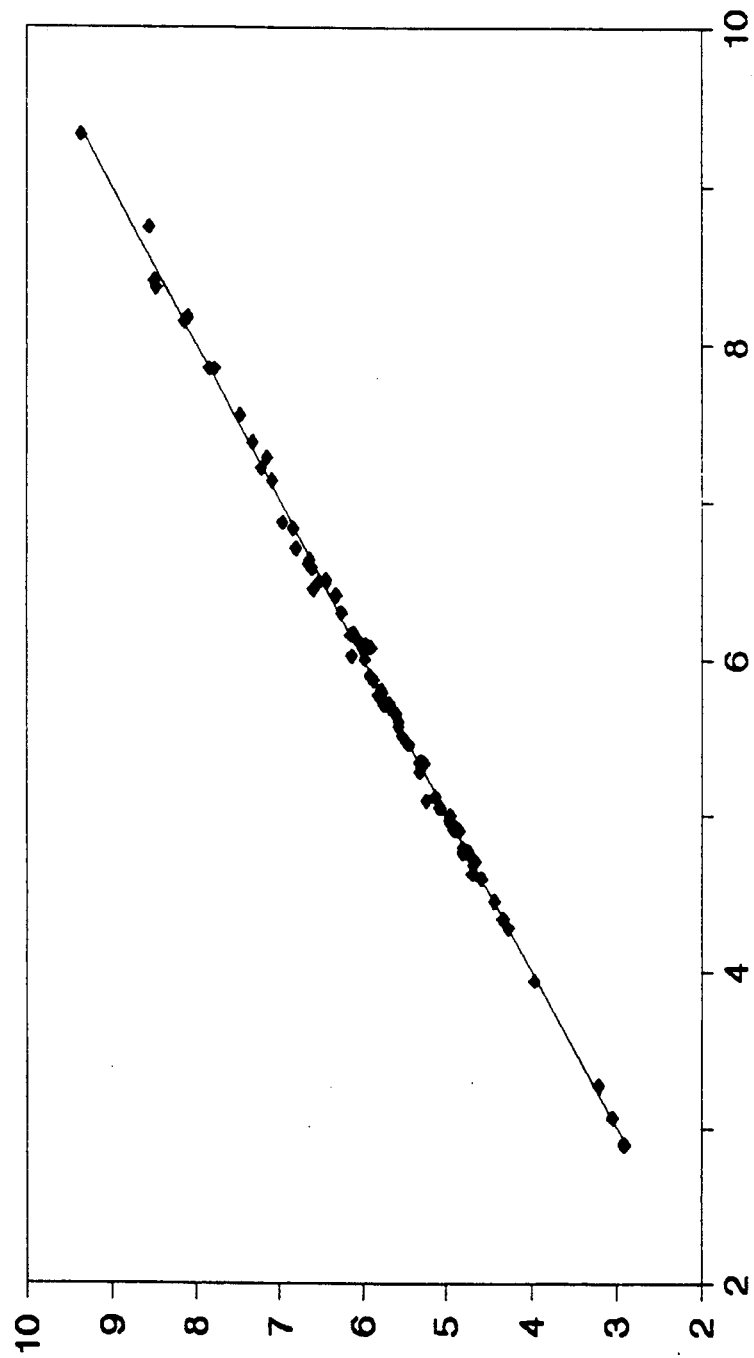
FIGS. 1 to 5 are scattergrams of different property and composition data when determined by conventional techniques plotted against the same data determined by the spectroscopic method disclosed herein; more specifically.

An algorithm, termed The Constrained Principal Spectra Analysis (CPSA), is described hereinbelow, and it's application to multivariate, spectral analysis is demonstrated. CPSA is a novel modification of Principal Components Analysis (PCA) which allows the spectroscopist to input his knowledge of the spectral measurement process into the development of spectral based multivariate models so as to maximize the stability and robustness of these models for the subsequent measurement of property and composition data for unknowns. CPSA allows signals in the calibration spectra which are due to the spectral measurement process rather than the sample components to be modeled such that the resultant predictive models can be constrained to be insensitive to these measurement process signals. The measurement process variables for which constraints are developed also server as quality control variables for monitoring the status of the measurement process during the subsequent application of the model for measurement of unknowns.

A corresponding modification can also be made to the PLS and MLR techniques, which, as explained above, are alternatives to PCA (or PCR). The respective modifications will be referred to herein as Constrained Partial Least Squares (CPLS), and Constrained Multiple Linear Regression (CMLS). Generically, CPSA, CPLS and CMLR will be referred to as Constrained Spectral Analysis (CSA).

The mid- and near-infrared spectra of a molecule consist of numerous absorption bands corresponding to different types of molecular vibrations. In a complex mixture, the absorptions due to a specific molecular type will all vary together in intensity as the concentration of the species changes. The fact that the intensities of these multiple absorptions are correlated in the frequency (wavelength) domain allows them to be distinguished for random noise that is uncorrelated in the frequency domain. Multivariate data analysis methods such as Principal Components Analysis or Partial Least Squares are used to identify and isolate the frequency correlated signals among a series of calibration spectra. These spectral variables can be regressed against properties and component concentration data for the calibration samples to develop a predictive model. During the analysis of unknowns, the spectra are decomposed in terms of these same spectral variables, and regression relationships are used to predict the property/composition of the new samples.

In all real spectral measurements, the variation in sample component concentrations is generally not the only source of frequency correlated signal. Signals arising from the measurement process (e.g. the instrument, the cell, etc.) are superimposed on the absorptions due to the sample components. To the mathematics, these measurement process signals are indistinguishable from the sample component absorptions, and are thus extracted as spectral variables. If these measurement process variables are correlated to the property/concentration (or errors in these values) during the regression, predictions based on the resultant model will be dependent on variations in the measurement process. CPSA allows the spectroscopist to model potential sources of measurement process signals and remove them as spectral variables prior to the regression. The resultant predictive models are constrained to be insensitive to the measurement process signals, and are thus more stable and robust to variations in the spectral data collection.

Examples included in this report demonstrate the use of CPSA for developing predictive models, and compare the CPSA results to those obtained via other multivariate methods.

INTRODUCTION

Principal Components Regression and Partial Least Squares multivariate data analyses are used to correlate the molecular information inherent to spectral data to property and compositional variables. Both PCR and PLS are most often applied to under-determined calibrations, i.e. to calibrations where the number of data points per spectrum exceeds the number of calibration samples. Therefore, both methods require a variable reduction which reduces the dimensionality of the spectral data. While the algorithms used to extract the Principal Components and PLS latent variables differ in computational methodology, both are based on an assumption that there are only two sources of variance in the spectral data. Real components are assumed to give rise to multiple signals whose intensities are linearly correlated in the frequency (or wavelength) domain. Random spectral noise is assumed to be uncorrelated in the frequency domain. The algorithms are designed to isolate the signals that are correlated from the random noise so as to produce spectral variables that can be regressed against concentration and/or property data to produce a predictive model. If the signals due to sample components were the only source of frequency correlated signal in the spectral data, both computational methods would yield stable, robust predictive models which could be used for the subsequent analysis of unknown materials. Unfortunately, in all real spectral measurements, there are additional sources of signals whose intensities are linearly correlated in the frequency domain, which contribute to the total spectral variance, and which are associated with the measurement process rather than the samples. For mid-infrared spectroscopy, examples of the measurement process signals would include reflectance/scattering loses from cell windows, and spectral interferences due to trace water and carbon dioxide in the spectrometer purge gas. If these measurement related signals were constant, they would have no effect on the predictive models. However, since these measurement process signals are themselves subject to variation among real spectra, they are, to the mathematics, indistinguishable from the sample component signals, they can be extracted along with the sample component variations during the variable reduction, and they may be correlated to the properties or component concentrations (or to errors in these dependent values) in the generation of the predictive model. The resultant model will then not be stable and robust with respect to changes in the measurement process related signals.

Spectral preprocessing is used to minimize the effect of measurement related variance on multivariate models. Baseline correction algorithms are an example of commonly employed preprocessing. Data points at which minimal sample component intensity is expected are selected and fit to a "baseline function" (a constant offset, or frequency dependent polynomial). The "baseline" is subtracted from the spectrum prior to the multivariate calibration or analysis. Spectral subtraction algorithms are also be employed in preprocessing, for the removal of some types of spectral interferences (e.g. water vapor). The objective of the preprocessing is to remove the measurement process related signals from the spectral data prior to the variable reduction. There are several disadvantages to the preprocessing methods that are typically employed for spectral analysis.

(1) The calculations used in preprocessing the spectral data are generally based on a selected subset of the spectral data (e.g. a single point offset correction, or a two point linear baseline correction), and are sensitive to the noise characteristics of the points used for the correction. Depending on the relative magnitudes of the noise and the signal being removed, the preprocessing may be ineffective in removing the measurement process signals, or may only substitute one source of variation (correlated to the spectral noise) for another (the signal being subtracted).

(2) For some types of signals (e.g. spectral interferences which are not well resolved from sample signals, or higher order background terms), effective, reproducible preprocessing algorithms are difficult to develop.

(3) The spectral variables which are removed by the preprocessing step are not orthogonal to the variables (Principal Components) defined by the multivariate analysis. The lack of orthogonality makes it difficult to statistically define the effects of the preprocessing on the resultant model.

(4) Since by definition, the preprocessing is applied before the multivariate analysis, the preprocessing algorithms are not generally included as an integral part of most multivariate programs. The user is thus left with the job of developing and implementing his own preprocessing algorithms and integrating them with the multivariate analysis programs. Since different algorithms can be required to handle different types of measurement process signals, and since the variables that are removed by each algorithm are not orthogonal, the ultimate effect of the preprocessing on the stability and robustness of the predictive model become increasingly difficult to determine.

The purpose of this description is to describe an algorithm which is designed to incorporate preprocessing as an integral part of the multivariate analysis. The Constrained Principal Spectra Analysis (CPSA) algorithm allows the user to model (e.g. provide an example spectrum of) potential sources of measurement related signals. The algorithm generates a set of orthonormal correction variables (spectra) which are removed from the spectral data prior to the multivariate variable reduction. The multivariate predictive model generated in this manner is constrained so as to be insensitive (or-thogonal) to the presence of these measurement process signals in the spectral data. Since the algorithm uses the entire spectral range in generating the constraints, it is relatively insensitive to spectral noise. The algorithm can correct for polynomial backgrounds as well as poorly resolved spectral interferences. Since the "preprocessing" is an integral part of the algorithm, the effects of including corrections on the resultant predictive model can be readily tested. Finally, the correction variables defined by the CPSA algorithm serve a useful quality control variables for monitoring the measurement process during analysis of unknowns.

Although the Constraint algorithm described here is specifically applied as a variation of a Principal Components Analysis, the same methodology could be used to develop a constrained version of the Partial Least Squares analysis.

MATHEMATICAL BASIS FOR CPSA

The object of Principal Components Analysis (PCA) is to isolate the true number of independent variables in the spectral data so as to allow for a regression of these variables against the dependent property/composition variables. The spectral data matrix, X, contains the spectra of the n samples to be used in the calibration as columns of length f, where f is the number of data points (frequencies or wavelengths) per spectrum. The object of PCA is to decompose the f by n X matrix into the product of several matrices. This decomposition can be accomplished via a Singular Value Decomposition:

$$X = U\Sigma V^t \quad (1)$$

where U (the left eigenvector matrix) is of dimension f by n, $\Sigma$ (the diagonal matrix containing the singular values $\sigma$) is of dimension n by n, and $V^t$ is the transpose of V (the right eigenvector matrix) which is of dimension n by n. Since some versions of PCA perform the Singular Value Decomposition on the transpose of the data matrix, $X^t$, and decompose it as $V\Sigma U^t$, the use of the terms left and right eigenvectors is somewhat arbitrary. To avoid confusion, U will be referred to as the eigenspectrum matrix since the individual column-vectors of U (the eigenspectra) are of the same length, f, as the original calibration spectra. The term eigenvectors will only be used to refer to the V matrix. The matrices in the singular value decomposition have the following properties:

$$U^t U = I_n \quad (2)$$

$$VV^t = V^t V = I_n \quad (3)$$

$$X^t X = V\Lambda V^t \text{ and } XX^t = U\Lambda U^t \quad (4)$$

where $I_n$ is the n by n identify matrix, and $\Lambda$ is the matrix containing the eigenvalues, $\lambda$ (the squares of the singular values), on the diagonal and zeros off the diagonal. Note that the product $UU^t$ does not yield an identify matrix for n less than f. Equations 2 and 3 imply that both the eigenspectra and eigenvectors are orthonormal. In some version of PCA, the U and $\Sigma$ are matrices are combined into a single matrix. In this case, the eigenspectra are orthogonal but are normalized to the singular values.

The object of the variable reduction is to provide a set of independent variables (the Principal Components) against which the dependent variables (the properties or compositions) can be regressed. The basic regression equation for direct calibration is $$Y = X^t P \quad (5)$$

where Y is the n by c matrix containing the property/-composition data for the n samples and c properties/-components, and P is the f by c matrix of regression coefficients which relate the property/composition data to the spectral data. We will refer to the c columns of P as prediction vectors, since during the analysis of a spectrum x (dimension f by 1), the prediction of the properties/components (y of dimension 1 by c) for the sample is obtained by $$y = x^t P \quad (6)$$

Note that for a single property/component, the prediction is obtained as the dot product of the spectrum of the unknown and the prediction vector. The solution to equation 5 is $$[X^t]^{-1} Y = [X^t]^{-1} X^t P = P \quad (7)$$

where $[X^t]^{-1}$ is the inverse of the $X^t$ matrix. The matrix $X^t$ is of course non-square and rank deficient (f>n), and cannot be directly inverted. Using the singular value decompositions, however, the inverse can be approximated as $$[X^t]^{-1} = U\Sigma^{-1} V^t \quad (8)$$

where $\Sigma^{-1}$ is the inverse of the square singular value matrix and contains $1/\sigma$ on the diagonal. Using equations 7 and 8, the prediction vector matrix becomes $$P = U\Sigma^{-1} V^t Y \quad (9)$$

As was noted previously, the objective of the PCA is to separate systematic (frequency correlated) signal from random noise. The eigenspectra corresponding to the larger singular values represent the systematic signal, while those corresponding to the smaller singular values represent the noise. In general, in developing a stable model, these noise components will be eliminated from the analysis before the prediction vectors are calculated. If the first $k<n$ eigenspectra are retained, the matrices in equation 1 become U' (dimension f by k), $\Sigma'$ (dimension k by k) and V' (dimension n by k).

$$X = U'\Sigma'V'^t + E \tag{10}$$

where E is an f by n error matrix. Ideally, if all the variations in the data due to sample components are accounted for in the first k eigenspectra, E contains only random noise. It should be noted that the product $V'V'^t$ no longer yields an identity matrix. To simplify notation the ' will be dropped, and U, $\Sigma$ and V will henceforth refer to the rank reduced matrices. The choice of k, the number of eigenspectra to be used in the calibration, is based on statistical tests and some prior knowledge of the spectral noise level.

Although the prediction of a property/component requires only a single prediction vector, the calculation of uncertainties on the prediction require the full rank reduced V matrix. In practice, a two step, indirect calibration method is employed in which the singular value decomposition of the X matrix is calculated (equation 1), and then the properties/compositions are separately regressed against the eigenvectors $$Y = VB + E \tag{11}$$

$$B = V^t Y \tag{12}$$

During the analysis, the eigenvector for the unknown spectrum is obtained $$v = x^t U \Sigma^{-1} \tag{13}$$

and the predictions are made as $$y = vB \tag{14}$$

The indirect method is mathematically equivalent to the direct method of equation 10, but readily provides the values needed for estimating uncertainties on the prediction.

Equation 6 shows how the prediction vector, P, is used in the analysis of an unknown spectrum. We assume that the unknown spectrum can be separated as the sum of two terms, the spectrum due to the components in the unknown, $x_c$, and the measurement process related signals for which we want to develop constraints, $x_s$. The prediction then becomes $$y = x^t P = x_c^t P + x_s^t P \tag{15}$$

If the prediction is to be insensitive to the measurement process signals, the second term in equation 15 must be zero. This implies that the prediction vector must be orthogonal to the measurement process signal spectra. From equation 10, the prediction vector is a linear combination of the eigenspectra, which in turn are themselves linear combination of the original calibration spectra ($U = XV\Sigma^{-1}$). If the original calibration spectra are all orthogonalized to a specific measurement process signal, the resulting prediction vector will also be orthogonal, and the prediction will be insensitive to the measurement process signal. This orthogonalization procedure serves as the basis for the Constrained Principal Spectra Analysis algorithm.

In the Constrained Principal Spectra Analysis (CPSA) program, two types of measurement process signals are considered. The program internally generates a set of orthonormal, frequency dependent polynomials, $U_p$. $U_p$ is a matrix of dimension f by p where p is the maximum order (degree minum one) of the polynomials, and it contains columns which are orthonormal Legendre polynomials defined over the spectral range used in the analysis. The polynomials are intended to provide constraints for spectral baseline effects. In addition, the user may supply spectra representative of other measurement process signals (e.g. water vapor spectra). These correction spectra (a matrix $X_s$ of dimension f by s where s is the number of correction spectra) which may include multiple examples of a specific type of measurement process signal, are first orthogonalized relative to the polynomials via a Gram-Schmidt orthogonalization procedure $$X_s' = X_s - U_p(U_p^t X_s) \tag{16}$$

A Singular Value Decomposition of the resultant correction spectra is then performed, $$X_s' = U_s \Sigma_s V_s^t \tag{17}$$

to generate a set of orthonormal correction eigenspectra, $U_s$. The user selects the first s' terms corresponding to the number of measurement related signals being modeled, and generates the full set of correction terms, $U_m$, which includes both the polynomials and selected correction eigenspectra. These correction terms are then removed from the calibration data, again using a Gram-Schmidt orthogonalization procedure $$X_c = X - U_m(U_m^t X) \tag{17}$$

The Principal Components Analysis of the corrected spectra, $X_c$, then proceeds via the Singular Value Decomposition $$X_c = U_c \Sigma_c V_c^t \tag{18}$$

and the predictive model is developed using the regression $$Y = V_c B \tag{19}$$

The resultant prediction vector $$P_c = U_c \Sigma_c^{-1} V_c^t Y \tag{20}$$

is orthogonal to the polynomial and correction eigenspectra, $U_m$. The resulting predictive model is thus insensitive to the modeled measurement process signals. In the analysis of an unknown, the contributions of the measurement process signals to the spectrum can be calculated as $$v_m = \Sigma_m^{-1} U_m^t x \tag{21}$$

and these values can be compared against the values for the calibration, $V_m$, to provide diagnostic as to whether the measurement process has changed relative to the calibration.

The results of the procedure described above are mathematically equivalent to including the polynomial and correction terms as spectra in the data matrix, and using a constrained least square regression to calculate the B matrix in equation 12. The constrained least square procedure is more sensitive to the scaling of the correction spectra since they must account for sufficient variance in the data matrix to be sorted into the k eigenspectra that are retained in the regression step. By orthogonalizing the calibration spectra to the correction spectra before calculating the singular value decomposition, we eliminate the scaling sensitivity.

The Constrained Principal Spectra Analysis method allows measurement process signals which are present in the spectra of the calibration samples, or might be present in the spectra of samples which are latter analyzed, to be modeled and removed from the data (via a Gram-Schmidt orthogonalization procedure) prior to the extraction of the spectral variables which is performed via a Singular Value Decomposition (16). The spectral variables thus obtained are first regressed against the pathlengths for the calibration spectra to develop a model for independent estimation of pathlength. The spectral variables are rescaled to a common pathlength based on the results of the regression and then further regressed against the composition/property data to build the empirical models for the estimation of these parameters. During the analysis of new samples, the spectra are collected and decomposed into the constrained spectral variables, the pathlength is calculated and the data is scaled to the appropriate pathlength, and then the regression models are applied to calculate the composition/property data for the new materials. The orthogonalization procedure ensures that the resultant measurements are constrained so as to be insensitive (orthogonal) to the modeled measurement process signals. The internal pathlength calculation and renormalization automatically corrects for pathlength or flow variations, thus minimizing errors due to data scaling.

The development of the empirical model consists of the following steps:

(1.1) The properties and/or component concentrations for which empirical models are to be developed are independently determined for a set of representative samples, e.g. the calibration set. The independent measurements are made by standard analytical tests including, but not limited to: elemental compositional analysis (combustion analysis, X-ray fluorescence, broad line NMR); component analysis (gas chromatography, mass spectroscopy); other spectral measurements (IR, UV/visible, NMR, color); physical property measurements (API or specific gravity, refractive index, viscosity or viscosity index); and performance property measurements (octane number, cetane number, combustibility). For chemicals applications where the number of sample components is limited, the compositional data may reflect weights or volumes used in preparing calibration blends.

(1.2) Absorption spectra of the calibration samples are collected over a region or regions of the infrared, the data being digitized at discrete frequencies (or wavelengths) whose separation is less than the width of the absorption features exhibited by the samples.

(2.0) The Constrained Principal Spectra Analysis (CPSA) algorithm is applied to generate the empirical model. The algorithm consists of the following 12 steps:

(2.1) The infrared spectral data for the calibration spectra is loaded into the columns of a matrix X, which is of dimension f by n where f is the number of frequencies or wavelengths in the spectra, and n is the number of calibration samples.

(2.2) Frequency dependent polynomials, $U_p$, (a matrix whose columns are orthonormal Legendre polynomials having dimension f by p where p is the maximum order of the polynomials) are generated to model possible variations in the spectral baseline over the spectral range used in the analysis.

(2.3) Spectra representative of a other types of measurement process signals (e.g. water vapor spectra, carbon dioxide, etc.) are loaded into a matrix $X_s$ of dimension f by s where s is the number of correction spectra used.

(2.4) The correction spectra are orthogonalized relative to the polynomials via a Gram-Schmidt orthogonalization procedure $$X_s' = X_s - U_p(U_p^t X_s) \qquad (2.4)$$

(2.5) A Singular Value Decomposition of the correction spectra is then performed, $$X_s' = U_s \Sigma_s V_s^t \qquad (2.5)$$

to generate a set of orthonormal correction eigenspectra, $U_s$. $\Sigma_s$ are the corresponding singular values, and $V_s$ are the corresponding right eigenvectors, $^t$ indicating the matrix transpose.

(2.6) The full set of correction terms, $U_m = U_p + U_s$, which includes both the polynomials and correction eigenspectra are then removed from the calibration data, again using a Gram-Schmidt orthogonalization procedure $$X_c = X - U_m(U_m^t X) \qquad (2.6)$$

(2.7) The Singular Value Decomposition of the corrected spectra, $X_c$, is then performed $$X_c = U_c \Sigma_c V_c^t \qquad (2.7)$$

(2.8) The eigenspectra from step (2.7) are examined and the a subset of the first k eigenspectra which correspond to the larger singular values in $\Sigma_c$ are retained. The k+1 through n eigenspectra which correspond to spectral noise are discarded.

$$X_c = U_k \Sigma_k V_k^t + E_k \qquad (2.8)$$

(2.9) The k right eigenvectors from the singular value decomposition, $V_k$, are regressed against the pathlength values for the calibration spectra, $Y_p$ (an n by 1 row vector), $$Y_p = V_k B_p + E_p \qquad (2.9a)$$

where $E_p$ is the regression error. The regression coefficients, $B_p$, are calculated as $$B_p = (V_k^t V_k)^{-1} V_k^t Y_p = V_k^t Y_p \qquad (2.9b)$$

(2.10) An estimation of the pathlengths for the calibration spectra is calculated as $$\hat{Y}_p = V_k B_p \qquad (2.10)$$

A n by n diagonal matrix N is then formed, the $i^{th}$ diagonal element of N being the ratio of the average pathlength for the calibration spectra, $\bar{y}_p$, divided by the estimated pathlength values for the $i^{th}$ calibration sample (the $i^{th}$ element of $\hat{Y}_p$).

(2.11) The right eigenvector matrix is then renormalized as $$V_k' = NV_k \tag{2.11}$$

(2.12) The renormalized matrix is regressed against the properties and or concentrations, Y (Y, a n by c matrix containing the values for the n calibration samples and the c property/concentrations) to obtain the regression coefficients for the models, $$Y = V_k'B + E \tag{2.12a}$$

$$B = (V_k'^tV_k')^{-1}V_k'Y \tag{2.12b}$$

(3.0) The analysis of a new sample with unknown properties/components proceeds by the following steps:

(3.1) The absorption spectrum of the unknown is obtained under the same conditions used in the collection of the calibration spectra.

(3.2) The absorption spectrum, $x_u$, is decomposed into the constrained variables, $$x_u = U_k \Sigma_k v_u^t \tag{3.2a}$$

$$v_u = \Sigma^{-1} U_k^t x_u \tag{3.2b}$$

(3.3) The pathlength for the unknown spectrum is estimated as $$\hat{y}_p = v_u B_p \tag{3.3}$$

(3.4) The eigenvector for the unknown is rescaled as $$v_u' = v_u(\bar{y}_p/\hat{y}_p) \tag{3.4}$$

where $\bar{y}_p$ is the average pathlength for the calibration spectra in (2.10).

(3.5) The properties/concentrations are estimated as $$\hat{y}_u = v_u'B \tag{3.5}$$

(4.1) The spectral region used in the calibration and analysis may be limited to subregions so as to avoid intense absorptions which may be outside the linear response range of the spectrometer, or to avoid regions of low signal content and high noise.

(5.1) The samples used in the calibration may be restricted by excluding any samples which are identified as multivariate outliers by statistical testing.

(6.1) The regression in steps (2.9) and (2.12) may be accomplished via a step-wise regression (17) or PRESS based variable selection (18), so as to limit the number of variables retained in the empirical model to a subset of the first k variables, thereby eliminating variables which do not show statistically significant correlation to the parameters being estimated.

(7.1) The Mahalanobis statistic for the unknown, $D_u^2$, given by $$D_u^2 = v_u'(V_k'^tV_k')^{-1}v_u'^t \tag{7.1}$$

can be used to determine if the estimation is based on an interpolation or extrapolation of the model by comparing the value for the unknown to the average of similar values calculated for the calibration samples.

(7.2) The uncertainty on the estimated value can also be estimated based on the standard error from the regression in (2.12) and the Mahalanobis statistic calculated for the unknown.

(8.1) In the analysis of an unknown with spectrum $x_u$, the contributions of the measurement process signals to the spectrum can be calculated as $$v_m = \Sigma_c^{-1}U_m^t x_u \tag{8.1}$$

These values can be compared against the values for the calibration, $V_m$, to provide diagnostics as to whether the measurement process has changed relative to the calibration.

EXAMPLES

Examples of the use of the CPSA method described above for the generation of empirical models are provided for cases illustrating the use of different portions of the infrared region, and the estimation of compositions as well as physical and performance properties. These examples are identified as Examples 1 to 5 below and the results are illustrated in FIGS. 1 to 5 respectively. These figures demonstrate the validity of the present method of estimating property and composition data.

EXAMPLE 1

Estimation of a Component Concentration using Mid-Infrared

| Parameter estimated | Weight precent benzene |
| --- | --- |
| Sample types | Powerformates |
| Calibration samples measured by | Gas Chromatography |
| Spectrometer used | Mattson Polaris/Icon |
| Average Pathlength Calibration set | 500 microns |
| Spectral range used | 5000–1645 cm$^{-1}$ |
| Excluded subregions | 3150–2240 cm$^{-1}$ |
| Constraints used | 3 polynomial terms (quadratic) |
| | Water vapor spectrum |
| Regression method used | PRESS |
| Number of calibration spectra | 77 |
| # eigenspectra used in regressions (k) | 5 |
| # retained in pathlength regression | 4 |
| Standard Error Pathlength Regression | 1.272 microns |
| # retained in composition regression | 5 |
| Standard Error composition regression | 0.063 weight percent |

A Constrained Principal Components model was constructed for the estimation of benzene content of powerformates. The spectra of 77 reference powerformates were collected over the 5000 to 1645 cm$^{-1}$ region using a Mattson Polaris/Icon FT-IR spectrometer operating at 2 cm$^{-1}$ resolution and employing 100 scans for signal averaging. 500 micron calcium floride cells were employed. To avoid ranges where the sample absorption was beyond the linear response range of the spectrometer, and to avoid the need for adding a carbon dioxide correction term to the model, the data in the 3150–2240 cm$^{-1}$ region were excluded during the model generation. Benzene contents for the reference samples used in the calibration were obtained via gas chromatographic analysis. A CPSA model was developed using 3 polynomial correction terms to account for possible background variations, and a water vapor correction spectrum to account for possible purge variations. A PRESS based step-wise regression (the PRESS based step-wise regression algorithm is described in detail in Section 1.4.3.2 of the Appendix to this specification which is located after the examples) was employed for developing both a pathlength estimation model, and the benzene content. Of the 5 Constrained Principal Component variable input into the PRESS regression, 4 were retained for the pathlength estimation, and all 5 were retained for the benzene estimation. The standard error for the estimation of the cell pathlength was 1.272 microns, and the standard error for the estimation of the benzene content was 0.063 weight percent. A plot of the infrared estimated benzene content versus that measured by GC for the 77 reference samples is shown in FIG. 1.

EXAMPLE 2

Physical Property Estimation by Mid-Infrared

| Parameter estimated | API Gravity |
|---|---|
| Sample types | Petroleum mid-distillate |
| Calibration samples measured by | ASTM D1298 |
| Spectrometer used | Mattson Polaris/Icon |
| Average Pathlength Calibration set | 29.57 microns |
| Spectral range used | 3650–500 $cm^{-1}$ |
| Excluded subregions | 2989–2800 $cm^{-1}$, 2400–2300 $cm^{-1}$, 1474–1407 $cm^{-1}$ |
| Constraints used | 3 polynomial terms (quadratic) Water vapor spectrum |
| Regression method used | PRESS |
| Number of calibration spectra | 91 |
| # eigenspectra used in regressions (k) | 24 |
| # retained in pathlength regression | 21 |
| Standard Error Pathlength Regression | 0.159 microns |
| # retained in composition regression | 21 |
| Standard Error composition regression | 0.660 degrees API |

Figure 2:
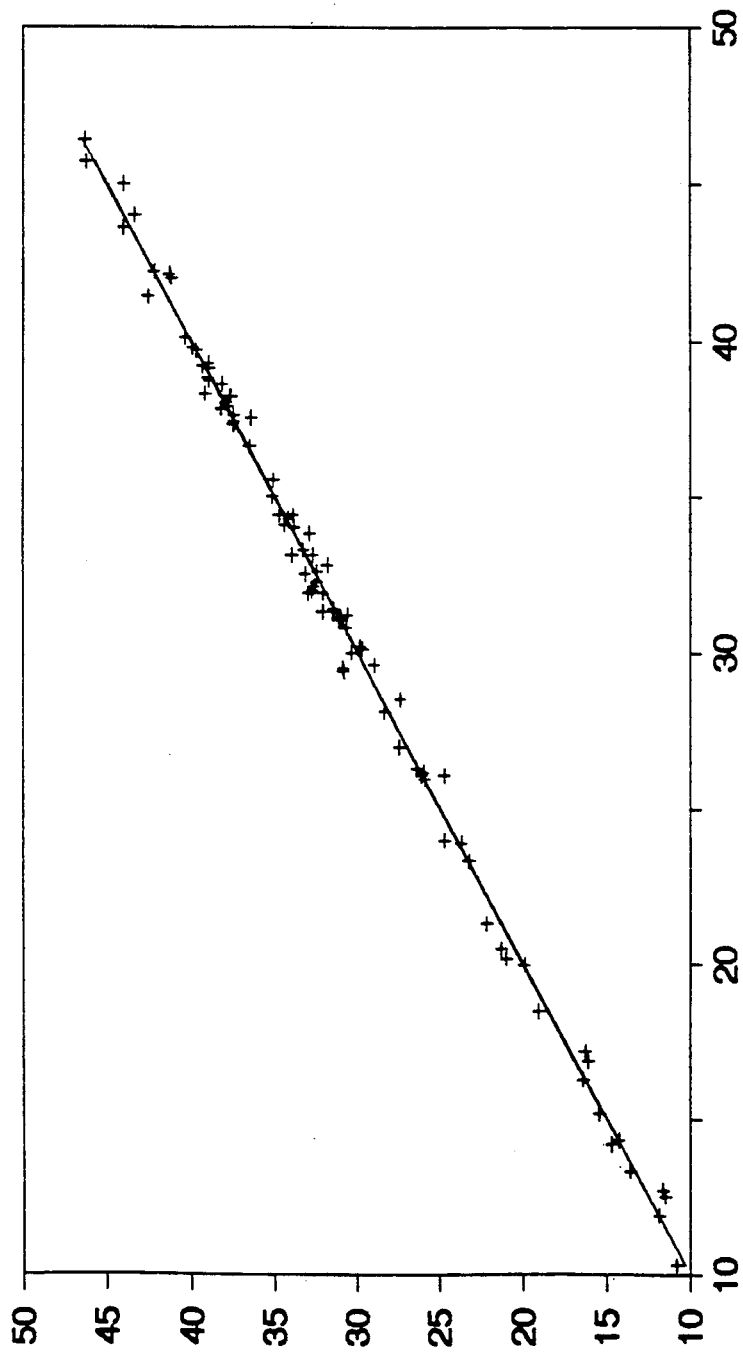

A Constrained Principal Components model was constructed for the estimation of API Gravity for petroleum mid-distillates. The spectra of 91 reference mid-distillates were collected over the 3650 to 500 $cm^{-1}$ region using a Mattson Polaris/Icon FT-IR spectrometer operating at 2 $cm^{-1}$ resolution and employing 100 scans for signal averaging. 30 micron potassium bromide cells were employed. To avoid ranges where the sample absorption was beyond the linear response range of the spectrometer, and to avoid the need for adding a carbon dioxide correction term to the model, the data in the 2989–2800 $cm^{-1}$, 2400–2300 $cm^{-1}$ and 1474–1407 $cm^{-1}$ regions was excluded during the model generation. API Gravities for the reference samples used in the calibration were obtained via ASTM D1298. A CPSA model was developed using 3 polynomial correction terms to account for possible background variations, and a water vapor correction spectrum to account for possible purge variations. A PRESS based step-wise regression (Section 1.4.3.2 of the appendix) was employed for developing both a pathlength estimation model, and the API Gravity. Of the 24 Constrained Principal Component variable input into the PRESS regression, 19 were retrained for the pathlength estimation, and 21 were retained for the API Gravity estimation. The standard error for the estimation of the cell pathlength was 0.159 microns, and the standard error for the estimation of the API Gravity was 0.660 degrees API. A plot of the infrared estimated API Gravity versus that measured by ASTM D1298 for the 91 reference samples is shown in FIG. 2.

EXAMPLE 3

Estimation of a Performance Property using Near-Infrared

| Parameter estimated | Cetane number |
|---|---|
| Sample types | Petroleum mid-distillates |
| Calibration samples measured by | ASTM D-613 |
| Spectrometer used | Mattson Sirius 100 |
| Average Pathlength Calibration set | 519.3 microns |
| Spectral range used | 10000–3800 $cm^{-1}$ |
| Excluded subregions | none |
| Constraints used | 3 polynomial terms (quadratic) |
| Regression method used | PRESS |
| Number of calibration spectra | 93 |
| # eigenspectra used in regressions (k) | 13 |
| # retained in pathlength regression | 11 |
| Standard Error Pathlength Regression | 1.535 microns |
| # retained in composition regression | 10 |
| Standard Error composition regression | 1.258 cetane number |

Figure 3:
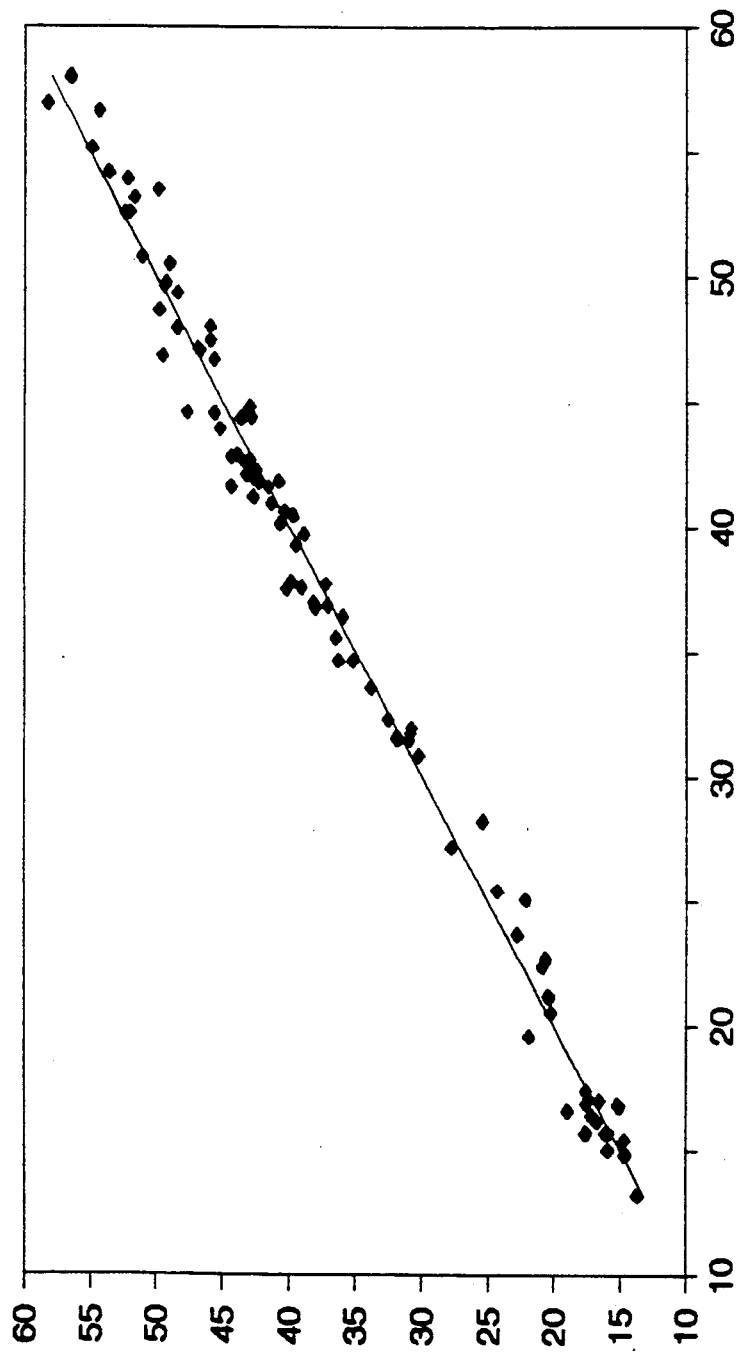

A Constrained Principal Components model was constructed for the estimation of Cetane Number for petroleum mid-distillates. The spectra of 91 reference mid-distillates were collected over the 10000 to 3800 $cm^{-1}$ region using a Mattson Sirius 100 FT-IR spectrometer operating at 2 $cm^{-1}$ resolution and employing 100 scans for signal averaging. 500 micron calcium floride cells were employed. Cetane numbers for the reference samples used in the calibration were obtained via ASTM D-613. A CPSA model was developed using 3 polynomial correction terms to account for possible background variations. A PRESS based step-wise regression (Section 1.4.3.2 of the appendix) was employed for developing both a pathlength estimation model, and the API Gravity. Of the 13 Constrained Principal Component variable input into the PRESS regression, 11 were retained for the pathlength estimation, and 10 were retained for the API Gravity estimation. The standard error for the estimation of the cell pathlength was 1.535 microns, and the standard error for the estimation of the cetane number was 1.258 cetane numbers. A plot of the infrared estimated cetane number versus that measured by ASTM D-613 for the 91 reference samples is shown in FIG. 3.

EXAMPLE 4

Elemental Composition Esimation by Mid-Infrared

| Parameter estimated | Weight percent hydrogen |
|---|---|
| Sample types | Petroleum mid-distillate |
| Calibration samples measured by | Broad line NMR |
| Spectrometer used | Mattson Polaris/Icon |
| Average Pathlength Calibration set | 29.57 microns |
| Spectral range used | 3650–500 $cm^{-1}$ |
| Excluded subregions | 2989–2800 $cm^{-1}$, 2400–2300 $cm^{-1}$, 1474–1407 $cm^{-1}$ |
| Constraints used | 3 polynomial terms (quadratic) Water vapor spectrum |
| Regression method used | PRESS |
| Number of calibration spectra | 91 |
| # eigenspectra used in regressions (k) | 24 |
| # retained in pathlength regression | 19 |
| Standard Error Pathlength Regression | 0.159 microns |
| # retained in composition regression | 21 |
| Standard Error composition regression | 0.0551 degrees API |

Figure 4:
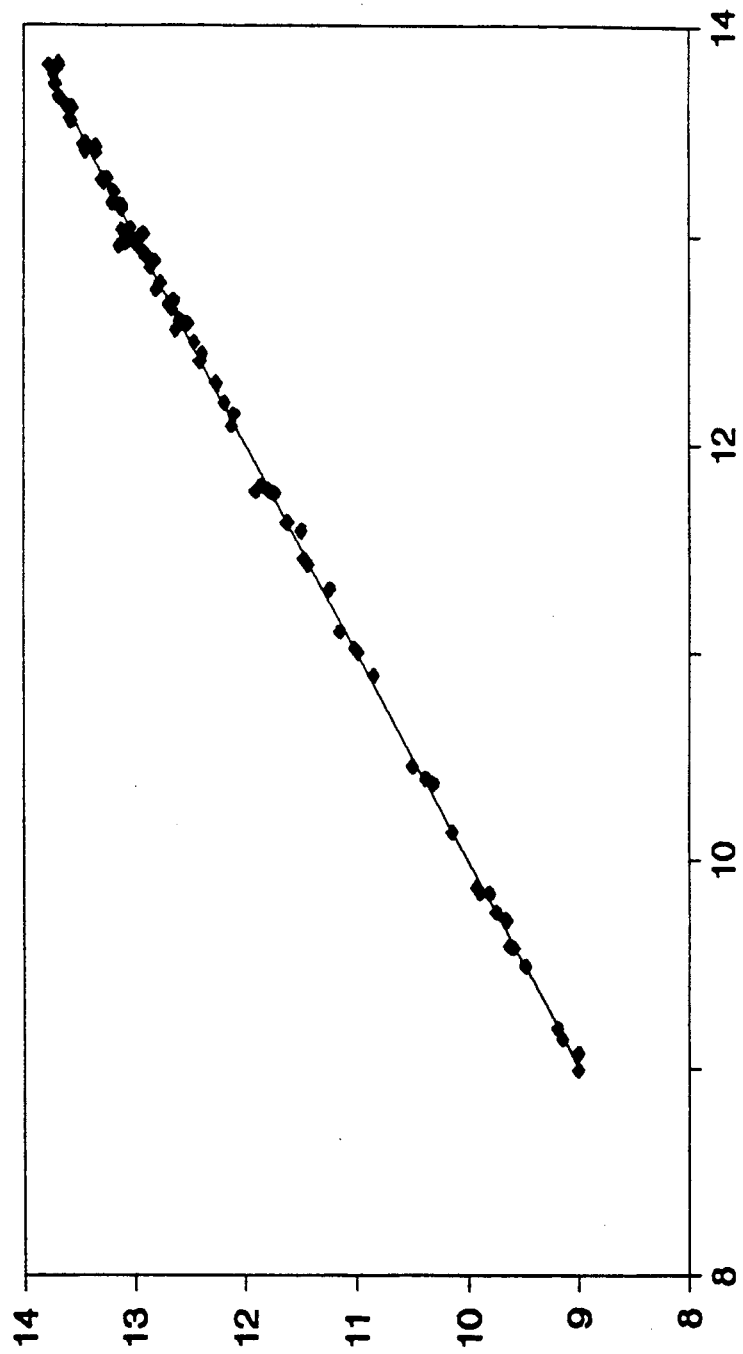

A Constrained Principal Components model was constructed for the estimation of hydrogen content for petroleum mid-distillates. The spectra of 91 reference mid-distillates were collected over the 3650 to 500 cm$^{-1}$ region using a Mattson Polaris/Icon FT-IR spectrometer operating at 2 cm$^{-1}$ resolution and employing 100 scans for signal averaging. 30 micron potassium bromide cells were employed. To avoid ranges where the sample absorption was beyond the linear response range of the spectrometer, and to avoid the need for adding a carbon dioxide correction term to the model, the data in the 2989-2800 cm$^{-1}$, 2400-2300 cm$^{-1}$ and 1474-1407 cm$^{-1}$ regions was excluded during the model generation. Hydrogen contents for the reference samples used in the calibration were obtained via Broad line NMR. A CPSA model was developed using 3 polynomial correction terms to account for possible background variations, and a water vapor correction spectrum to account for possible purge variations. A PRESS based step-wise regression (Section 1.4.3.2) was employed for developing both a pathlength estimation model, and the API Gravity. Of the 24 Constrained Principal Component variable input into the PRESS regression, 19 were retained for the pathlength estimation, and 21 were retained for the hydrogen content estimation. The standard error for the estimation of the cell pathlength was 0.159 microns, and the standard error for the estimation of the hydrogen content was 0.0551 weight percent hydrogen. A plot of the infrared estimated hydrogen content versus that measured by broad line NMR for the 91 reference samples is shown in FIG. 4.

EXAMPLE 5

Chemical Composition Estimation by Mid-Infrared

| | |
|---|---|
| Parameter estimated | Weight precent ZDDP |
| Sample types | Lubricant additive package |
| Calibration samples measured by | Weight % in blends |
| Spectrometer used | Digilab FTS-20C |
| Average Pathlength Calibration set | 62.0 microns |
| Spectral range used | 1800–490 cm$^{-1}$ |
| Excluded subregions | 1475–1435 cm$^{-1}$ |
| Constraints used | 3 polynomial terms (quadratic) Water vapor spectrum |
| Regression method used | Step-wise |
| Number of calibration spectra | 30 |
| # eigenspectra used in regressions (k) | 7 |
| # retained in pathlength regression | 7 |
| Standard Error Pathlength Regression | 0.17 microns |
| # retained in composition regression | 7 |
| Standard Error composition regression | 0.16 weight percent |

Figure 5:
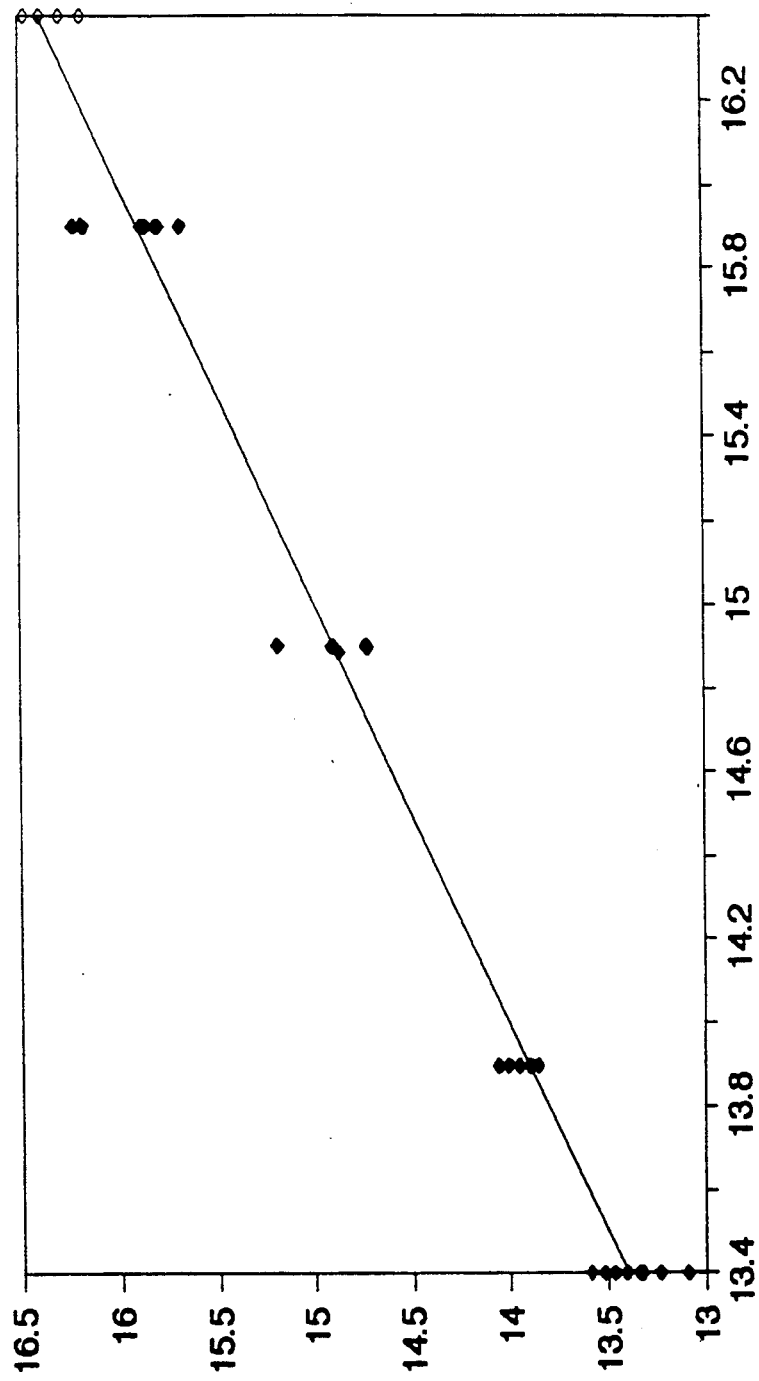
Figure 7A:
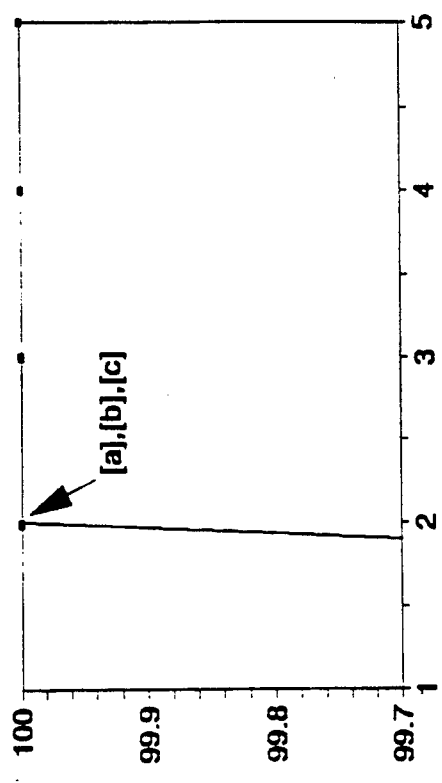
FIGS. 7A-7D are statistics for analysis of data set [1] where the abscissa for each of 7A, 7B, 7C, 7D is logeigen value, cumulative precent variance, indicator function, and eigen value ratio (Times 10E12), respectively, plotted against number of principal components.
Figure 7B:
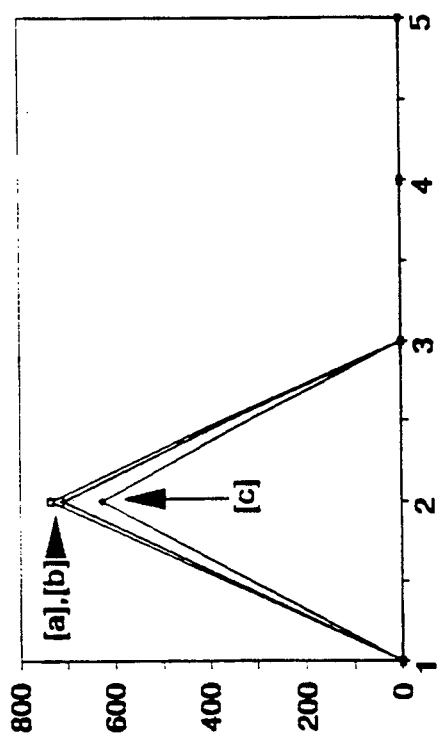
Figure 7C:
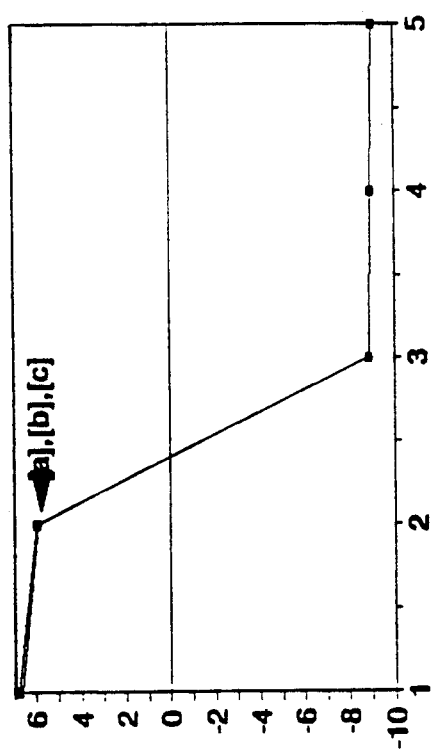
Figure 7D:
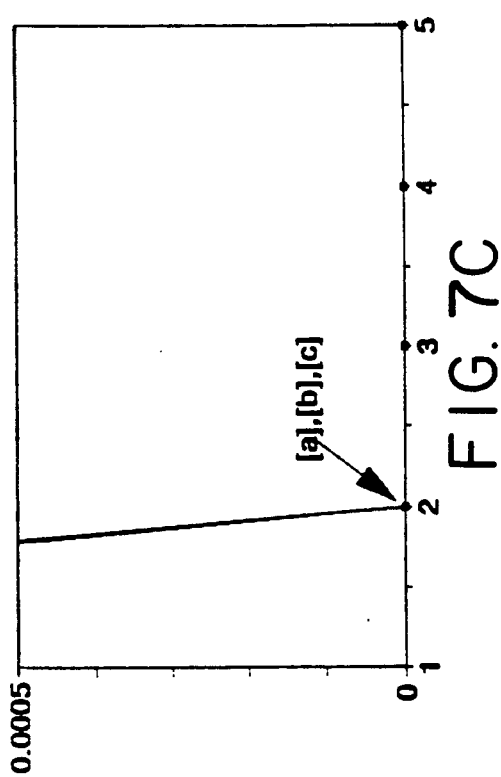
Figure 8A:
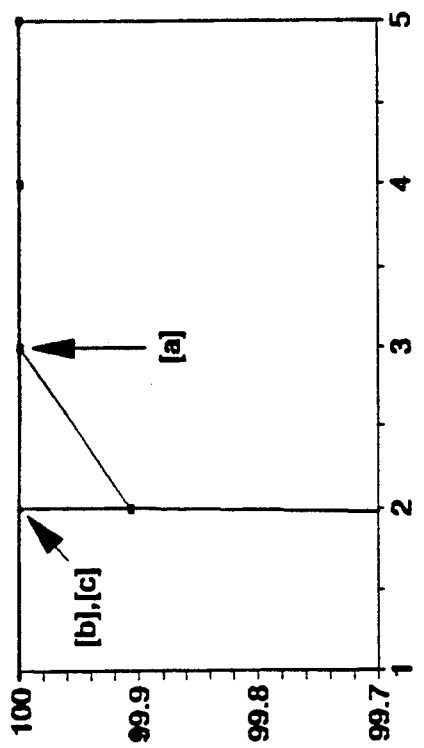
FIGS. 8A-8D are statistics for analysis of data set [2] the abscissa and ordinate for each of 8A, 8B, 8C, and 8D being the same as for FIG. 7.
Figure 8B:
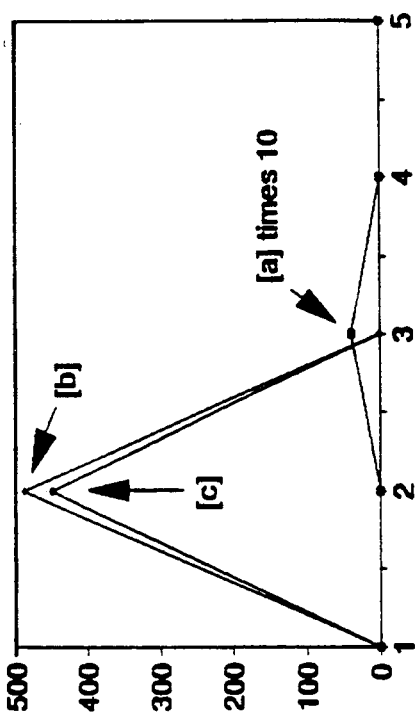
Figure 8C:
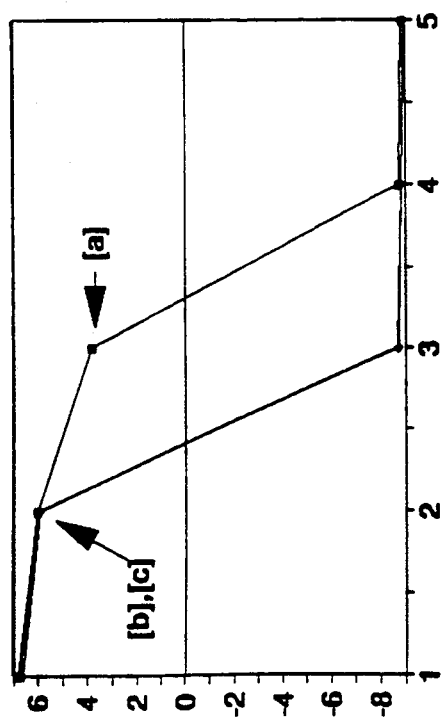
Figure 8D:
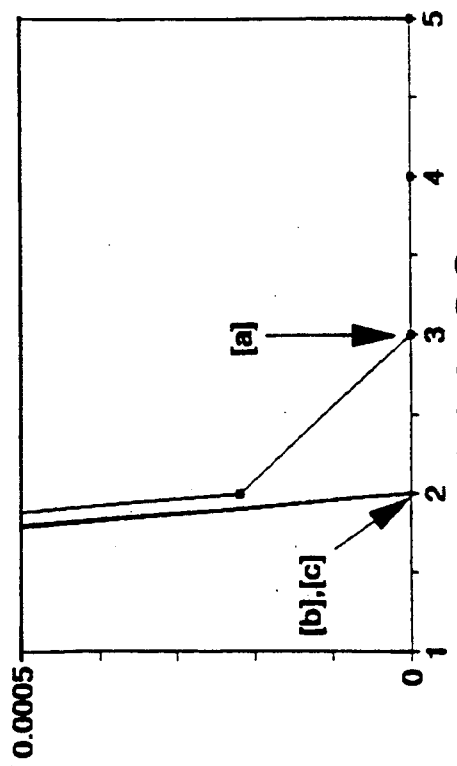
Figure 9A:
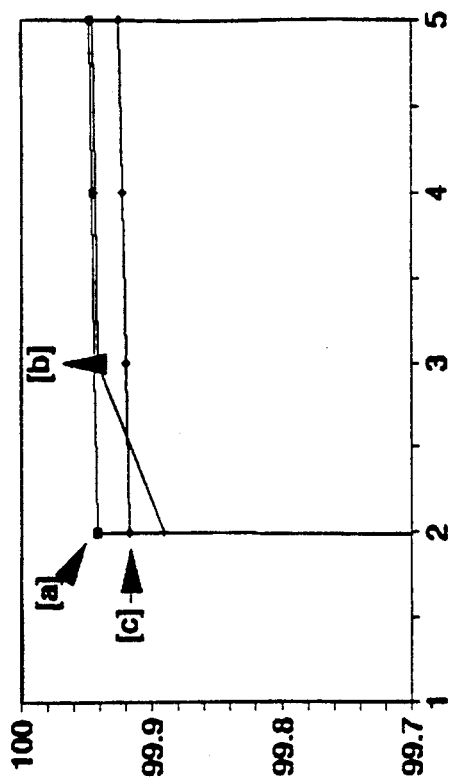
FIGS. 9A-9D are statistics for analysis of data set [3], the abscissa and ordinate for each of 9A, 9B, 9C, and 9D being the same as for FIG. 7.
Figure 9B:
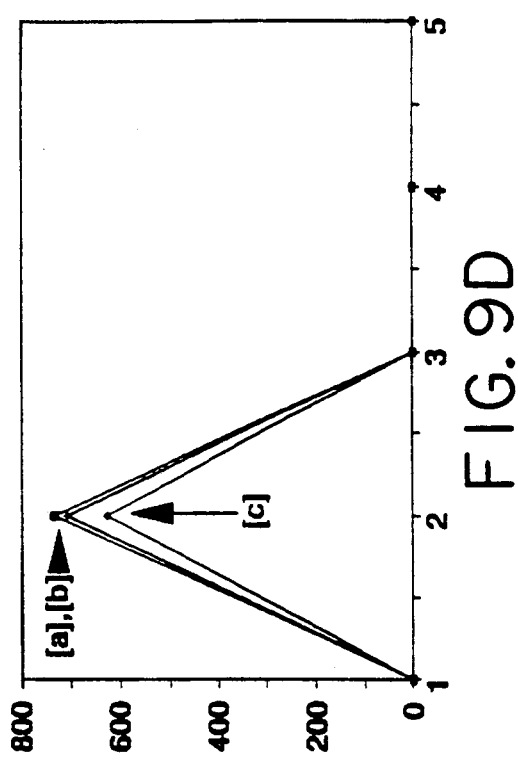
Figure 9C:
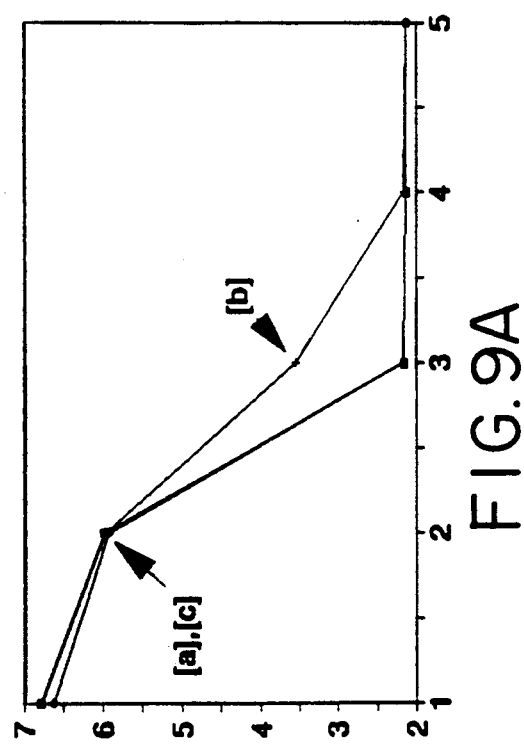
Figure 9D:
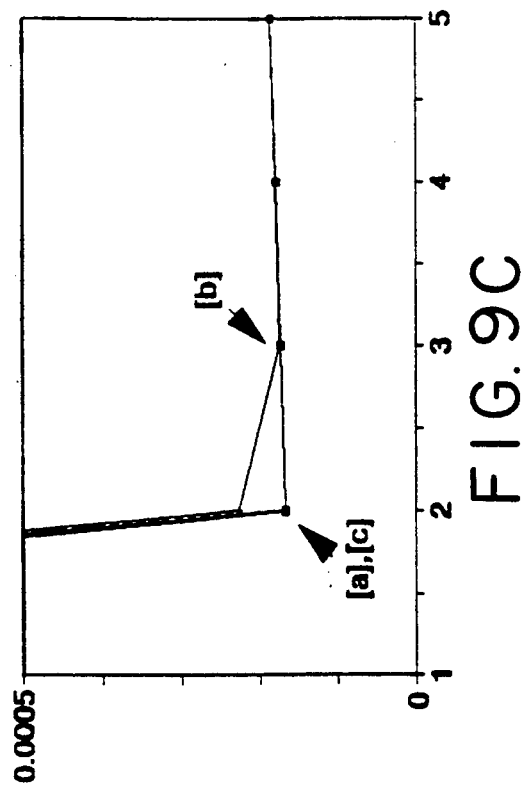

A Constrained Principal Components model was constructed for the estimation of the zinc dialkyl dithiophosphate (ZDDP) content for lubricant additive packages. 30 reference blends of an additive package containing a polyisobutenyl polyamine dipersant, a over-based magnesium sulfonate detergant, a sulfurized nonyl phenol, ZDDP and diluent oil were prepared for the calibration. The additive concentrations in the reference blends were varied at +/−8 to 12 percent of the target concentrations. Solutions containing 50% additive package in cyclohexane were prepared and spectra were collected over the 3650 to 400 cm$^{-1}$ region using a Digilab FTS-20C FT-IR spectrometer operating at 2 cm$^{-1}$ resolution. 100 scans were employed for signal averaging. 62 micron potassium bromide cells were employed. The CPSA model was developed using spectra data in the 1800-1475 and 1435-490 cm$^{-1}$ regions. A CPCR model was developed using 3 polynomial correction terms to account for possible background variations, and a water vapor correction spectrum to account for possible purge variations. A step-wise regression (Section 1.4.3.2 of the appendix) was employed for developing both a pathlength estimation model, and the ZDDP content. Of the 7 Constrained Principal Component variable input into the PRESS regression, 7 were retained for the pathlength estimation, and 7 were retained for the ZDDP content estimation. The standard error for the estimation of the cell pathlength was 0.17 microns, and the standard error for the estimation of the ZDDP content was 0.16 weight percent. A plot of the infrared estimated ZDDP content versus that used in preparing the 30 blends is shown in FIG. 5.

Further examples will now be given.

EXAMPLE 6

Synthetic data for a Binary System with Variable Offset

To further illustrate the operation of the CPSA algorithm, a series of synthetic (computer generated) spectra were calculated and analyzed. Two components were used to synthesize the spectra, component A being represented by a Lorentzian band at 1350 cm$^{-1}$ with a half band width at half maximum of 20 cm$^{-1}$ and an absorbance of 1, and component B being represented by a Lorentzian band at 1150 cm$^{-1}$ having the same width and an absorbance of 0.5. 101 mixture spectra were generated by adding the spectra of the components together. Four sets of mixture spectra were generated:

[1] the mixture spectra generated as the sum of the spectrum of component A whose concentration varied from 0% to 100% at 1% intervals, and the spectrum of component B whose concentration was adjusted such that the concentrations add to 100%;

[2] the same spectra as in [1] with a variable absorbance offset added. The level of the offset added to each spectrum was calculated using a Gaussian random number generator (20), and scaled so as to produce a normal distribution with an average offset of 0.01 absorbance units and a standard deviation of 0.01 absorbance units;

[3] the same spectra as in [1] with random, normally distributed noise added. The noise was generated using a Gaussian noise generator so as to have a root-mean-square value of approximately 0.45 absorbance units;

[4] the same spectra as in [1] with the same offsets as [2] and the same noise as [3].

The 51 mixture spectra for which the concentrations were even percentages were used as calibration spectra, and the remaining 50 mixture spectra were used as test sets. Table 1 (set out, together with Tables 2 to 9 referred to herein below, after Example 11) lists the concentrations and offsets used in generating the 51 calibration spectra, and Table 2 lists the corresponding values for the 50 test spectra. FIG. 6 shows examples of the 50/50 mixture spectra for the four cases. Three separate types of models designed to predict the concentrations of component A were generated:

[a] a model based on a PCA analysis of the as generated spectra;

[b] a model based on a PCA analysis of the spectra which had been background corrected using an algorithm which involves: calculation of the average of the calibration spectra; determination of the frequency at which the minimum absorption occurs in the average spectrum; offsetting each calibration spectrum by its absorption at this frequency.

[c] a model based on a CPSA analysis where a first order (constant) polynomial correction was applied as a constraint.

The models were used to predict the component A concentrations for test sets.

FIGS. 7-10 show plots of some of the statistics typically used to estimate the number of Principal Components present in spectral data. For data set [1], where only signals due to the two components are present, all the statistics confirm the presence of two Principal Components (FIG. 7). The plot of the logarithm of the eigenvalues show a sharp drop after two components. The indicator function reaches its minimum value (zero), the cumulative variance reaches 100%, and the ratio of successive eigenvalues reaches a maximum at two Principal Components. When a variable offset is present in the data (data set [2], FIG. 8), a Principal Components Analysis of the untreated spectra (analysis [a]) indicates the presence of three sources of variance. As is typical with real spectra, the statistical tests do not distinguish between variance arising from sharp absorption features (sample components) and variance due to broad fluctuations in the spectral background. In the absence of spectral noise, both the preprocessing and the constrained analysis are equally effective at removing the background signal, and isolating the two variables corresponding to the component absorptions. When spectral noise is considered, the effects of the preprocessing and the constrained analysis are quite different. For the analysis of data set [3], where only spectral noise was included (FIG. 9), both the normal PCA (analysis [a]) and the CPSA (analysis [c]) indicate the presence of two Principal Components. The preprocessing can be seen to introduce a third source of variance. The single point background correction is actually introducing an offset which is correlated to the noise at the point of correction. Since the constrained analysis uses all of the data in calculating the offset correction, it is not as sensitive to the presence of the noise and does not introduce additional variance. When both the noise and the variable offset are present (data set [4], FIG. 10), the straight PCA (analysis [a]) again finds three Principal Components. The single point background correction (analysis [b]) is ineffective at removing the background variation, substituting a offset that is correlated to the noise at the correction point for the original offset, and again three PCs are indicated by the majority of the statistical tests. The CPSA analysis (analysis [c]) effectively eliminates the offset even in the presence of the noise, thereby isolating the two spectral variables corresponding to the component absorptions.

Table 3 shows Standard Errors of Estimate (calibration sets) and Standard Errors of Prediction (test sets) for the three analyses applied to the four different data sets. In the absence of offset or noise (data set [1]), all three analyses produce models based on two Principal Components which are perfect to within the roundoff error of the algorithms ($<10^{-6}$). When the variable offset is present (data set [2]), analysis [a] requires three Principal Components to produce the same level of accuracy. Since, in the absence of noise, both the preprocessing and the constrained analysis successfully eliminated the background signal, models based on two Principal Components can be built for both [b] and [c]. The straight Principal Components Analysis (analysis [a]) of data set [3] serves as a base case to illustrate the effect of the spectral noise on the analysis. The random noise in the spectral data introduces an error on the order of 0.06–0.08% into the model. Since, as was indicated above, the preprocessing (analysis [b]) actually introduces an additional source of variance into the data, three Principal Components are required for model [b] to achieve a similar level of accuracy. Since the constrained analysis (analysis [c]) is less affected by the noise, only two Principal Components are required in the model to achieve the same level of accuracy. Similarly, when both the noise and variable offset are present (data set [4]), three Principal Components are required for models [a] and [b], whereas only two variable are required for the constrained model, [c].

The preprocessing algorithm used in the above example clearly represents an extreme case since the correction is dependent on only a single spectral data point. Preprocessing algorithms which averaged several data points would be less sensitive to the spectral noise and more effective at removing the background signal. However, since the CPSA constraint makes use of all the spectral data, it must represent the alternate extreme, and as such, be the least sensitive to spectral noise.

For the analysis of data set 4 where both the variable offset and noise are present in the spectral data, the standard errors listed in Table 3 suggest that there is only slight advantage to the CPSA models based on two variables and a constraint over PCA models which include the third variable in the regression. For this data set, the random offset is essentially uncorrelated (correlation coefficient $r=0.007$) to the dependent variable (the component A concentration), and there is no error in the dependent variable. When possible correlations between the measurement process signals (e.g. the offset) and the dependent variable (or the error in the dependent variable) are considered, the advantage to using CPSA to remove the measurement process signals prior to the regression becomes clearer.

If a correlation exists between the measurement process signal and the component/property being modeled, the correlation can be incorporated into the model if the measurement process signal is not removed prior to the regression. For instance, it is not uncommon to use a single cell in collecting the calibration spectra, or to use a single background spectra for a series of sequential sample spectra. If the cell window gradually degrades, or if the spectrometer source temperature varies systematically, a nonrandom measurement related signal will be present among the calibration spectra. If, in addition, the calibration spectra are collected in a nonrandom order (e.g. in order of increasing concentration for a component), a correlation between the spectral background variation and the component/property being modeled may be generated. When the model is used in the future with a new cell and background, an error in the prediction will result from the spurious relationship which existed in the calibration set. While some of these types of correlations can be minimized by careful experimental design (e.g. by running spectra in random order, using multiple cells and collecting frequent backgrounds), such experimental design is not always consistent with the availability of the samples, equipment or time for collection of the data. By allowing the spectroscopist to model and remove the measurement related signals prior to the model development, CPSA prevents extraneous correlations from being incorporated into the model, thereby improving the robustness of the predictions.

To illustrate the effect of a correlation between the measurement related signals and the component concentrations, a fifth synthetic data set was generated. The 101 spectra were generated in the same fashion as those for data set [4], with the exception that the offsets for the 51 calibration samples were put into increasing numerical order prior to the calculation of the spectra (Table 1, second offset column). In this case, the correlation between the offset and the component A concentration is high (r=0.825). As seen from Table 4, a PCA model based on three variables and a CPSA model based on two variables plus one constraint produce models with identical Standard Errors of Estimate. However, the third variable in the PCA model corresponds to the measurement process signal (the offset), and the predictive model includes the relationship which existed between the offset and the component A concentration for the calibration set. When the PCA model is used to analyze the test samples for which the relationship between the offset and the component A concentration no longer holds, the Standard Error of Prediction is found to be four times larger than would be suggested from the calibration. By constraining the model to be independent of the measurement process signal, the CPSA analysis prevents the correlation between the offset and the component A concentration from being incorporated into the model, thereby producing a more robust prediction. By modeling and removing the measurement process signals prior to the regression, the CPSA algorithm prevents the incorporation of spurious correlations between the measurement process signals and the property/component, thereby producing a more stable and robust predictive model.

In the above examples, there is no error in the dependent variable, Y, which corresponded directly to the component A concentrations used to generate the spectra. The variance in Y can be totally explained on the basis of the component absorptions. For real analyses, however, the dependent variable is usually also a measured quantity, and includes some measurement error. In this case, the possibility exists that measurement process signals present in the spectral data may be correlated to the error in dependent variable, and models which include the measurement signals as variables will again contain spurious relationships which decrease the robustness of the predictions.

To illustrate this point, the above analyses were repeated using dependent variables which included error. A set of 51 normally distributed errors were generated having a standard deviation of 0.3. Dependent variables were generated by adding errors to the component A concentrations prior to the regressions. Two cases were developed. In case 1, the error values were arranged so as to be uncorrelated (r=0.000021) to the offsets used in generating the spectra in data sets [2] and [4]. In case 2, the errors were arranged to be highly correlated (r=0.96) to the offsets. 50 of the 51 error values were added to the component A concentrations for the test set, the errors being arranged so as to be uncorrelated (r=0.000056) to the offsets. The error values used in each case are listed in Table 1. Table 5 shows the standard errors for the various models.

Analyses [a] of data sets [1] and [3] serve as base cases for this example. For data set [1], where there is no offset or noise in the spectral data, the Standard Errors of Estimate for the calibrations correspond to the standard deviations in the dependent value error, corrected for the degrees of freedom in the models. The reordering of the error values between the two cases leads to slightly different predictive models, but the differences are not statistically significant. For data set [3], there is a slight increase in the model errors due to the spectral noise, but the major source of error in the models remains the error in the dependent variable. Note that the Standard Errors of Estimate and Prediction indicate how well the model agrees with the dependent variable which includes error. The models predict the true values (the concentrations used in generating the spectra) more accurately than the dependent variable values used in developing the model which included the error. There is some bias in the models since, for the finite number of calibration samples used, the distribution of the error in the dependent variable is not totally random.

For data sets [2] and [4] which includes the offset, three variables are present in the spectral data. In the absence of spectral noise (data set [2]), the third variable (the offset) can be removed by either preprocessing (analysis [b]) or the constraint relationship (analysis [c]) to produce models where the accuracy is limited only by the error in the dependent values. For both data sets, the results obtained for models which include all three variables in the regression (analyses [a]) are highly dependent on the degree of correlation between the offset and the error in the dependent variable. If these two are uncorrelated, an accurate model can be produced. If the error and the offset are correlated, this extraneous relationship is incorporated into the model producing an artificially low SEE. When test samples for which this relationship does not hold are analyzed, the predictions are seen to be less accurate.

As was indicated above, in the presence of spectral noise, the single point preprocessing algorithm (analysis [b]) is ineffective at removing the offset. For data set [3], the preprocessing actually introduces an additional variable correlated to the noise at the correction point, whereas for data set [4], the preprocessing substitutes the noise correlated source of variation for the variable offset. In both cases, three variables are required to build the predictive model. Since the variation introduced by the preprocessing is only slightly correlated to the error in the dependent value, the accuracy of the models based on three variables is only slightly degraded. Had there been a stronger correlation between the noise variable and the error in the dependent variable, a poorer predictive model would have resulted. The CPSA algorithm (analysis [c]) effectively removes the offset even in the presence of the spectral noise, thus allowing a robust model to be built on two variables.

In the above example, the strong correlation between the offset and the dependent variable error was purposely generated to demonstrate the effect. For real systems, the extent of the correlation between possible measurement process signals and the error in the property/component values will depend strongly on the size of the database used in developing the model and the experimental design used in collecting the data. The smaller the calibration set used in developing the model, the larger the chance that a spurious correlation will be developed. For example, in case 1, the correlation between the offset and the dependent value error for the 51 calibration samples was low (r=0.000021). If the model had been developed using only the odd numbered spectra, the correlation between the offset and the dependent value error for the 26 reference spectra would be increased to 0.053. If every fifth spectrum was used, the correlation for the 11 references would be increased to 0.087, and if every 10th spectrum was used, the correlation for the 6 references would be increased to 0.41. Clearly, the smaller the sample set available for developing the model, the more important is the removal of measurement process signals in order to avoid possible spurious correlations between the measurement process signals and the dependent value errors. By removing these signals before the regression, the CPSA algorithm ensures that spurious correlations are not included in the model. The effectiveness of CPSA is limited only by the spectroscopist's ability to identify and model the possible sources of systematic measurement signals which might be present in the spectral data.

EXAMPLE 7

Removal of a Sharp Lined, Overlapping Spectral Interference

Variations in spectrometer purge during the collection of spectral data can cause the absorptions due to water vapor and carbon dioxide to be superimposed on the spectra of the samples under study. If absorption signals due to these atmospheric components are present in a calibration set, Principal Components due to these signals will be detected and possibly incorporated into the predictive models. The prediction of properties/components for unknowns will then potentially be dependent on the quality of the spectrometer purge. For Mid-IR, preprocessing algorithms base on subtraction of a water vapor or carbon dioxide spectra can sometimes be employed providing the overlap between the absorptions of the atmospheric components and the sample are not too great. For Near-IR, the overlap between the absorptions due to water vapor and hydrocarbon combination bands generally precludes the use of such preprocessing. By using a correction spectra of the atmospheric component to develop a constraint, the CPSA algorithm can remove the effect of the atmospheric components even when their absorptions strongly overlap those due to the sample components.

Figure 11:
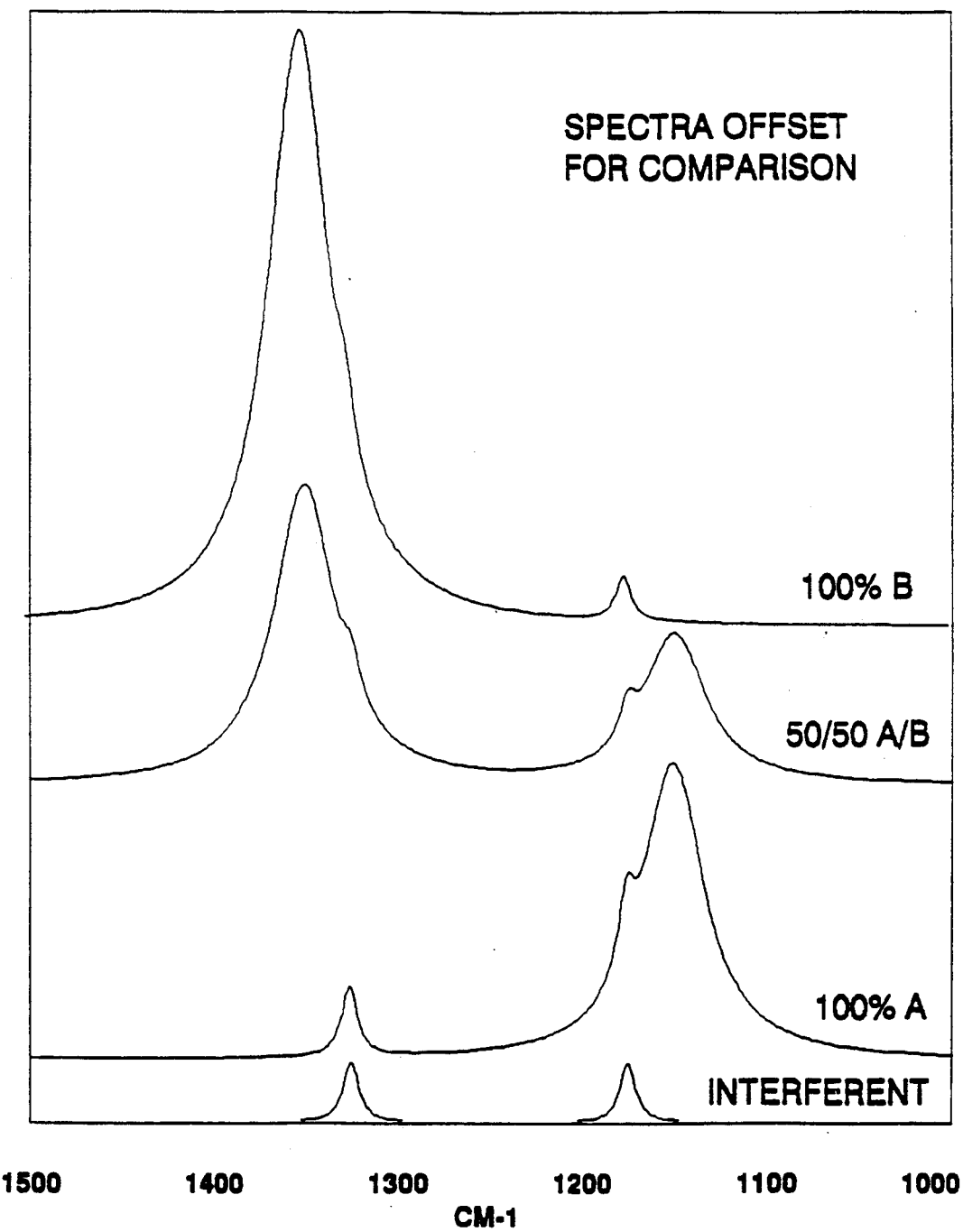
Figure 13B:
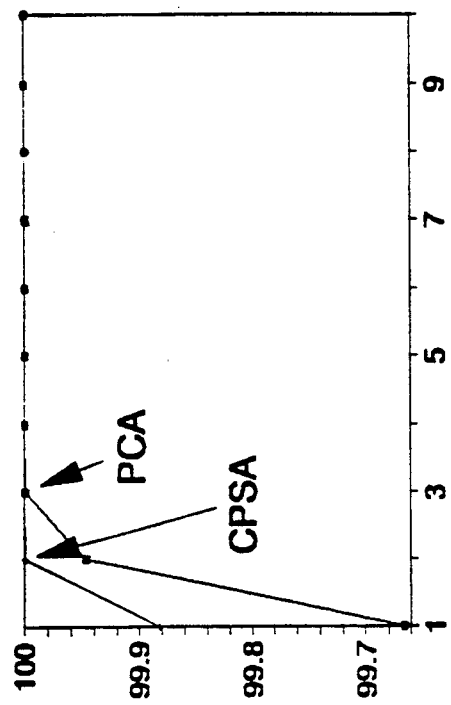
Figure 13D:
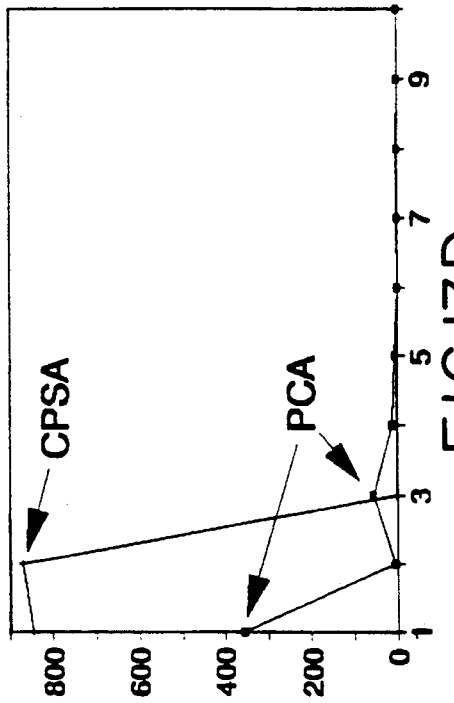
Figure 13A:
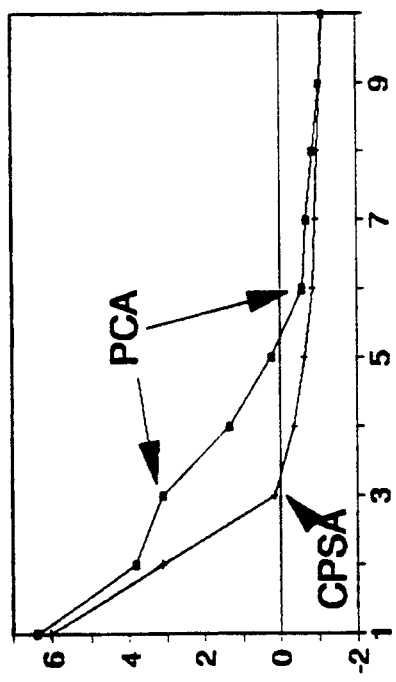
Figure 13C:
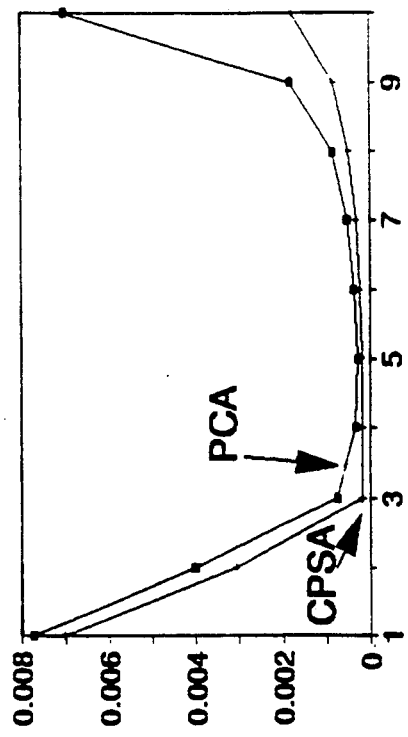

To illustrate the use of the CPSA algorithm to develop constraints for these types of spectral interferences, an additional series of synthetic spectra were generated. A interference component spectrum was generated as the sum of two Lorenztian bands at 1325 and 1175 cm$^{-1}$, both having a half band width at half maximum of 5 cm$^{-1}$ and a height of 0.1 absorbance unit. The spectrum of the interference component was randomly scaled and added to the mixture spectra in data set [1] above. FIG. 11 shows examples of the spectra which were generated. The overlap between the absorptions of the interference component and the absorptions of components A and B was purposely chosen such that the removal of the interference by spectral subtraction would be difficult to impossible. FIG. 12 shows the statistics for a Principal Components Analysis (analysis [a]) of these spectra. Three spectral variables are indicated by all of the statistics. All three variables are required to produce a predictive model with 0 standard error, the use of the first two Principal Components to develop a predictive model resulting in standard errors of 0.6. Again, as in Example 1 above, when the extra variable is include in the model, the possibility exists that a correlation between the level of the interference component and the dependent variable or error in the dependent values will be incorporated into the model, reducing the robustness of predictions.

By supplying the CPSA algorithm with the spectrum of the interference component, a constraint can be developed. FIG. 12 also shows the statistics for the CPSA analysis of the synthetic spectra. The use of the constraint reduces the number of spectral variables to 2, and a model based on these variables predicts the component A concentrations with 0 standard error. Since the variation due to the interference component is removed prior to the regression, no correlation between the level of the interference and the dependent values/errors can be erroneously incorporated into the predictive model. The robust predictive model is thus insensitive to the presence of the spectral interference.

EXAMPLE 8

Binary Blends of Isooctane and Heptane

The first example demonstrates how a Constrained Principal Components Analysis can be used to develop a model that is robust relative to variations in signals arising from the spectral measurement process. Mid-infrared (4000–400 cm$^{-1}$) spectra of 22 binary mixtures of isooctane (2,2,4-trimethyl pentane) and n-heptane were collected on a Mattson Polaris/Icon FT-IR spectrometer at 2 cm$^{-1}$ resolution, using 100 scans for signal averaging and a 25 micron potassium bromide fixed pathlength cell. The single beam sample spectra were ratioed against empty beam background spectra for the calculation of the absorbance spectra. Principal Components Analysis and Constrained Principal Components Analysis were both used to generate models for the estimation of the isooctane and heptane contents of the binary mixtures. To avoid absorbances that might be outside the linear response range of the spectrometer, only the data in the 2000–690 cm$^{-1}$ spectral range were used in the models. The spectra of 11 of the binary mixtures were used in developing the models, and the spectra of the remaining 11 mixtures were used to test the models. The concentrations of the mixtures used for generating and testing the models are given in Table 6.

Figure 14A:
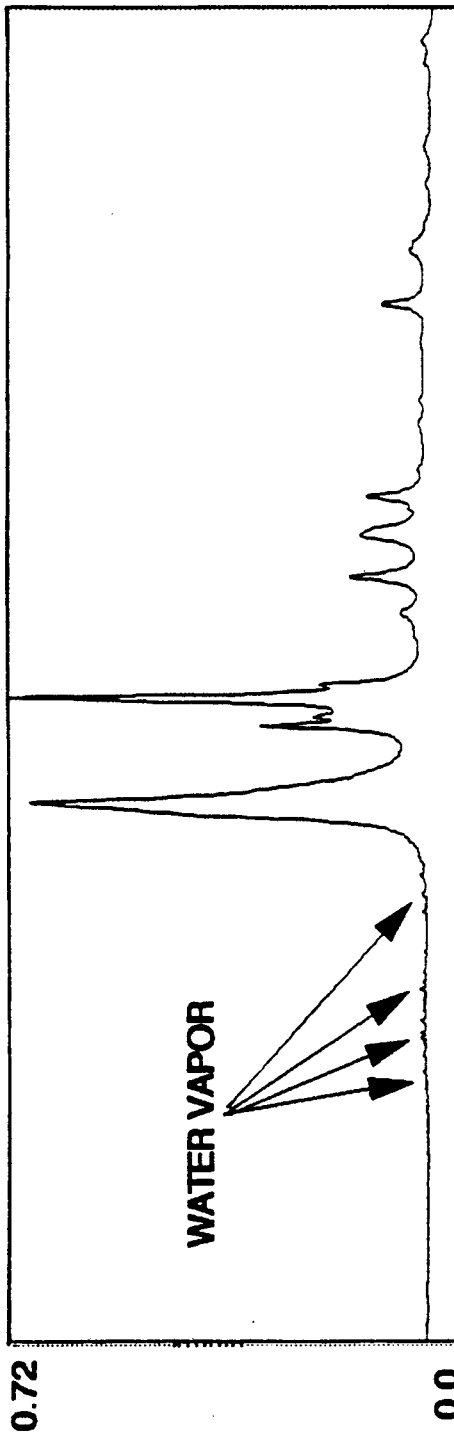
Figure 14B:
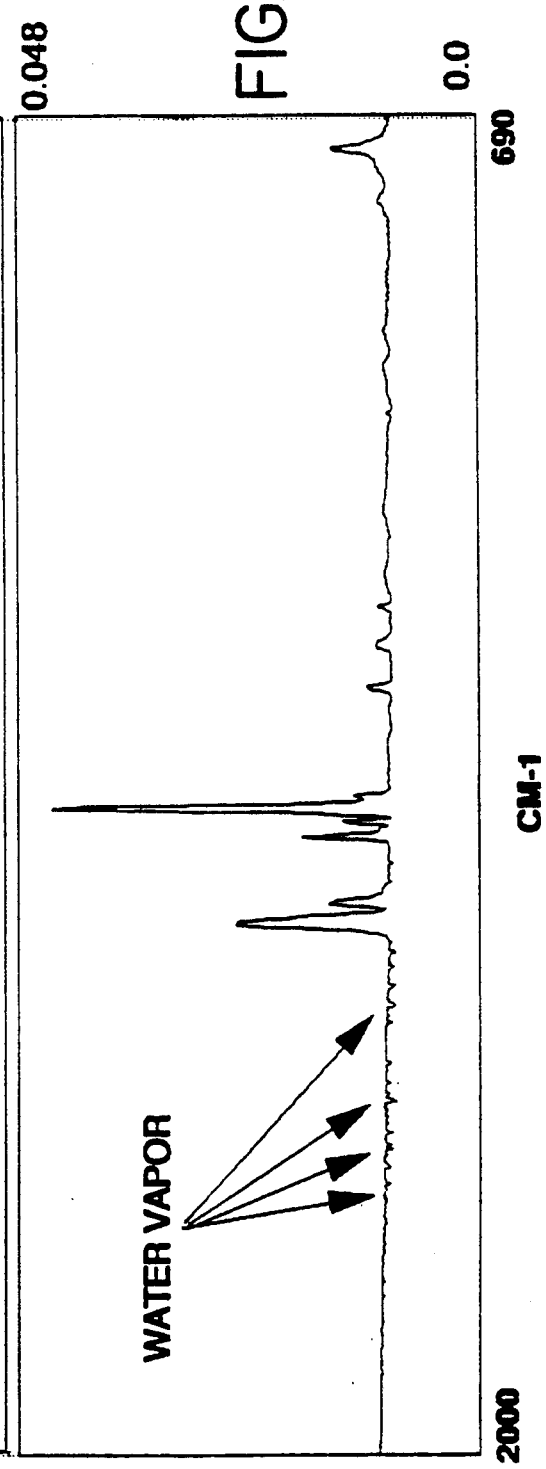

FIG. 13 shows the statistics for the Principal Components Analysis (PCA) of the blend spectra. As is typical with real systems, the various statistical tests do not unambiguously indicate the true number of spectral variables. The plot of the logarithm of the eigenvalues versus number of Principal Components decreases relatively smoothly, showing only minor breaks at 3 and 6 Principal Components. The indicator function goes through a minimum at 5 variables, the cumulative variance appear to level off after 3 Principal Components, and the eigenvalue ratios have maxima at 1 and 3 Principal Components. None of the statistics indicates the true number of real components in the binary blends. Examination of the average and standard deviation spectra for the calibration spectra (FIG. 14) suggests the sources of these additional spectral variables. There is clearly a frequency dependent variation in the spectral baseline as well as absorptions due to water vapor due to incomplete spectrometer purge. Examination of the eigenspectra produced by the PCA analysis (FIG. 15) demonstrates how these additional measurement related variations are extracted as Principal Components. Eigenspectrum 1 shows the absorptions due to the two real components, but is clearly offset relative to the zero absorption. Eigenspectrum 2 shows only slight differentiation between the isooctane and heptane absorptions, and is dominated by an offset. Eigenspectra 3 and 4 differentiate between the two real components, but also show a frequency dependent variation in the spectral background. Eigenspectrum 5 is clearly that of water vapor. Eigenspectrum 6 is largely measurement noise. Note that the measurement process related signals are not cleanly extracted into single Principal Components, but are mixed among all the spectral variables. The offset is clearly present in both Eigenspectra 1 and 2. Water vapor absorptions are observed in Eigenspectra 1,2,4 and 5, and the frequency dependent background is present in Eigenspectra 3 and 4.

Figure 16:
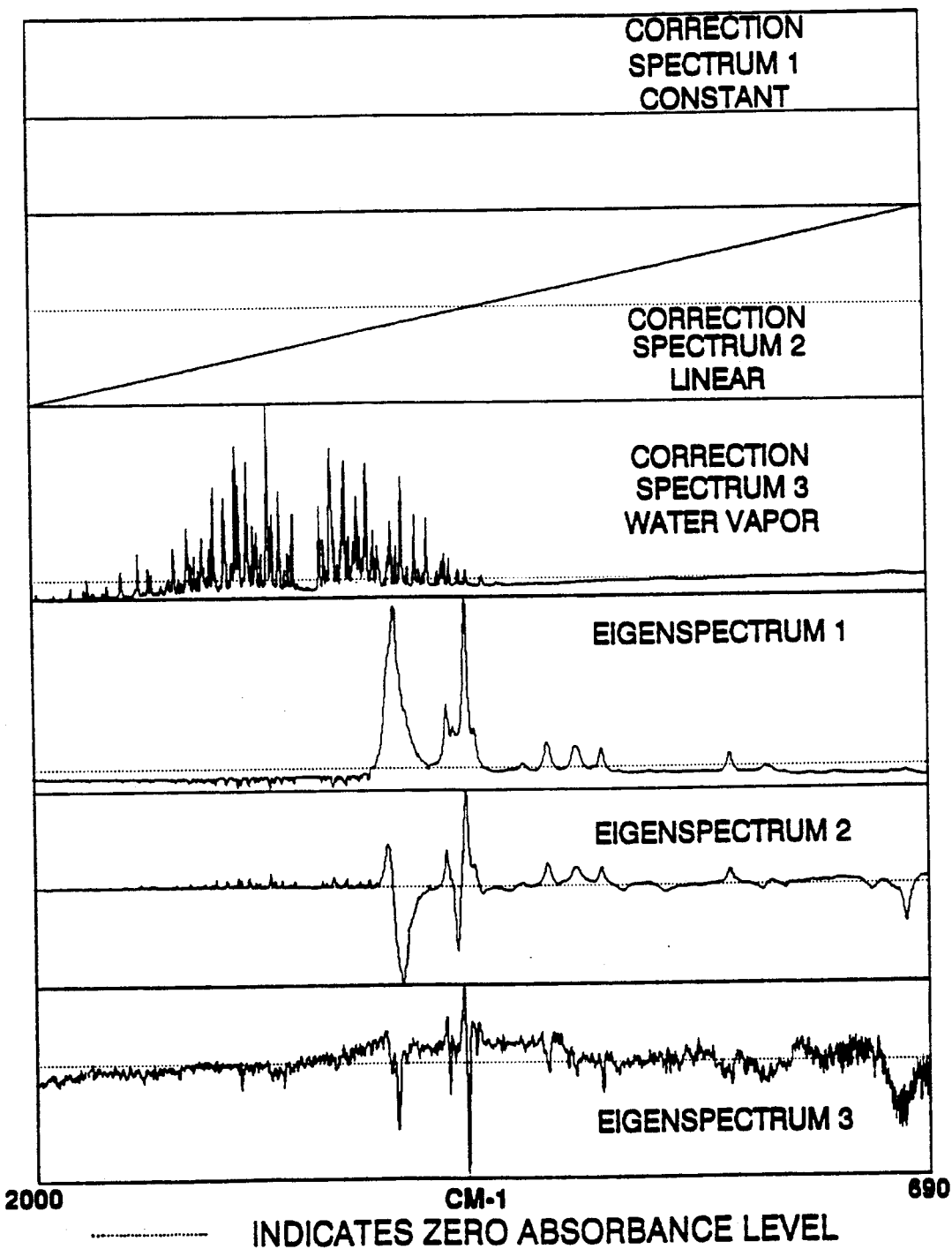

A CPSA model was developed for the same data set, using a second order (constant plus linear) polynomial background correction and water vapor correction spectra as constraints. FIG. 16 shows the three correction spectra used, as well as the first three eigenspectra generated by the CPSA analysis. The eigenspectra are now orthogonal to an offset, a linear frequency dependent background and the water vapor correction spectra. The third eigenspectra consists almost exclusively of noise, indicating that the isooctane and heptane spectral variation has been successfully extracted into two spectral variables.

Figure 17:
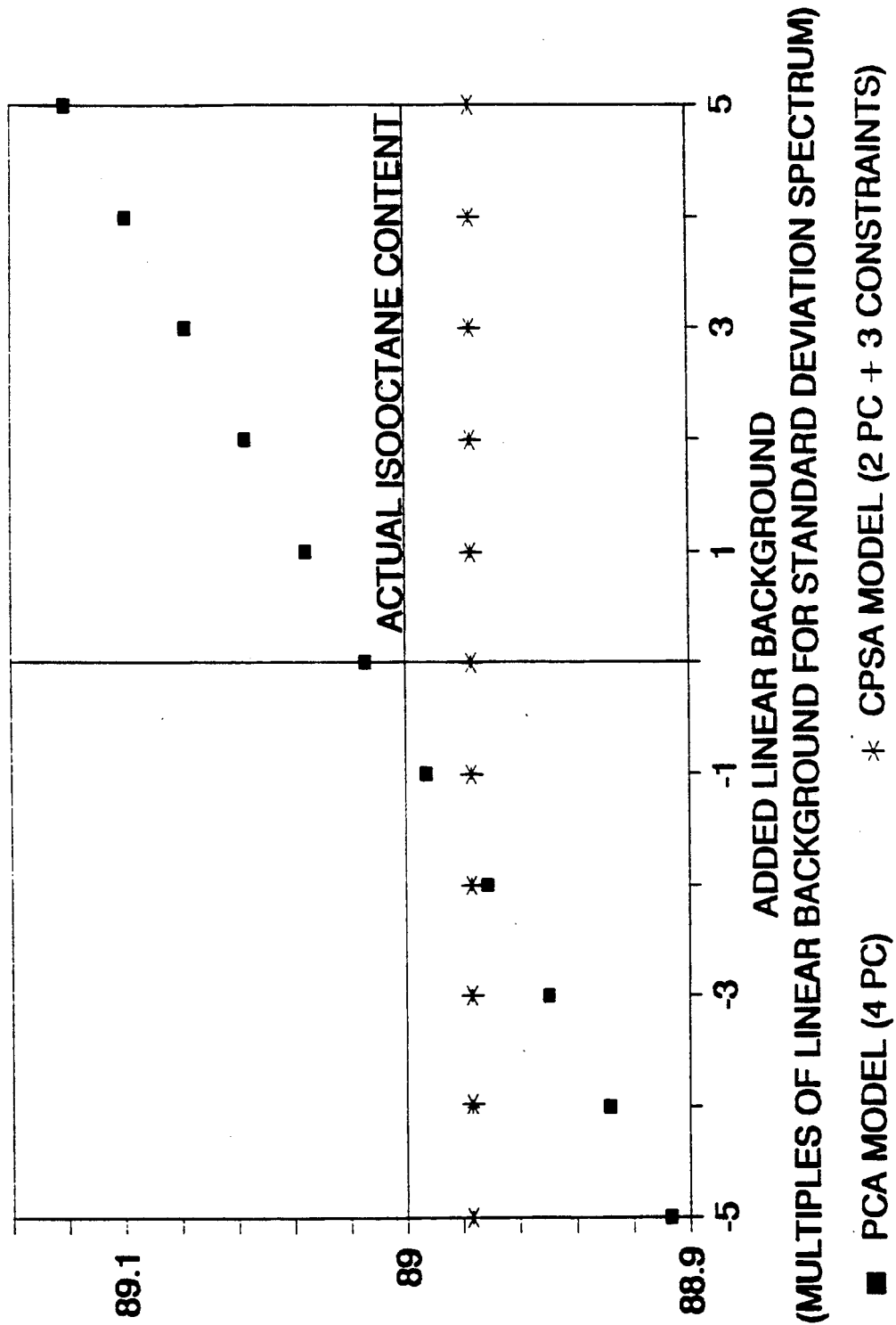

Table 7 shows the Standard Errors for the PCA and CPSA models. As would be expected from the eigenspectra, the PCA model requires 4 variables to account for the variation in the isooctane and heptane concentrations. Inclusion of the fifth Principal Component in the PCA model appears to produce a slight improvement in the Standard Error of Estimate from the calibration, but actually produces a slight degradation of the predictive model. The CPSA model based on two variables has predictive power comparable to the PCA model with 4 variables, but is more robust with respect to the measurement process signals which are present in the spectral data. FIG. 17 demonstrates this improved robustness. The variability in the background among the calibration samples was estimated by fitting a linear baseline to the standard deviation spectrum in FIG. 14 (calculating the slope and intercept of the line connecting the two endpoints at 2000 and 690 cm$^{-1}$). Multiples of this estimated background were then added to the spectrum of the sample containing 89% isooctane, and the generated spectra were analyzed using the 4 variable PCA model and the 2 variable CPSA model. For the PCA model, the predicted isooctane content clearly depends on the background. Over the range of backgrounds present in the spectral data, variations on the order of 0.05% are observed. If, in the analysis of an unknown, a larger difference in background was present in the spectra, errors on the order of 0.1% could easily be obtained. The CPSA model is independent of the variation in background and produces the same results regardless of the change in background. CPSA thus provides a more robust and stable predictive model.

The major source of error for both the PCR and CPCR analyses is the fact that the sum of the two components does not equal 100%. As is shown in Table 7, if the estimated isooctane and n-heptane concentrations are renormalized to 100%, the SEEs and SEPs are significantly reduced. Even after renormalization, 4 variables are required to produce a PCR model comparable to the 2 variable CPCR model. It should be noted that, as is shown in Table 7, if the pathlength correction (which was described in Section 3.0 of the appendix) is used in developing the PCR and CPCR models, the renormalization of the estimated isooctane and n-heptane concentrations results automatically from the constraint that the sample components must sum to 100%.

EXAMPLE 9

Analysis of a 5 Component Additive Package

Comparison to the K Matrix Method

We have previously demonstrated the use of the K Matrix method for the quality control analysis of a oil additive package. In the K Matrix analysis, the calibration f by n spectral matrix, X, is expressed as the product of two matrices, K and C.

$$X = KC$$

C is a c by n matrix containing the concentrations of the c real components for the n calibration samples. The f by c K matrix is obtained as $$K = XC^t(CC^t)^{-1}$$

K contains the spectra of the real components as they exist in the calibration mixture, i.e. including any inter-component interactions. The K matrix obtained in the calibration can be used in the analysis of a unknown, x, to obtain the component concentrations, c $$c = (K^tK)^{-1}K^tx$$

Unlike the Principal Component methods, the use of the K Matrix method requires that the concentrations of all the components in the mixtures be known such that the C matrix which must be inverted completely specifies the calibration mixtures.

Figure 18:
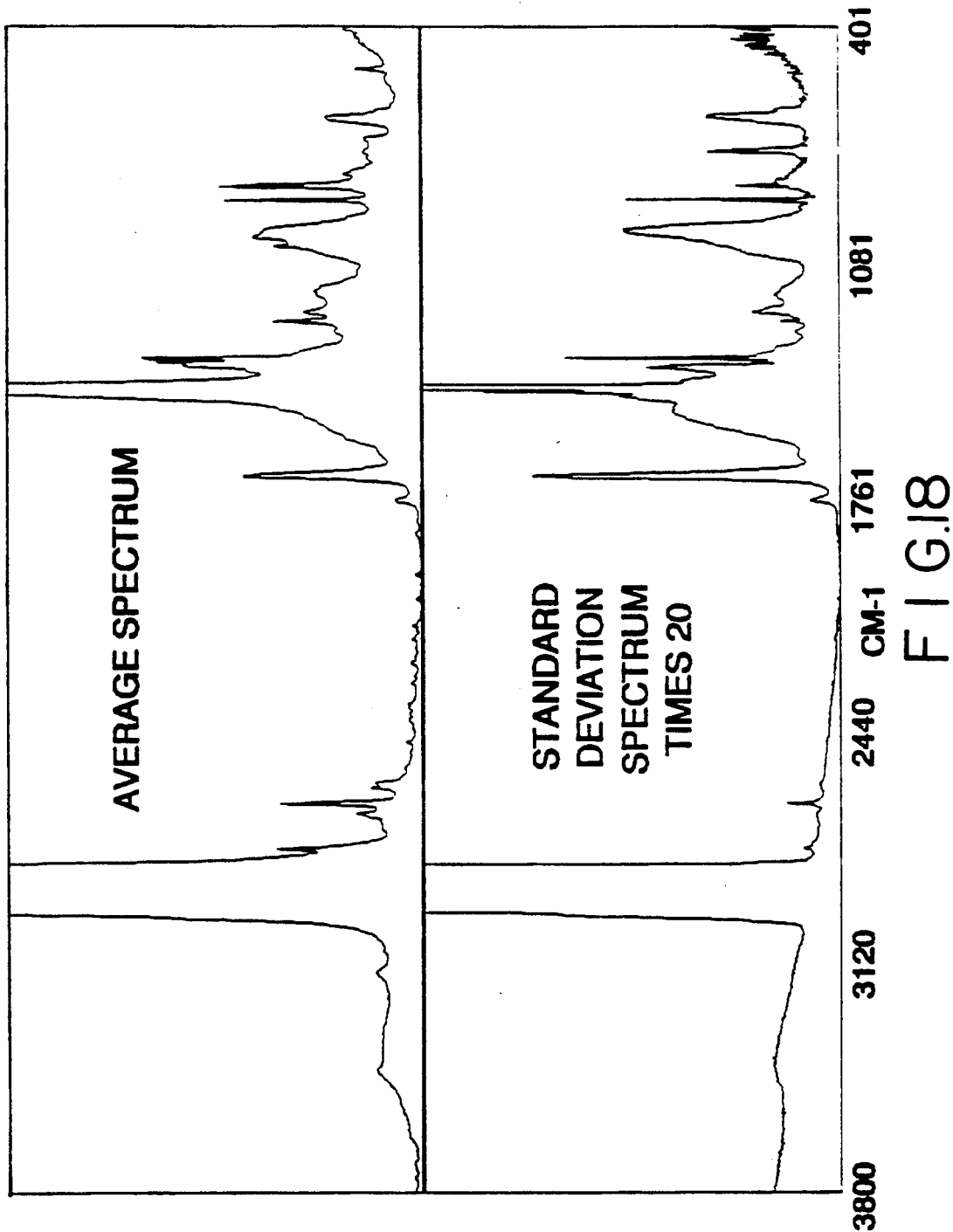
Figure 19B:
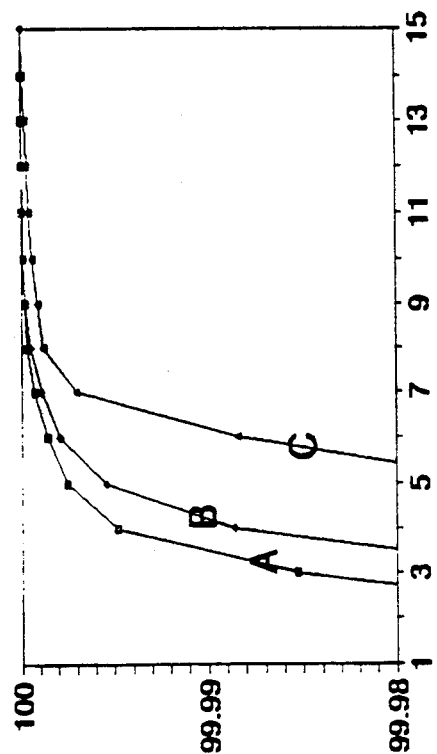
FIGS. 19A-19D are statistics for analysis of add pack blends, the abscissa and ordinate for FIGS. 19A, 19B, 19C, and 19D being the same as in FIG. 7.
Figure 19D:
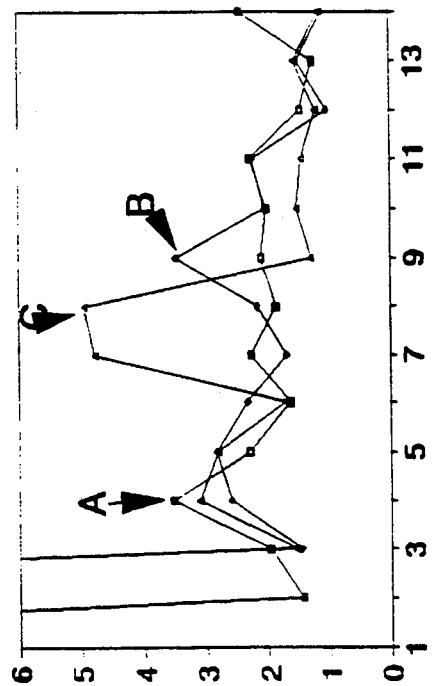
Figure 19A:
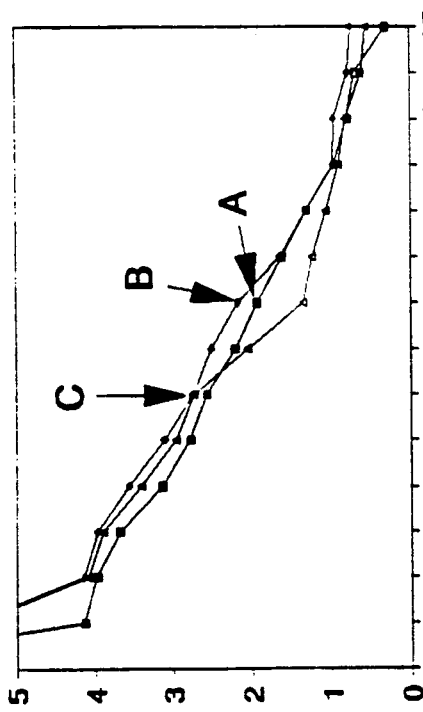
Figure 19C:
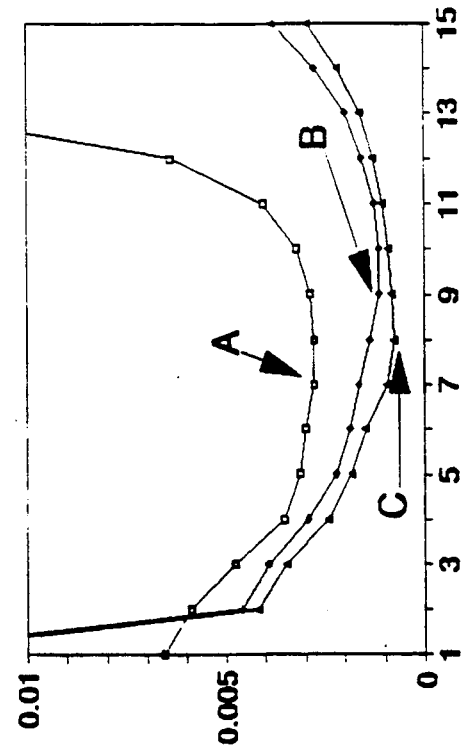

To further demonstrate how CPSA can be used to develop a calibration for a real multicomponent analysis, a more detailed description of the analysis presented in Example 5 will be given to demonstrate how a predictive model was developed using the same spectral data which had been used for the K Matrix analysis. The additive package in question contains five components: a dispersant (49%), a nonyl phenol (NPS, 16%), a zinc dialkyl-dithiophosphate (ZDDP, 15%) a magnesium overbased sulfonate (12%) and a diluent oil (8%). For the quality control applications, the calibration was developed over a relatively narrow concentration range bracketing the target product composition. 30 blends were prepared by blending the 4 additives at levels corresponding to 88%, 92%, 100%, 108% or 112% of the target concentrations, and adjusting the diluent oil level to achieve the appropriate total weight. The levels for additives in the individual blends were chosen randomly subject to the constraints that the number of times each additive level was represented should be roughly equal, and that all the components vary independently. Spectra of 50% solutions of the blends in cyclohexane were obtained at 2 cm$^{-1}$ resolution using a 0.05 millimeter KBr cell on a Digilab FTS-20C FT-IR spectrometer using 500 scans for signal averaging. 15 of the 30 blends which spanned the additive concentration ranges were chosen for development of the models and the remaining 15 were analyzed to test the models. FIG. 18 shows the average and standard deviation spectra for the 30 blends. Spectral data in the range from 1800 to 490 cm$^{-1}$ was used in the analysis. To avoid absorbances that are too strong to accurately measure, the data in the range from 1475 to 1435 cm$^{-1}$ was excluded from the analysis.

Figure 20:
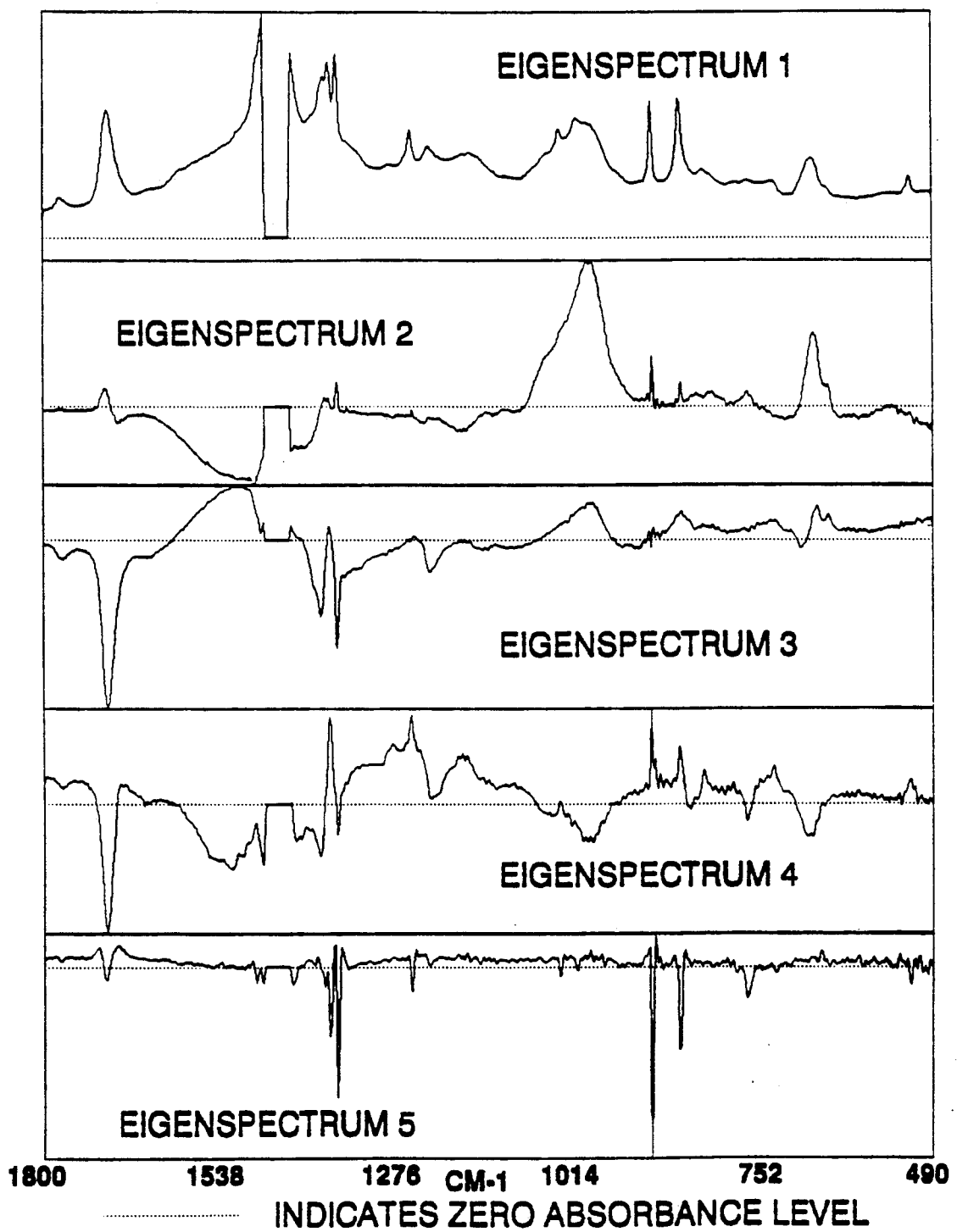
Figure 21:
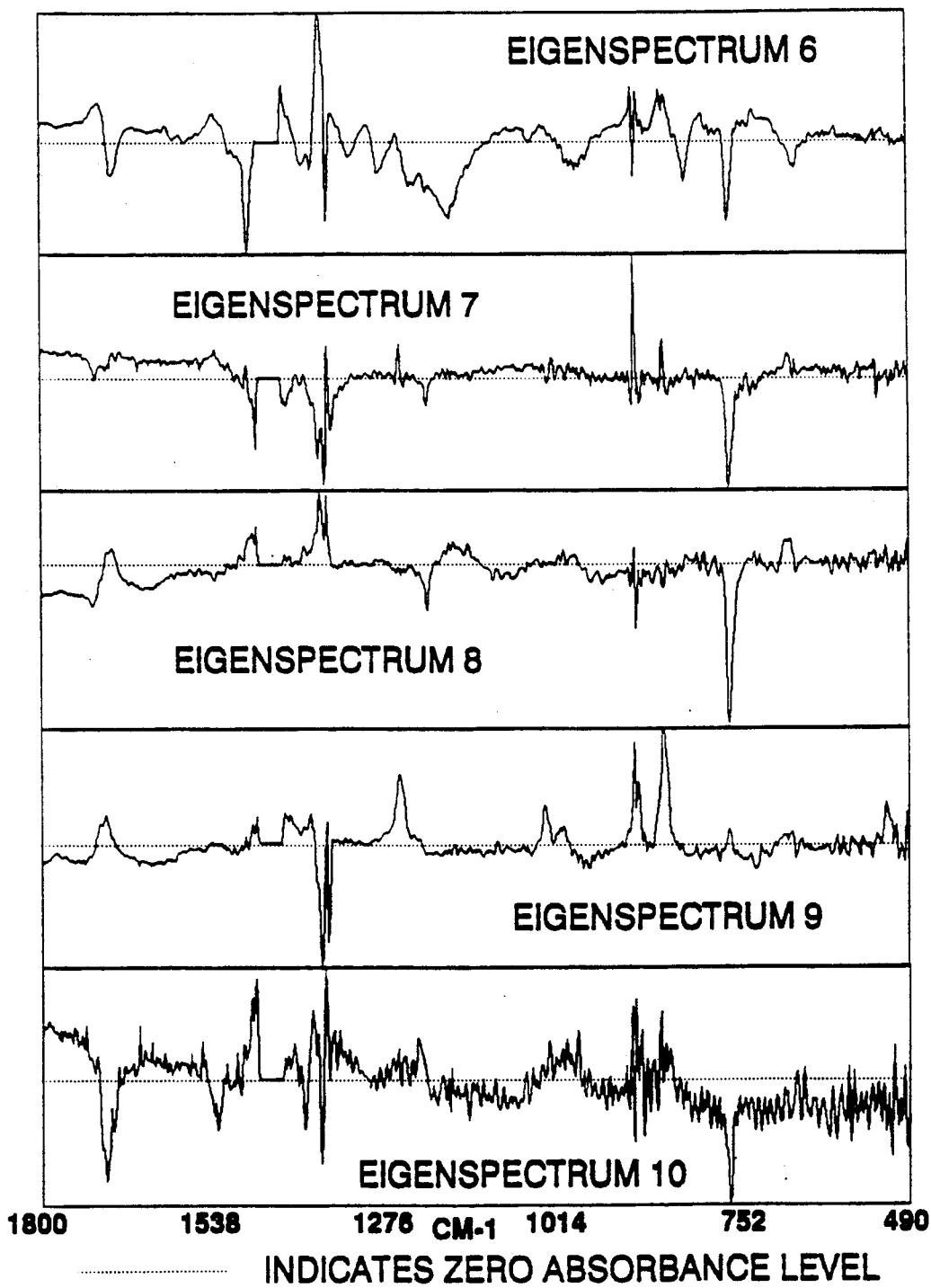
Figure 22:
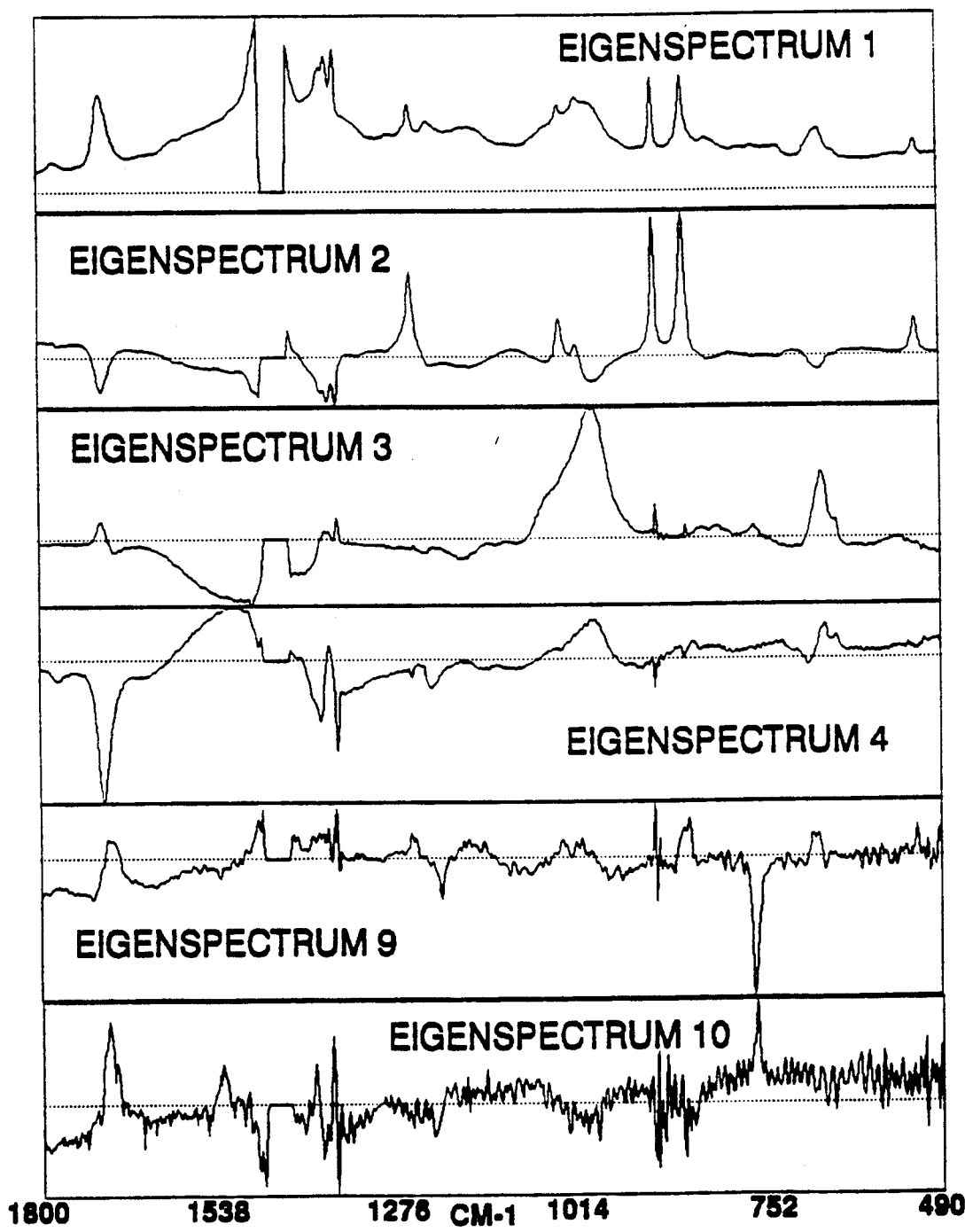

To evaluate what possible measurement process signals might be present in the spectral data of the calibration blends, a Principal Components Analysis was conducted on the 15 spectra. FIG. 19 shows the statistics for the PCA calculation. The various statistical tests do not clearly indicate or agree on the number of variables present in the spectral data, although most of the tests suggest that there are more variables than real components. FIGS. 20 and 21 show the first 10 eigenspectra obtained for the PCA calculation. Clearly, at least the first 9 eigenspectra contain recognizable absorption bands which are well above the spectral noise level. Examination of the eigenspectra and the standard deviation spectrum indicate the sources of the additional spectral variables. Eigenspectra 8 shows negative bands at 1215 and 761 cm$^{-1}$ which are due to chloroform contamination of the solutions, chloroform having been used to rinse the cell between samples. The standard deviation spectrum (FIG. 18) shows a strongly curved background, suggesting that background variations may also be contributing the spectral variance. Unlike previous examples, the contributions of the background to the spectral variables are not as obvious from the eigenspectra, but are mixed with the variations due to the real component absorptions. Together, the chloroform and the background could account for two of the nine spectral variables. Eigenspectra 5 and 9 both show features due to the cyclohexane solvent. In eigenspectrum 5, the bands have a dispersive shape suggestive of a variation in bandwidth among the calibration spectra. Close examination of the calibration spectra indicates that the cyclohexane absorptions do vary slightly in bandwidth, presumably because of variations in the strength of interactions with the additives. Eigenspectrum 9, on the other hand, shows normally shaped features corresponding to the solvent. If the solutions had all been prepared to exactly the same concentration, and if no solvent/additive interactions were present, the spectral features due to the cyclohexane would have been constant among all the blends, would have been observed exclusively in eigenspectrum 1, and would not have been detected as a separate spectral variable. In reality, the solvent contributes two spectral variables, eigenspectrum 5 arising from variations in the solute/solvent interactions, and eigenspectrum 8 arising from variations in the solute/solvent concentrations. To verify that this is the case, a second PCA analysis was conducted using the 15 calibration blends plus 3 spectra of cyclohexane obtained under the same conditions. FIG. 22 shows some of the eigenspectra obtained from this analysis. In the PCA calculation using only the blend spectra, the variation in the solvent concentration was small, and showed up only as the 9$^{th}$ most important spectral variable (FIG. 21). Adding the spectra of the solvent to the reference set dramatically increases the range of variation in the solvent absorptions, making it the 2$^{nd}$ most important spectral variable. Aside from the noise level, eigenspectrum 2 in FIG. 22 very closely resembles the eigenspectrum 9 in FIG. 21. If solvent concentration variation was not a spectral variable in the original 15 calibration spectra, then the inclusion of the solvent spectra would have added an additional variable to the data. Comparison of FIGS. 20 and 21 to FIG. 22 clearly indicates that this is not the case. The inclusion of the solvent spectra has reordered the 9 variables (e.g. eigenspectrum 2 in FIG. 20 becomes eigenspectrum 3 in FIG. 21), but the 10$^{th}$ eigenspectrum in both cases shows minimal absorption features above the spectral noise level.

Figure 23:
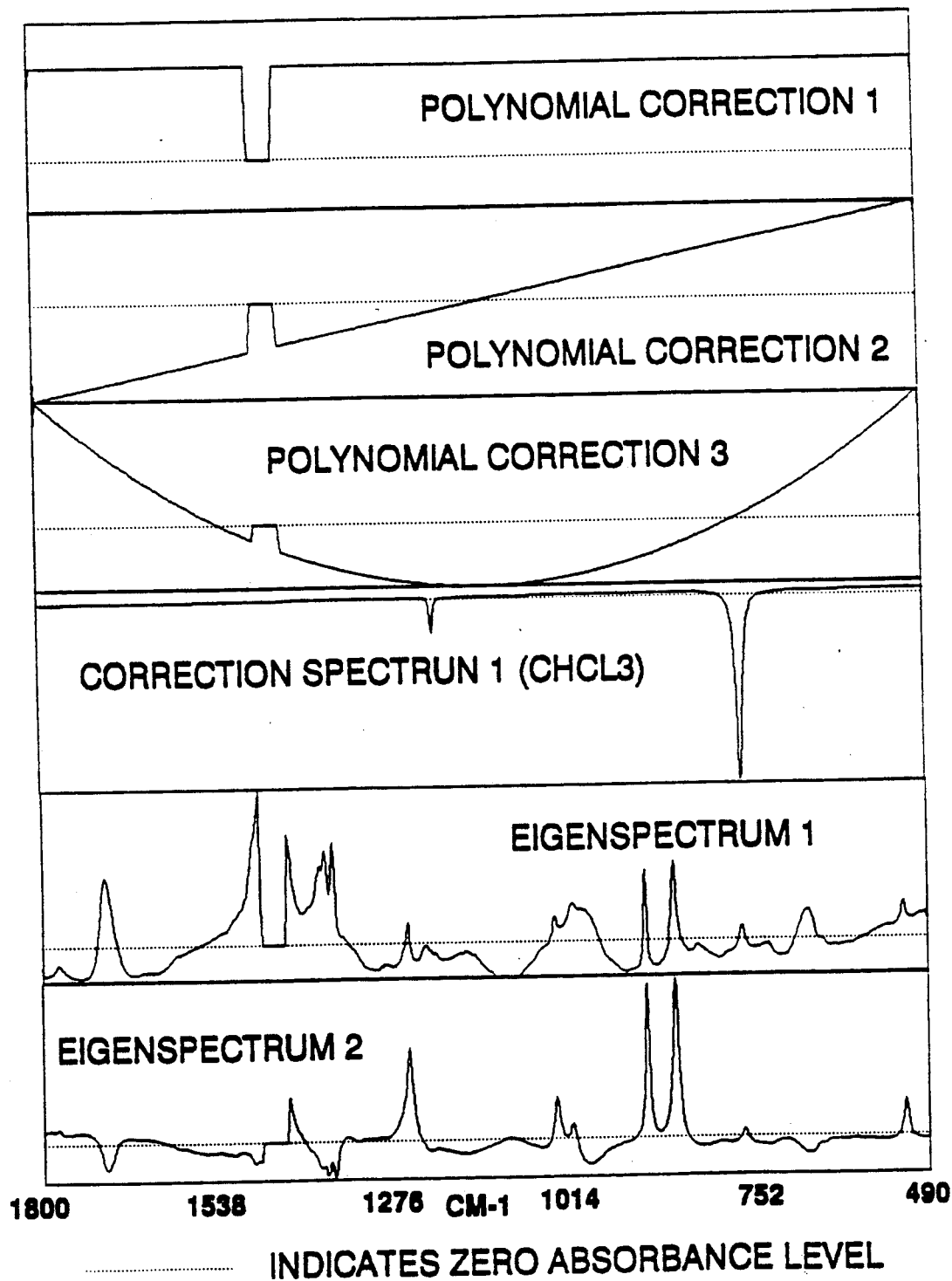
Figure 24:
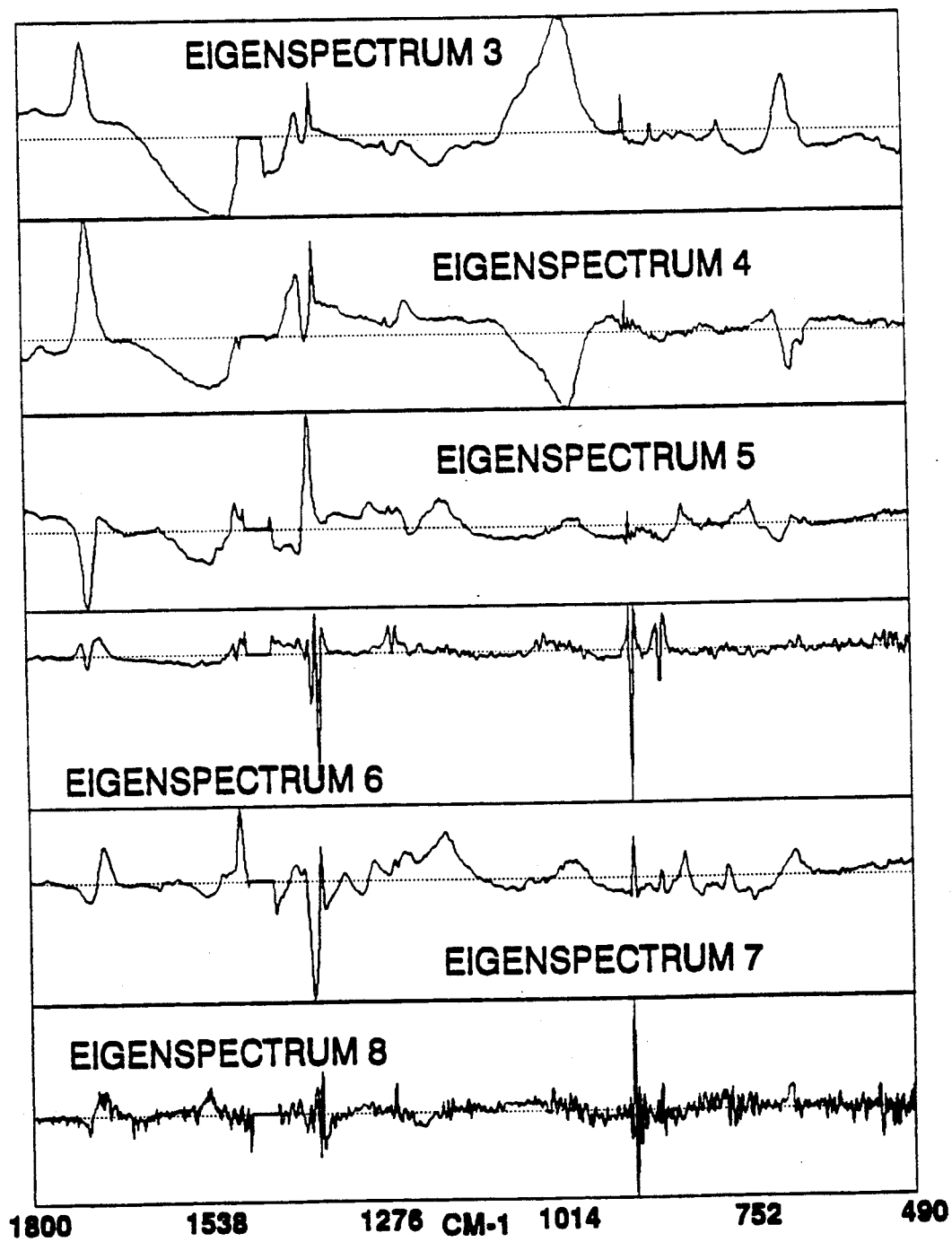

The above analysis indicates that 7 of the 9 spectral variables correspond to sample variations, 5 due to additive package components, 1 due to variations in the cyclohexane solvent concentration, and 1 due to variations in the solvent/solute interactions. The remaining 2 variables are due to the measurement process, and correspond to background fluctuations and chloroform contamination. Using this information, a CPSA model can be constructed. Since the solvent concentration variation is a variable in the spectra of the blends, the solvent spectra were included in the reference set for the generation of the CPSA model so as to ensure that the solvent variation could be properly modeled. FIGS. 23 and 24 show the various correction spectra which are used, as well as the resulting eigenspectra. A 3 term (quadratic) correction is used to account for the possible background variation. Although the chloroform is actually in the sample, it is at a low enough level so as not to cause significant dilution of the sample absorptions, and thus can be treated as a measurement process variable rather than a sample component. Since the chloroform absorptions observed in PCA eigenspectra 8 are shifted slightly from those observed for neat chloroform, a synthetic chloroform spectrum was generated for use as a correction spectrum by fitting the observed absorptions to Lorenztian bands. CPSA eigenspectrum 7 (FIG. 23) appears to be roughly equivalent to PCA eigenspectrum 10 (FIGS. 21 and 22) in terms of the signal to noise of the residual absorption features. By including the 4 constraints, the CPSA model allows the spectral variance to be accounted for in 7 variables rather than the 9 required by the PCA analysis.

Table 8 shows the Standard Errors for the K Matrix, PCA and CPSA models. Since there are only 6 components (5 add pack components plus cyclohexane) in the samples, the K Matrix method can only extract 6 variables. The K Matrix model cannot account for the solute/solvent interactions and thus produces a poorer predictive model than the Principal Component methods which allow this interaction to be modeled as a separate variable. The Standard Error of Estimate is lower for the PCA model based on 9 variables than the CPSA model based on 7, because the two extra variable that correspond to measurement process signals are being correlated to the dependent variable. If, for instance, we use the PCA model to analyze the 4 constraint spectra used for the CPSA model (the first 4 spectra in FIG. 23), we see (Table 9) that predictions made with the PCA model will depend on background and chloroform contamination, and will not be robust relative to these measurement process signals. When the PCA and CPSA models are used to analyze the 15 test blends (Table 8, bottom), it can be seen that the predictive capability of the more robust CPSA model based on 7 variables actually exceeds that of the PCA model based on 9 variables.

For simplicity, since no water vapor absorptions were observed in the standard deviation spectra or the PCA eigenspectra, a water vapor constraint was not added in the development of the above CPSA model. If this model was to be used in actual quality control applications, a water vapor constraint would be added to insure that the results were not affected by the instrument purge. As is seen in Table 8, the addition of water vapor correction spectra to the model so as to improve its stability and robustness does not effect the accuracy of the predictions for the 15 test spectra which showed no water vapor absorptions.

EXAMPLE 10

Example 10 is intended to demonstrate how a Constrained Spectral Analysis can be employed to remove a signal arising from the measurement process in a real application. A CPCR model was developed to estimate the research octane number (RON) of powerformate samples. Laboratory data was collected over the 870 to 1600 namometer range for 186 reference powerformate samples using a LTI Industries Quantum 1200 Near-Infrared Analyzer. RON values for the powerformate reference samples were obtained via ASTM-2699. A CPCR model was developed using 3 polynomial correction spectra (constant, linear and quadratic polynomials), and 5 Constrained Principal Component variables. The Standard Error of Estimate for the model was 0.30 research octane numbers.

Figure 26:
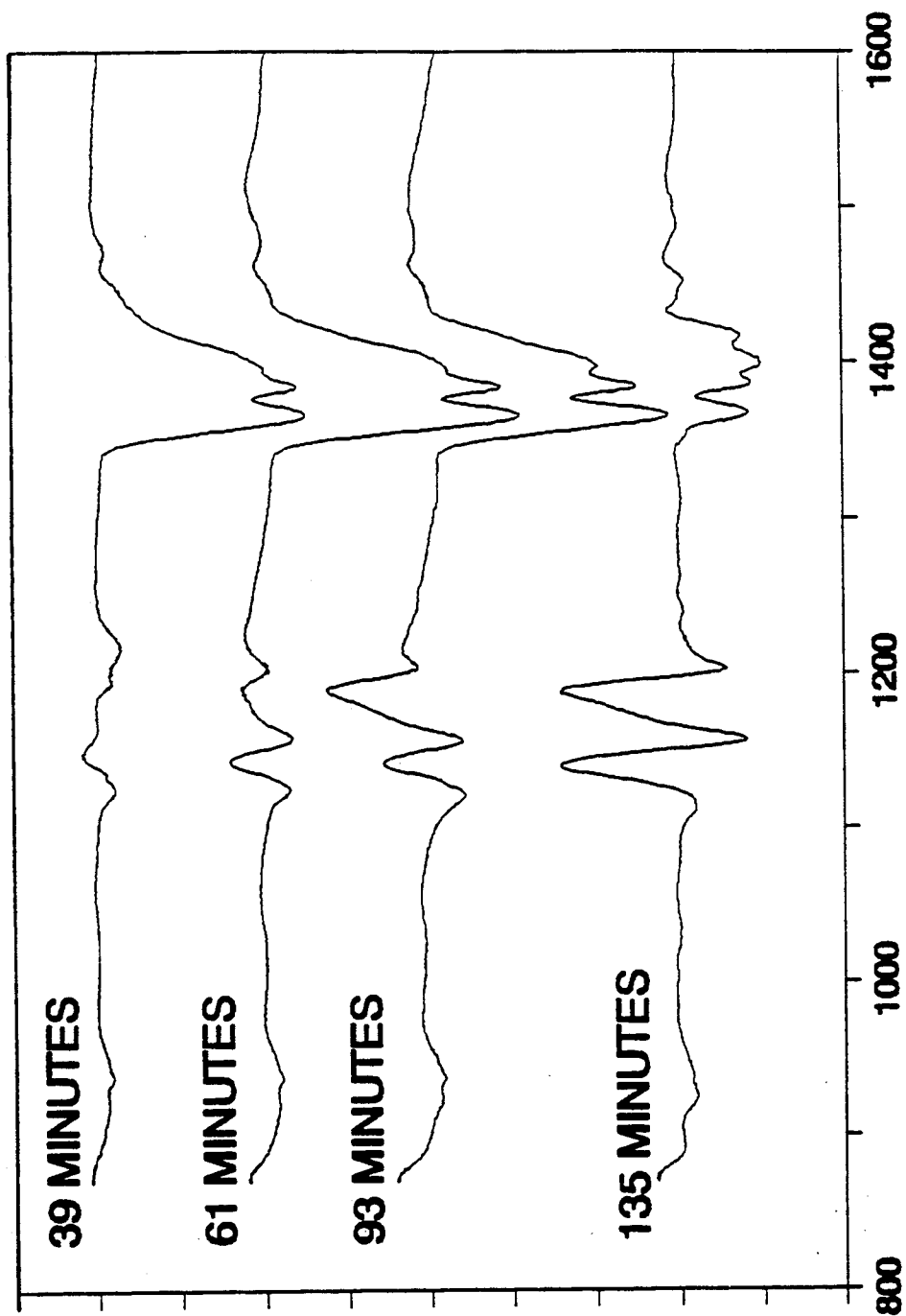
Figure 27:
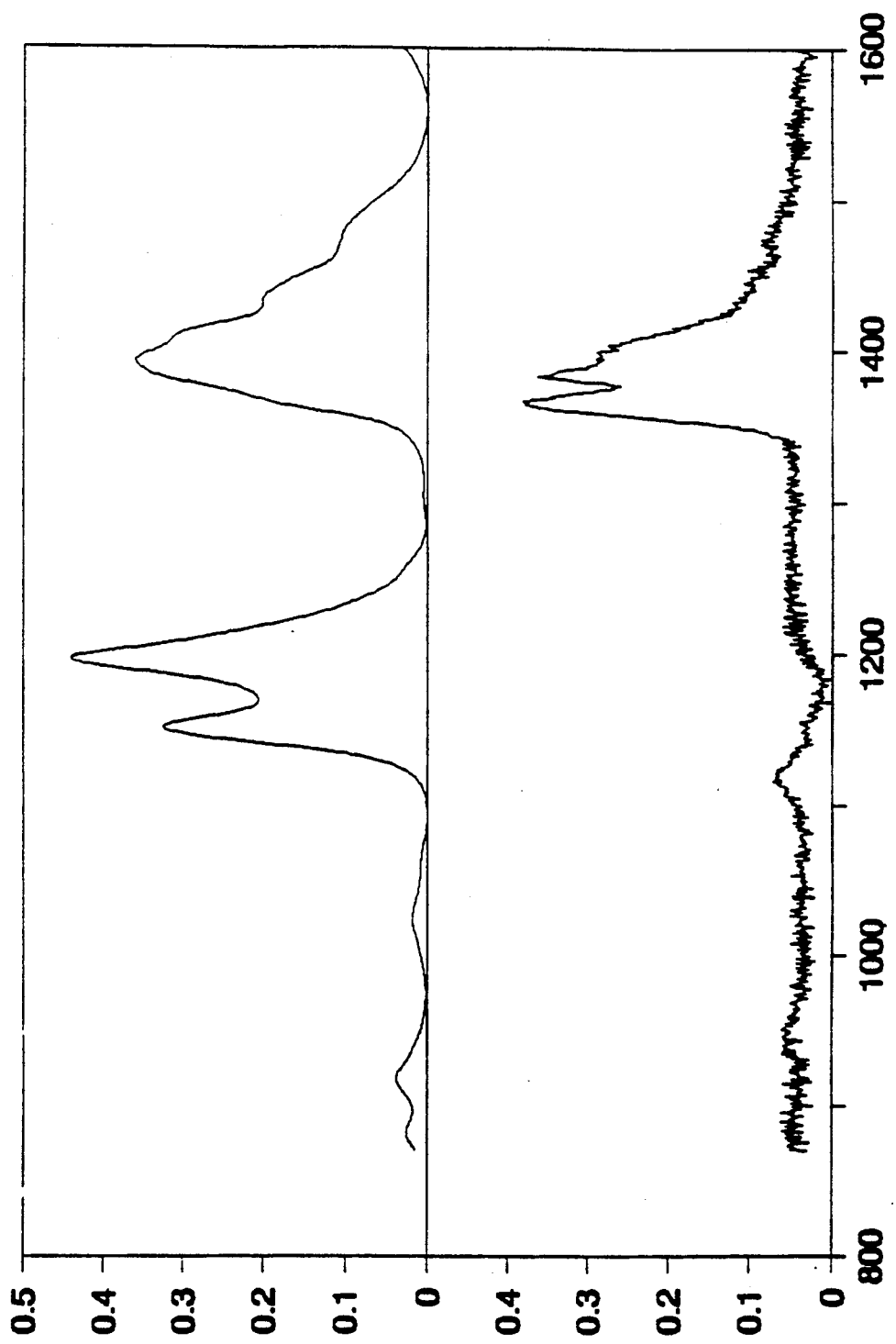

In testing the viability of using Near-Infrared for the measurement of on-line research octane number, the laboratory analyzer was equiped with a flow cell, and connected to a fast sampling loop from a powerforming unit. Spectra of the powerforming product were collected at approximately 6 minute intervals using the same conditions as were used for the collection of the reference spectra. The resultant estimate of the research octane number (FIG. 25) showed a periodic oscillation at a frequency which was much more rapid than expected changes in the product composition. By subtracting successive spectra (FIG. 26), it was established that the oscillation was due to a periodic variation in the absorption the range of 1400 nanometers. The absorption was identified as being due to atmospheric water vapor (FIG. 27) which was present in the instrument light path, and the oscillation was tracked to the cycle time of an air conditioning unit present in the instrument shake where the analyzer was located. From FIG. 26, it is clear that the for short time periods (<40 minutes), there were only minor changes in the powerformate product composition, and the periodic changes in the estimated RON where due solely to the variations in the humidity in the instrument. Difference spectra generated over longer time intervals (e.g. 93-135 minutes) demonstrated that the magnitude of the water vapor absorption was comparable to the differences in absorption due to actual compositional changes. From FIG. 27, it can be seen that the water vapor absorption falls within the same spectral range as absorptions due to the powerformat hydrocarbons.

Figure 28:
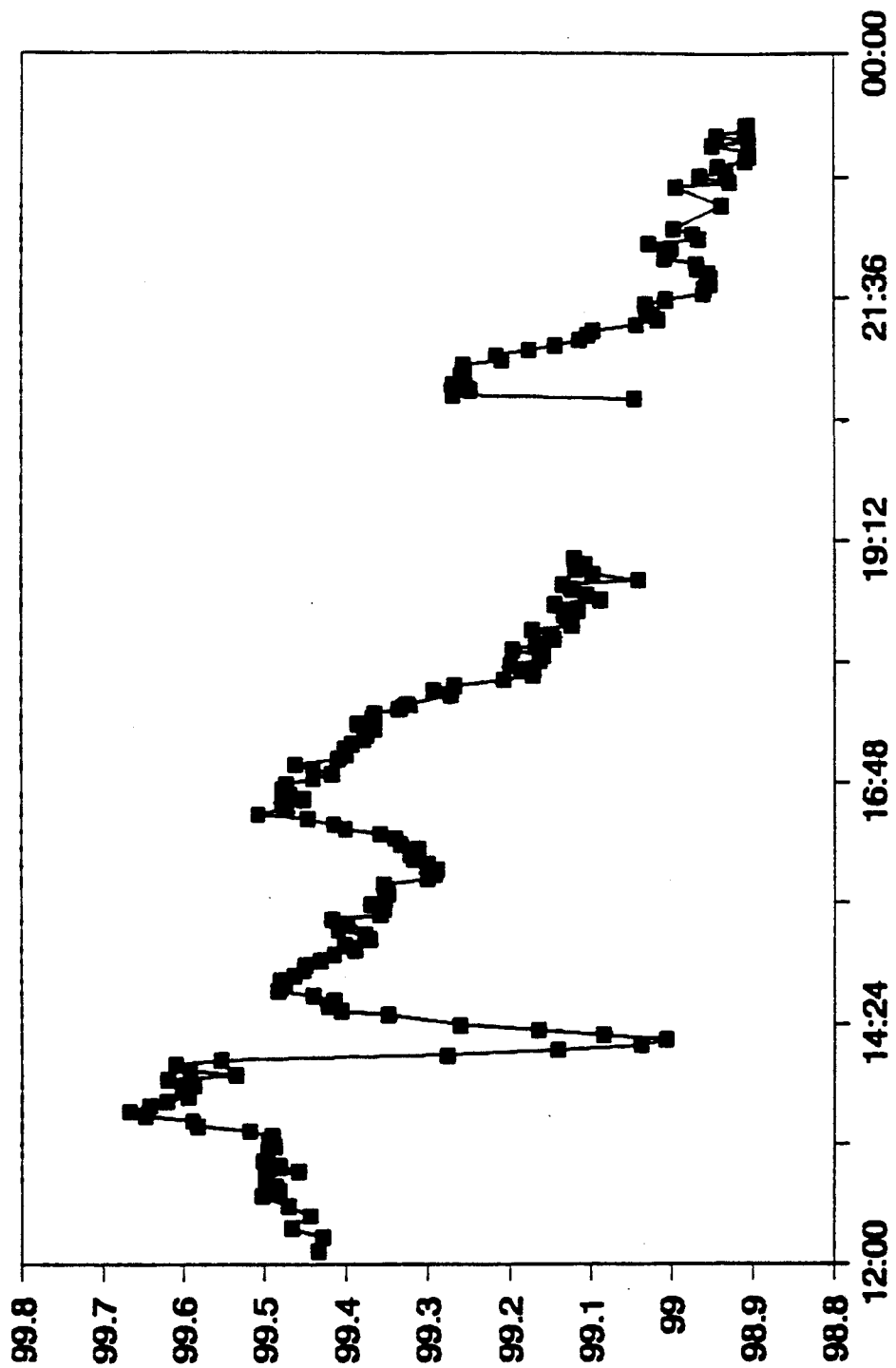

To minimize the effect of humidity variations on the estimation of research octane number, a water vapor correction was added to the model. A "water vapor" spectrum was generated by subtracting successive spectra from the on-line data over periods when the composition was expected to show minimal variation. A CPCR model was constructed using the 3 polynomial background corrections, the water vapor correction, and using 5 Constrained Principal Components in the regression. The resultant model was then used to reanalyze the same on-line data (FIG. 28). The inclusion of the water vapor correction eliminated the periodic oscillation by producing a model that was insensitive to variations in the humidity.

EXAMPLE 11

Measurement Process Quality Control

CPSA allows the spectral variables which are associated with the measurement process to be modeled so that the predictive models can be constrained to be insensitive to these variables. The contribution of these constraint variables to any real spectrum represents the status of the measurement process during the collection of the spectral data. Since the constraint variables are orthogonal among themselves and to the eigenspectra, the relative contributions of the constraint variables to a spectrum are obtained merely by taking the dot product of the constraint vector with the spectrum. The range of values obtained for the calibration spectra represent the range of measurement process variation during the collection of the reference spectra, and can be used to identify reference spectra which are outliers with respect to the measurement process. In building the predictive model it may be desirable to recollect the spectral data for these outliers so as to optimize the model. Similarly, the values of the constraint variables for an unknown spectrum being analyzed serve as an indication of measurement process during the analysis, and can provide a warning if the measurement process has changed significantly relative to the calibration. CPSA thus provide a means of performing quality control on the measurement process, indicating conditions under which changes in the measurement process rather than changes in the sample might be affecting the predicted results.

Figure 25:
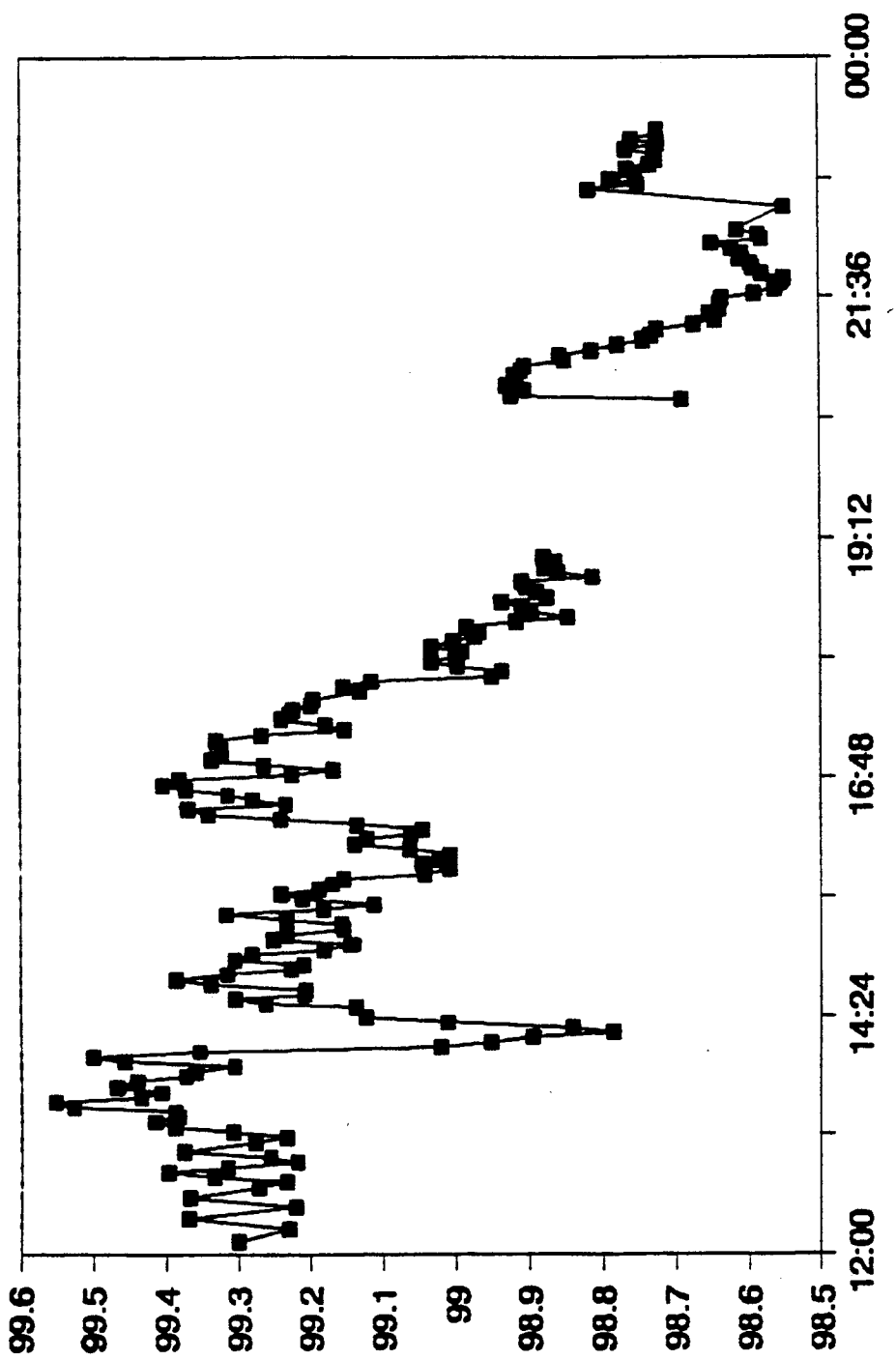
FIGS. 25 to 28 relate to an example demonstrating how constrained spectral analysis can be used to remove measurement process signals in a real application; more specifically
Figure 29:
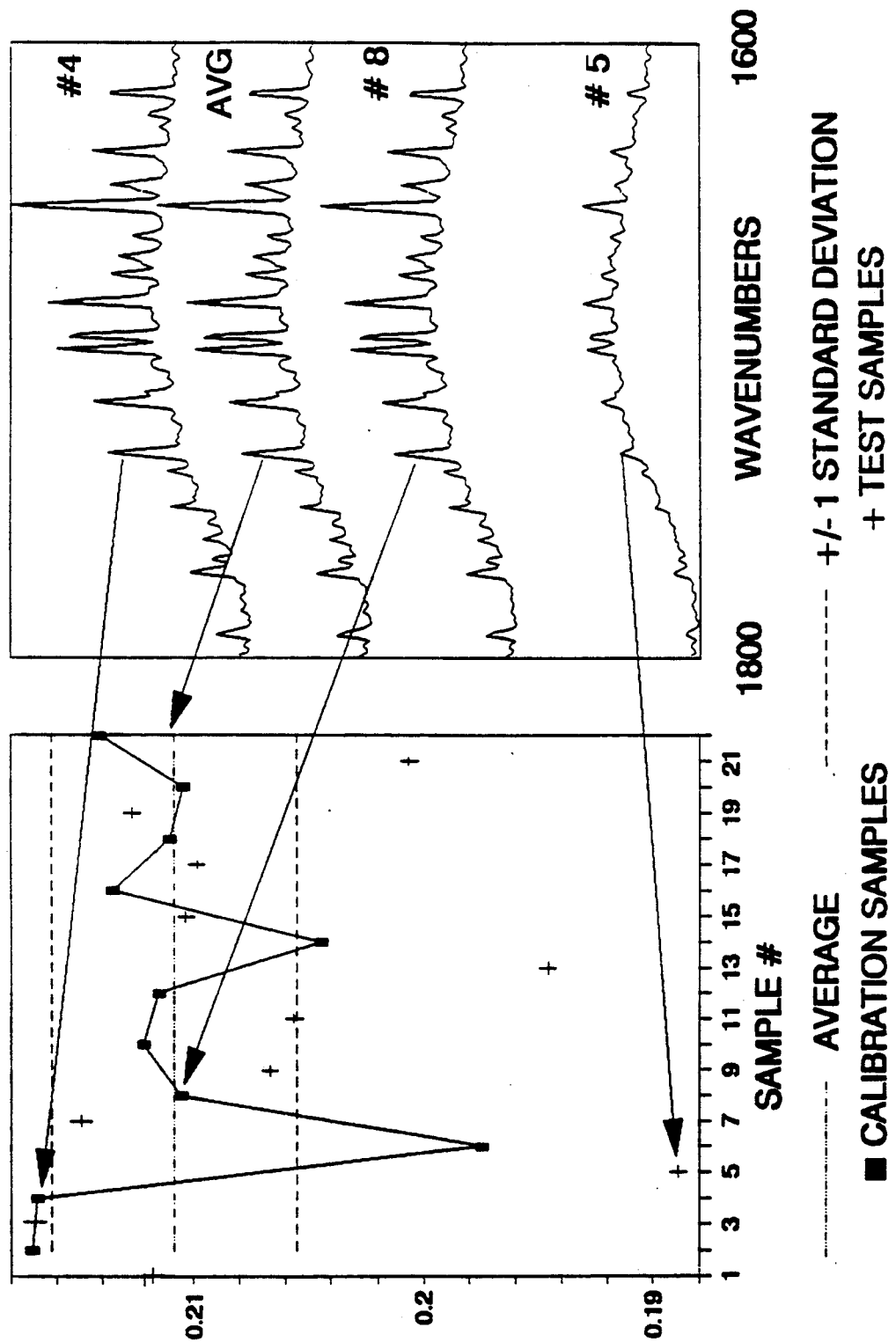
FIGS. 29 and 30 illustrate the effect of correction for water vapor and chloroform, respectively, for isooctane/heptane spectra and for the additive package of Example 9, respectively; more specifically.
Figure 30:
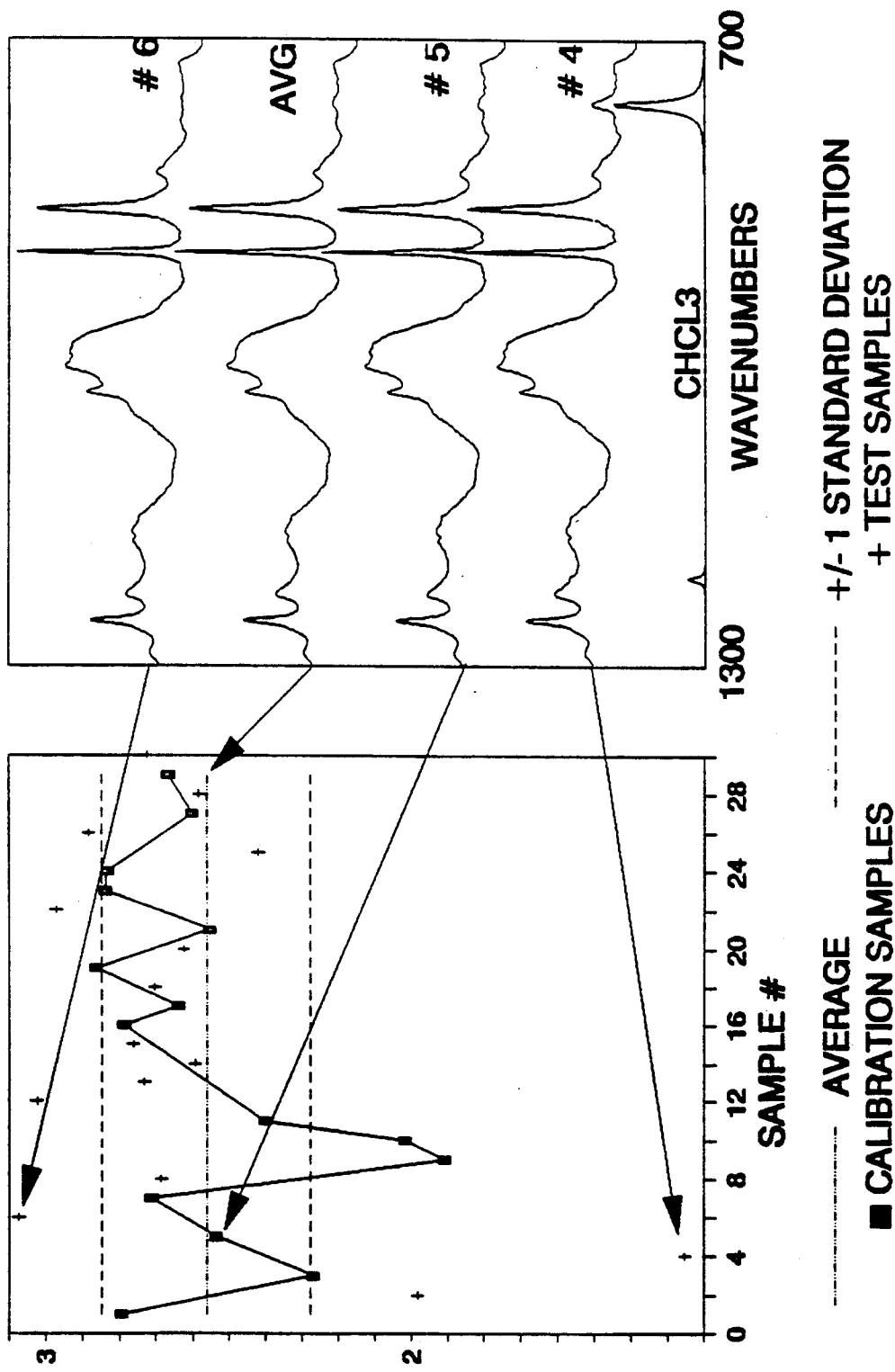
Figure 31:
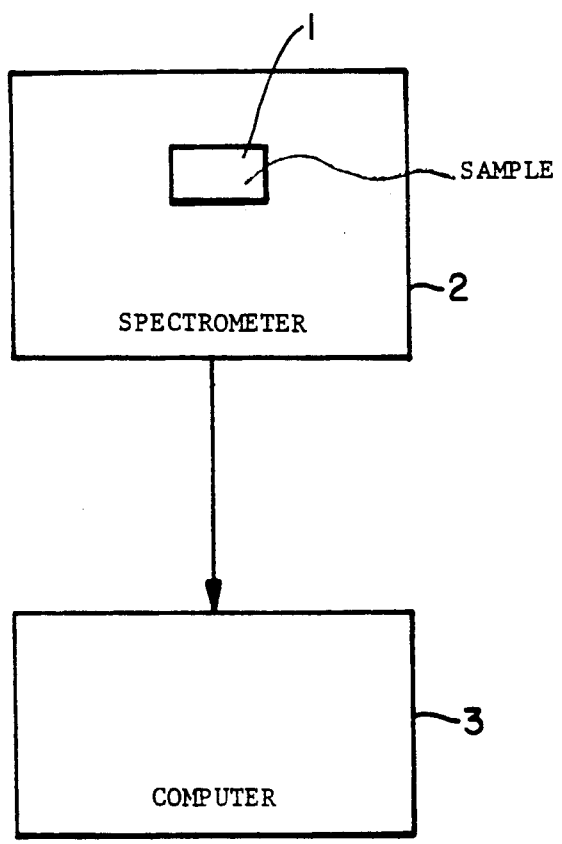
FIG. 31 shows an apparatus for estimating an unknown property or compositional data of a sample (1), comprising a spectrometer (2) for generating the spectrum of a plurality of calibration samples having known properties, and the corresponding data for a sample under consideration whose unknown properties or composition data are to be estimated. The apparatus also comprises a computer (3) which receives the measured spectrum data from the spectrometer.

FIGS. 29 and 30 show examples of how the constraint variables can be used to monitor the spectral measurement process. In the isooctane/heptane example above (Example 8), the spectra were collected in a rapid fashion without allowing sufficient time for the spectrometer to be fully purged. As a result, absorptions due to water vapor are superimposed on the component spectra, and are isolated as a Principal Component (eigenspectrum 5 in FIG. 15) by a PCA calculation. In developing the CPSA model, water vapor correction spectra were used to generate a constraint. FIG. 25 shows a plot of the dot product of the reference and test spectra with the water vapor constraint. The value of the constraint variable clearly identifies spectra which are outliers with respect to the water vapor level, in this case spectra which show a significantly lower water vapor level than the average. FIG. 30 shows similar data for the chloroform constraint used in the additive package example (Example 9). Chloroform was used to rinse the cell between samples, tends to penetrate into small openings between the spacer and the windows, and is not always completely removed even when a vacuum is pulled on the cell. The value of the chloroform constraint variable clearly indicates spectra for which an above (sample 4) or below (sample 6) average amount of chloroform contamination was present. Note that since the peaks in the chloroform constraint spectrum (FIG. 23) are negative, lower values of the dot product imply higher levels of chloroform.

It will be appreciated that various modifications and changes may be made to the methods and apparatus disclosed herein within the scope of the invention as defined by the appended claims. Such modifications and changes will be obvious to the skilled addressee and will not be further described herein.

TABLE 1

Data for Synthetic Calibration Spectra, Example 1

| Sample # | Component A | Component B | Offsets Data Sets [2] & [4] | Offsets Data Sets [5] | Dependent Value Error Case 1 | Dependent Value Error Case 2 |
|---|---|---|---|---|---|---|
| 1 | 0 | 100 | 1.07372 | −0.78081 | −0.24835 | −0.01869 |
| 2 | 2 | 98 | 0.62511 | −0.41887 | 0.07831 | 0.24835 |
| 3 | 4 | 96 | 1.25119 | −0.32886 | 0.06027 | −0.02899 |
| 4 | 6 | 94 | 0.41396 | −0.28975 | −0.64586 | 0.30214 |
| 5 | 8 | 92 | 2.36442 | 0.08348 | 0.02363 | −0.38320 |
| 6 | 10 | 90 | 1.39797 | 0.15223 | 0.04501 | −0.06027 |
| 7 | 12 | 88 | 1.39477 | 0.17348 | 0.04871 | −0.04871 |
| 8 | 14 | 86 | 0.89075 | 0.24735 | −0.05920 | 0.10868 |
| 9 | 16 | 84 | 1.12097 | 0.41396 | 0.01869 | −0.01963 |
| 10 | 18 | 82 | 0.84817 | 0.55425 | 0.00441 | 0.11668 |
| 11 | 20 | 80 | 0.71911 | 0.62511 | −0.36602 | 0.21138 |
| 12 | 22 | 78 | 0.95787 | 0.68433 | 0.10105 | 0.03834 |
| 13 | 24 | 76 | 1.02863 | 0.71911 | −0.05233 | −0.00291 |
| 14 | 26 | 74 | 0.97184 | 0.74038 | 0.61309 | 0.03143 |
| 15 | 28 | 72 | 0.94610 | 0.78470 | −0.13453 | 0.05920 |
| 16 | 30 | 70 | −0.41887 | 0.83386 | 0.01784 | 0.79082 |
| 17 | 32 | 68 | 1.34454 | 0.84817 | −0.88469 | −0.03226 |
| 18 | 34 | 66 | −0.28975 | 0.89075 | 0.00291 | 0.64586 |
| 19 | 36 | 64 | 1.30954 | 0.89655 | 0.02024 | −0.03043 |
| 20 | 38 | 62 | 0.78470 | 0.90107 | −0.72503 | 0.15675 |
| 21 | 40 | 60 | 2.37187 | 0.91054 | 0.11409 | −0.61309 |
| 22 | 42 | 58 | 0.08348 | 0.94610 | 0.09400 | 0.44731 |
| 23 | 44 | 56 | 0.15223 | 0.95090 | 0.01963 | 0.39589 |
| 24 | 46 | 54 | 0.99238 | 0.95787 | −0.39589 | 0.01219 |
| 25 | 48 | 52 | 3.53012 | 0.97184 | −0.01182 | −0.87598 |
| 26 | 50 | 50 | 1.84674 | 0.99238 | −0.79082 | −0.15782 |
| 27 | 52 | 48 | 0.95090 | 0.99982 | 0.03226 | 0.05233 |
| 28 | 54 | 46 | 0.91054 | 1.01348 | −0.10868 | 0.07141 |
| 29 | 56 | 44 | 1.35166 | 1.02863 | 0.87598 | −0.04501 |
| 30 | 58 | 42 | 1.46935 | 1.03097 | −0.21138 | −0.07831 |
| 31 | 60 | 40 | 1.04336 | 1.04336 | −0.21987 | −0.01784 |
| 32 | 62 | 38 | 1.01348 | 1.07372 | −0.03834 | −0.00017 |
| 33 | 64 | 36 | 0.74038 | 1.09651 | −0.10678 | 0.19087 |
| 34 | 66 | 34 | 0.90107 | 1.12097 | 0.28876 | 0.07677 |
| 35 | 68 | 32 | 0.99982 | 1.15763 | 0.01874 | 0.01182 |
| 36 | 70 | 30 | 2.06437 | 1.22472 | −0.44731 | −0.28876 |
| 37 | 72 | 28 | 0.17348 | 1.25119 | −0.19087 | 0.37935 |
| 38 | 74 | 26 | 0.89655 | 1.30954 | −0.11668 | 0.10678 |
| 39 | 76 | 24 | −0.78081 | 1.34454 | −0.37935 | 0.88469 |
| 40 | 78 | 22 | 1.65423 | 1.35166 | −0.30214 | −0.09400 |
| 41 | 80 | 20 | 1.09651 | 1.39477 | 0.03043 | −0.01874 |
| 42 | 82 | 18 | 0.68433 | 1.39797 | 0.02899 | 0.21987 |
| 43 | 84 | 16 | 1.69807 | 1.46935 | 0.15782 | −0.10105 |
| 44 | 86 | 14 | 0.24735 | 1.65423 | −0.01219 | 0.36602 |
| 45 | 88 | 12 | 0.03097 | 1.69807 | 0.00017 | −0.00441 |
| 46 | 90 | 10 | 0.83386 | 1.70383 | 0.38320 | 0.13453 |
| 47 | 92 | 8 | 1.70383 | 1.84674 | −0.29414 | −0.11409 |
| 48 | 94 | 6 | 1.15763 | 2.06437 | −0.15675 | −0.02024 |
| 49 | 96 | 4 | 1.22472 | 2.36442 | −0.07677 | −0.02363 |
| 50 | 98 | 2 | −0.32886 | 2.37187 | −0.03143 | 0.72503 |
| 51 | 100 | 0 | 0.55425 | 3.53012 | −0.07141 | 0.29414 |

TABLE 2

Data for Synthetic Test Spectra, Example 1

| Sample # | Component A | Component B | Offsets | Dependent Value Error |
|---|---|---|---|---|
| 1 | 1 | 99 | 0.61018 | 0.01874 |
| 2 | 3 | 97 | 0.97772 | 0.61309 |
| 3 | 5 | 95 | 1.04011 | −0.37935 |
| 4 | 7 | 93 | 1.21413 | 0.09400 |
| 5 | 9 | 91 | 1.17595 | 0.02024 |
| 6 | 11 | 89 | 0.97127 | 0.02899 |
| 7 | 13 | 87 | 2.06759 | −0.03834 |
| 8 | 15 | 85 | 0.04622 | 0.00017 |
| 9 | 17 | 83 | 1.05222 | −0.10868 |
| 10 | 19 | 81 | −1.66840 | 0.06027 |
| 11 | 21 | 79 | −0.32858 | −0.64586 |
| 12 | 23 | 77 | 3.99964 | −0.21987 |
| 13 | 25 | 75 | 0.06950 | −0.10678 |
| 14 | 27 | 73 | 0.10144 | −0.05920 |
| 15 | 29 | 71 | 1.44476 | 0.01963 |
| 16 | 31 | 69 | 4.14906 | −0.01182 |
| 17 | 33 | 67 | 1.46563 | −0.24835 |
| 18 | 35 | 65 | 0.87267 | −0.30214 |
| 19 | 37 | 63 | 0.73178 | 0.10105 |
| 20 | 39 | 61 | 1.66786 | −0.39589 |
| 21 | 41 | 59 | 0.18927 | 0.07831 |
| 22 | 43 | 57 | 0.91056 | 0.01784 |
| 23 | 45 | 55 | 1.29793 | −0.19087 |
| 24 | 47 | 53 | 0.74590 | −0.79082 |
| 25 | 49 | 51 | 0.93587 | −0.88469 |
| 26 | 51 | 49 | 1.84299 | 0.04501 |
| 27 | 53 | 47 | 1.06558 | −0.01219 |
| 28 | 55 | 45 | 1.11103 | 0.04871 |
| 29 | 57 | 43 | 0.65312 | 0.28876 |
| 30 | 59 | 41 | 1.01586 | 0.02363 |
| 31 | 61 | 39 | 2.48578 | −0.29414 |
| 32 | 63 | 37 | −0.08490 | 0.15782 |
| 33 | 65 | 35 | 1.05601 | 0.11409 |
| 34 | 67 | 33 | 0.00175 | 0.03043 |
| 35 | 69 | 31 | 0.88686 | −0.07677 |
| 36 | 71 | 29 | 1.62194 | 0.87598 |
| 37 | 73 | 27 | 0.43761 | −0.36602 |
| 38 | 75 | 25 | 0.38382 | −0.05233 |
| 39 | 77 | 23 | 1.26709 | 0.00441 |
| 40 | 79 | 21 | 3.75128 | −0.13453 |
| 41 | 81 | 19 | 0.86992 | −0.72503 |
| 42 | 83 | 17 | 1.13135 | 0.03226 |
| 43 | 85 | 15 | 1.57232 | 0.38320 |
| 44 | 87 | 13 | 0.87528 | −0.21138 |
| 45 | 89 | 11 | 1.02326 | −0.15675 |
| 46 | 91 | 9 | 0.40350 | −0.11668 |
| 47 | 93 | 7 | 1.47357 | −0.03143 |
| 48 | 95 | 5 | 2.06262 | −0.07141 |
| 49 | 97 | 3 | −3.69166 | 0.01869 |
| 50 | 99 | 1 | 2.07528 | 0.00291 |

TABLE 3

Standard Errors for Example 1
No Error in Dependent Values

| Analysis Number | Analysis Type | Number of Principal | SEE | SEP |
|---|---|---|---|---|
| | Analysis of data set [1] | | | |
| 1 | [a] | 2 | 0.000 | 0.000 |
| 2 | [b] | 2 | 0.000 | 0.000 |
| 3 | [c] | 2 | 0.000 | 0.000 |
| | Analysis of data set [2] | | | |
| 4 | [a] | 2 | 1.308 | 2.105 |
| 5 | [a] | 3 | 0.000 | 0.000 |
| 6 | [b] | 2 | 0.000 | 0.000 |
| 7 | [c] | 2 | 0.000 | 0.000 |
| | Analysis of data set [3] | | | |
| 8 | [a] | 2 | 0.064 | 0.080 |
| 9 | [b] | 2 | 0.835 | 0.793 |
| 10 | [b] | 3 | 0.072 | 0.101 |
| 11 | [c] | 2 | 0.078 | 0.087 |
| | Analysis of data set [4] | | | |
| 12 | [a] | 2 | 1.314 | 2.093 |
| 13 | [a] | 3 | 0.079 | 0.086 |
| 14 | [b] | 2 | 0.835 | 0.793 |
| 15 | [b] | 3 | 0.072 | 0.101 |
| 16 | [c] | 2 | 0.078 | |

Analysis types:
[a] Principal Components Analysis
[b] Principal Components Analysis after preprocessing
[c] Constrained Principal Components Analysis
Data Sets:
[1] Synthetic Components
[2] Plus variable offset
[3] Plus noise
[4] Plus variable offset and noise
Standard Error of Estimate (for 51 calibration spectra and N Principal Components):
$SEE^2 = [\Sigma(\text{Calculated} - \text{Calibration Value})^2/(51 - N)]$
Standard Error of Prediction (for 50 test spectra):
$SEP^2 = [\Sigma(\text{Predicted} - \text{Calibration Value})^2]/50$

TABLE 4

Standard Errors for Example 1
Including Dependent Value Errors

| Anal. Type | # of PCs | Case 1 Uncorrelated Error SEE | SEP | Act | Case 2 Correlated Error SEE | SEP | Act |
|---|---|---|---|---|---|---|---|
| | | Analysis of data set [1] | | | | | |
| [a] | 2 | 0.306 | 0.334 | 0.079 | 0.304 | 0.301 | 0.085 |
| [b] | 2 | 0.306 | 0.334 | 0.079 | 0.304 | 0.301 | 0.085 |
| [c] | 2 | 0.306 | 0.334 | 0.079 | 0.304 | 0.301 | 0.085 |
| | | Analysis of data set [2] | | | | | |
| [a] | 2 | 1.346 | 2.130 | 2.109 | 1.010 | 2.120 | 2.104 |
| [a] | 3 | 0.309 | 0.334 | 0.079 | 0.061 | 0.564 | 0.487 |
| [b] | 2 | 0.306 | 0.334 | 0.079 | 0.304 | 0.301 | 0.085 |
| [c] | 2 | 0.306 | 0.334 | 0.079 | 0.304 | 0.301 | 0.085 |
| | | Analysis of data set [3] | | | | | |
| [a] | 2 | 0.320 | 0.324 | 0.094 | 0.306 | 0.302 | 0.132 |
| [b] | 2 | 0.859 | 0.817 | 0.784 | 0.868 | 0.818 | 0.799 |
| [b] | 3 | 0.317 | 0.330 | 0.121 | 0.307 | 0.311 | 0.155 |
| [c] | 2 | 0.321 | 0.328 | 0.095 | 0.308 | 0.310 | 0.140 |
| | | Analysis of data set [4] | | | | | |
| [a] | 2 | 1.353 | 2.097 | 2.115 | 1.015 | 2.106 | 2.093 |
| [a] | 3 | 0.323 | 0.096 | 0.328 | 0.093 | 0.569 | 0.500 |
| [b] | 2 | 0.859 | 0.817 | 0.784 | 0.868 | 0.818 | 0.799 |
| [b] | 3 | 0.317 | 0.330 | 0.121 | 0.307 | 0.311 | 0.155 |
| [c] | 2 | 0.321 | 0.329 | 0.096 | 0.308 | 0.310 | 0.140 |

Analysis types:
[a] Principal Components Analysis
[b] Principal Components Analysis after preprocessing
[c] Constrained Principal Components Analysis
Data Sets:
[1] Synthetic Components
[2] Plus variable offset
[3] Plus noise
[4] Plus variable offset and noise
Standard Error of Estimate (for 51 calibration spectra and N Principal Components):
$SEE^2 = [\Sigma(Calculated - Calibration\ Value)^2]/(51 - N)$
Standard Error of Prediction (for 50 test spectra):
$SEP^2 = [\Sigma(Predicted - Calibration\ Value)^2]/50$
$Act^2 = [\Sigma(Predicted - True\ Value)^2]/50$

TABLE 5

Standard Errors for Example 1
Offset Correlated to Dependent Value

| Analysis Type | Number Principal | SEE | SEP |
|---|---|---|---|
| | Analysis of data set [5] | | |
| [a] | 3 | 0.079 | 0.239 |
| [c] | 2 | 0.079 | 0.087 |

Analysis types:
[a] Principal Components Analysis
[c] Constrained Principal Components Analysis
Data Sets:
[5] Synthetic Components, offset correlated to dependent value, noise
Standard Error of Estimate (for 51 calibration spectra and N Principal Components):
$SEE^2 = [\Sigma(Calculated - Calibration\ Value)^2]/(51 - N)$
Standard Error of Prediction (for 50 test spectra):
$SEP^2 = [\Sigma(Predicted - Calibration\ Value)^2]/50$

TABLE 6

Binary Isooctane/Heptane Samples

| | Isooctane Volume % | Heptane Volume % |
|---|---|---|
| Calibration Samples | | |
| 2 | 78 | 22 |
| 4 | 82 | 18 |
| 6 | 84 | 16 |
| 8 | 86 | 14 |
| 10 | 88 | 12 |
| 12 | 90 | 10 |
| 14 | 92 | 8 |
| 16 | 94 | 6 |
| 18 | 96 | 4 |
| 20 | 98 | 2 |
| 22 | 100 | 1 |
| Test Samples | | |
| 1 | 76 | 24 |
| 3 | 80 | 20 |
| 5 | 83 | 17 |
| 7 | 85 | 15 |
| 9 | 87 | 13 |
| 11 | 89 | 11 |
| 13 | 91 | 9 |
| 15 | 93 | 7 |
| 17 | 95 | 5 |
| 19 | 97 | 3 |
| 21 | 99 | 1 |

TABLE 7

Standard Errors for Heptane/Isooctane Binary Mixtures

| Type of Model | # PC | Isooctane SEE | SEP | Heptane SEE | SEP |
|---|---|---|---|---|---|
| Models based on 11 reference spectra without pathlength correction: | | | | | |
| PCR | 2 | 2.715 | 3.396 | 6.736 | 8.198 |
| | 3 | 0.263 | 0.551 | 0.466 | 1.081 |
| | 4 | 0.197 | 0.187 | 0.035 | 0.077 |
| | 5 | 0.118 | 0.213 | 0.035 | 0.085 |
| | 6 | 0.129 | 0.218 | 0.030 | 0.062 |
| CPCR | 2 | 0.196 | 0.248 | 0.045 | 0.056 |
| Results renormalized so heptane plus isooctane equals 100%: | | | | | |
| PCR | 4 | 0.040 | 0.077 | 0.040 | 0.077 |
| | 5 | 0.028 | 0.094 | 0.028 | 0.094 |
| CPCR | 2 | 0.056 | 0.071 | 0.056 | 0.071 |
| Results for models employing pahtlength correction: | | | | | |
| PCR | 2 | 6.394 | 6.986 | 6.394 | 6.986 |
| | 3 | 0.445 | 0.977 | 0.445 | 0.977 |
| | 4 | 0.045 | 0.072 | 0.045 | 0.072 |
| | 5 | 0.034 | 0.091 | 0.034 | 0.091 |
| CPCR | 2 | 0.056 | 0.071 | 0.056 | 0.071 |

TABLE 8

Comparison of K Matrix, PCA and CPSA
Results for Add Pack Analysis
Models based on 15 blend spectra plus cyclohexane
Results renormalized so 5 add pack components add to 100%

| Model | # Variables | Disp | NPS | ZDDP | Mg Sulf | Oil |
|---|---|---|---|---|---|---|
| Standard Error of Estimate | | | | | | |
| K Matrix | 6 | 0.369 | 0.363 | 0.150 | 0.164 | 0.704 |
| PCA | 9 | 0.148 | 0.217 | 0.106 | 0.088 | 0.126 |
| CPSA | 7 | 0.291 | 0.271 | 0.143 | 0.128 | 0.220 |
| CPSA* | 7 | 0.299 | 0.273 | 0.144 | 0.127 | 0.229 |
| Standard Error of Prediction | | | | | | |
| K Matrix | 6 | 0.412 | 0.398 | 0.132 | 0.300 | 0.612 |
| PCA | 9 | 0.429 | 0.285 | 0.147 | 0.300 | 0.367 |
| CPSA | 7 | 0.410 | 0.267 | 0.098 | 0.314 | 0.378 |
| CPSA* | 7 | 0.402 | 0.263 | 0.099 | 0.313 | 0.375 |

*CPSA model including water vapor constraint

TABLE 9

PCA Analysis of CPSA Constraints

| Contraint | Disp | NPS | ZDDP | Mg Sulf | Oil |
|---|---|---|---|---|---|
| Polynomial 1 (constant) | 0.902 | 2.094 | 1.342 | 1.436 | 2.521 |
| Polynomial 2 (linear) | −5.500 | 2.099 | 1.149 | −0.843 | 12.110 |
| Polynomial 3 (square) | −1.321 | −5.889 | −1.147 | 1.009 | 1.060 |
| Correction 1 (CHCL$_3$) | −0.221 | −0.34 | 0.213 | −0.105 | 0.230 |

The Constrained Principal Spectra Analysis method allows the spectroscopist to input his knowledge of the spectral measurements so as to define and model possible spectral variations which are due to the measurement process, and to develop multivariate predictive models which are constrained to be insensitive to the measurement process signals. The constraints developed in this fashion serve as quality control variables for the measurement process, allowing for the optimization of the calibration and subsequent monitoring of the spectral measurement. The CPSA algorithm provides advantage over spectral preprocessing techniques in that: (1) it uses all available spectral data to derive and remove the measurement process variables and as such is less sensitive to spectral noise than methods based on limited ranges of the data, (2) it uses a single calculation method to remove all types of measurement process variations including variables for which preprocessing algorithms would be difficult or impossible to develop (e.g. highly overlapping interferences or higher order background variations), (3) it provides measurement process variables which are orthogonal to the spectral Principal Components thereby insuring maximum stability of the predictive model, and (4) it incorporates the modeling and removal of measurement process variables as an integral part of the analysis thereby removing the necessity for the development of separate preprocessing methods and algorithms.

It will be appreciated that various modifications and changes may be made to the methods and apparatus disclosed herein within the scope of the invention as defined by the appended claims. Such modifications and changes will be obvious to the skilled addressee and will not be further described herein.

The concepts and mathematical techniques disclosed in this patent specification are relatively complex. Although the invention has been fully described in the foregoing pages, there is set out hereinafter, under the heading "Appendix", a detailed description of the mathematical techniques used, starting from first principles. This Appendix forms part of the disclosure of the present specification.

APPENDIX

1.0 Definition of Mathematical Terms, Symbols and Equations

1.1 Scalars

Variables representing scalar quanitites will be designated by lowercase, normal typeface letters, e.g. x or y. Scalar quanities are real numbers. Examples would include but not be limited to the concentration of a single component in a single sample, the value of a single property for a single sample, the absorbance at a single frequency for a single sample.

1.2 Vectors

Vectors will be represented as lowercase, boldface letters. Vectors are a one dimensional array of scalar values. Two types of vectors will be distinguished.

$$v = \begin{pmatrix} v_1 \\ v_2 \\ v_3 \\ v_4 \\ v_5 \\ v_6 \\ v_7 \\ v_8 \\ v_9 \end{pmatrix}$$

is an example of a column vector of dimension 9. The corresponding row vector, $$v^t = (v_1 v_2 v_3 v_4 v_5 v_6 v_7 v_8 v_9)$$

is also of dimension 9. The superscript $t$ indicates that the row vector is the transpose of the corresponding column vector.

Normal face, lowercase letter with subscripts will be used to refer to the individual elements of the vector, e.g. $v_1$, $v_2$, $v_3$, etc., which are scalar quanities. The subscripts $1,2,3$, etc. indicate the position of the quanity in the vector. The expression $v_i$ will be used to represent a general position i in the vector. Bold face, lowercase letters with subscripts will be used to represent one of a set of vectors, i.e. $v_1$, $v_2$, ... $v_n$ would be a set of n vectors.

1.2.1 Product of a Scalar Times a Vector

If $$v = \begin{pmatrix} v_1 \\ v_2 \\ v_3 \\ v_4 \\ v_5 \\ v_6 \\ v_7 \\ v_8 \\ v_9 \end{pmatrix},$$

then the multiplication of v by a scalar a is $$va = \begin{pmatrix} av_1 \\ av_2 \\ av_3 \\ av_4 \\ av_5 \\ av_6 \\ av_7 \\ av_8 \\ av_9 \end{pmatrix}$$

If $v^t = (v_1\ v_2\ v_3\ v_4\ v_5\ v_6\ v_7\ v_8\ v_9)$ then $av^t = (av_1\ av_2\ av_3\ av_4\ av_5\ av_6\ av_7\ av_8\ av_9)$

1.2.2 Dot Product of two vectors

The dot product of a column and a row vector is a scalar quanity. The dot product is defined only if the vectors are of the same dimension. The dot product is the sum of the products of the individual elements of the two vectors, i.e.

$$u^t v = (u_1\ u_2\ u_3\ u_4\ u_5\ u_6\ u_7) \begin{pmatrix} v_1 \\ v_2 \\ v_3 \\ v_4 \\ v_5 \\ v_6 \\ v_7 \end{pmatrix} =$$

$$u_1 v_1 + u_2 v_2 + u_3 v_3 + u_4 v_4 + u_5 v_5 + u_6 v_6 + u_7 v_7$$

Two vectors will be referred to as being orthogonal if their dot product is equal to zero. If a vector z is orthogonal to vectors u and v, it is orthogonal to any linear combination of u and v, i.e.

if $z^t u = z^t v = 0$ and $y = ua + vb$ for any scalar coefficients a and b
then $z^t y = z^t u a + z^t v b = 0a + 0b = 0$.

1.2.3 Length of a Vector

The length of a vector is the square root of the dot product of the vector with its transpose, and will be designated by $\|v\|$, i.e.

$$\|v\| = \|v^t\| = (v^t v)^{0.5}$$

A vector will be referred to as normal, unit or normalized if the length of the vector is equal to one. A zero vector refers to a vector of zero length, i.e. one whose elements are all zero.

1.2.4 An Orthonormal Set of Vectors

A set of vectors $u_1, u_2, \ldots u_n$, form an orthonormal set if the dot products $u_i^t u_i = 1$ and $u_i^t u_j = 0$ for $i$ not equal to $j$ where $i$ and $j$ run from $1$ to $n$. The individual vectors are normalized, and the dot products between any two different vectors is equal to zero.

1.2.5 Orthogonalization and Normalization of Vectors

Given a vector u of length $\|u\|$, it is possible to define a new, normal vector u' as $u' = u/\|u\|$. u' is obtained from u by dividing each of the elements by the length of the vector. This procedure is referred to as normalization of the vector.

If u is a normal vector, and v is a vector such that the dot product $u^t v = d$, the vector $z = v - du$ is orthogonal to u, i.e. $u^t z = u^t v - d u^t u = d - d = 0$. The procedure for calculating z is referred to as orthogonalization of the vectors.

Given a set of n vectors, $x_1, x_2, \ldots x_n$, it is possible to derive a new set of n vectors, $u_1, u_2, \ldots u_n$, that form an orthonormal set. This procedure which is referred to as Gram-Schmidt Orthogonalization involves the following steps:

[1] chosing an initial vector, $x_1$, and normalizing it to produce $u_1$;

[2] choosing a second vector, $x_2$, orthogonalizing it to $u_1$ normalizing the resultant vector to produce $u_2$;

[3] choosing a third vector, $x_3$, orthogonalizing it to both $u_1$ and $u_2$, and normalizing the result to produce $u_3$;

[4] continuing the process of choosing vectors $x_i$, orthogonalizing them to the vectors $u_1, u_2, \ldots u_{i-1}$ which were already calculated, and normaling the resultant vectors to produce new $u_i$ until all vectors have been processed.

1.3 Matrices

A matrix is a two dimensional array of scalar values. Matrices will be designated as uppercase, boldfaced letters. For example, $$X = \begin{pmatrix} x_{11} & x_{12} & x_{13} & x_{14} \\ x_{21} & x_{22} & x_{23} & x_{24} \\ x_{31} & x_{32} & x_{33} & x_{34} \\ x_{41} & x_{42} & x_{43} & x_{44} \\ x_{51} & x_{52} & x_{53} & x_{54} \\ x_{61} & x_{62} & x_{63} & x_{64} \\ x_{71} & x_{72} & x_{73} & x_{74} \\ x_{81} & x_{82} & x_{83} & x_{84} \\ x_{91} & x_{92} & x_{93} & x_{94} \end{pmatrix}$$

is a 9 by 4 matrix.

The general element of the matrix X, $x_{ij}$, indicates the value in the $i^{th}$ row and the $j^{th}$ column. The dimensions of a matrix, i.e. the numbers of rows and columns, will be indicated as italicized, lowercase letters, i.e. a matrix X of dimension f by n where in the above example f is 9, and n is 4. The individual columns of a matrix are column vectors, e.g. the vector $x_1$ would be the vector containing the same elements as the first column of the matrix X. The individual rows of a matrix are row vectors, e.g. the vector $x_i^t$ is the $i^{th}$ row of the matrix X.

1.3.1 Matrix Transpose

The transpose of a matrix X is obtained by interchanging the rows and columns, and will be designated by $X^t$. For example, $$\text{if } X = \begin{pmatrix} x_{11} & x_{12} & x_{13} & x_{14} \\ x_{21} & x_{22} & x_{23} & x_{24} \\ x_{31} & x_{32} & x_{33} & x_{34} \\ x_{41} & x_{42} & x_{43} & x_{44} \\ x_{51} & x_{52} & x_{53} & x_{54} \\ x_{61} & x_{62} & x_{63} & x_{64} \\ x_{71} & x_{72} & x_{73} & x_{74} \\ x_{81} & x_{82} & x_{83} & x_{84} \\ x_{91} & x_{92} & x_{93} & x_{94} \end{pmatrix}$$

$$\text{then } X^t = \begin{pmatrix} x_{11} & x_{21} & x_{31} & x_{41} & x_{51} & x_{61} & x_{71} & x_{81} & x_{91} \\ x_{12} & x_{22} & x_{32} & x_{42} & x_{52} & x_{62} & x_{72} & x_{82} & x_{92} \\ x_{13} & x_{23} & x_{33} & x_{43} & x_{53} & x_{63} & x_{73} & x_{83} & x_{93} \\ x_{14} & x_{24} & x_{34} & x_{44} & x_{54} & x_{64} & x_{74} & x_{84} & x_{94} \end{pmatrix}$$

If the matrix X is of dimension f by n, then the matrix $X^t$ is of dimension n by f.

1.3.2 Matrix Multiplication

If U is a matrix of dimension f by k, and V is a matrix of dimension k by n, then the product matrix Z=UV is a matrix of dimension f by n. The $z_{ij}$ element of Z is calculated by taking the dot product of the $i^{th}$ row vector $u_i^t$ from U and the $j^{th}$ column vector $v_j$ for V.

$$\text{If } U = \begin{pmatrix} u_{11} & u_{12} \\ u_{21} & u_{22} \\ u_{31} & u_{32} \\ u_{41} & u_{42} \end{pmatrix} \text{ and } V = \begin{pmatrix} v_{11} & v_{12} & v_{13} \\ v_{21} & v_{22} & v_{23} \end{pmatrix}$$

then $Z = UV =$ $$\begin{pmatrix} u_{11}v_{11} + u_{12}v_{21} & u_{11}v_{12} + u_{12}v_{22} & u_{11}v_{13} + u_{12}v_{23} \\ u_{21}v_{11} + u_{22}v_{21} & u_{21}v_{12} + u_{22}v_{22} & u_{21}v_{13} + u_{22}v_{23} \\ u_{31}v_{11} + u_{32}v_{21} & u_{31}v_{12} + u_{32}v_{22} & u_{31}v_{13} + u_{32}v_{23} \\ u_{41}v_{11} + u_{42}v_{21} & u_{41}v_{12} + u_{42}v_{22} & u_{41}v_{13} + u_{42}v_{23} \end{pmatrix}$$

The product is only defined if the inner dimensions of the two matrices, e.g. k in this example, are the same. The vectors formed by the columns of the product matrix Z are linear combinations of the column vectors of U, i.e.

$$z_1 = \begin{pmatrix} u_{11}v_{11} + u_{12}v_{21} \\ u_{21}v_{11} + u_{22}v_{21} \\ u_{31}v_{11} + u_{32}v_{21} \\ u_{41}v_{11} + u_{42}v_{21} \end{pmatrix} =$$

$$\begin{pmatrix} u_{11} \\ u_{21} \\ u_{31} \\ u_{41} \end{pmatrix} v_{11} + \begin{pmatrix} u_{12} \\ u_{22} \\ u_{32} \\ u_{42} \end{pmatrix} v_{21} = u_1 v_{11} + u_2 v_{21}$$

The product of more that two matrices, e.g. ABC, is obtained by taking the products of the matrices two at a time, i.e. the product of AB times C, or A times the product of BC.

The transpose of a product of two matrices is the product of the transposes in opposite order, i.e.

$(AB)^t = B^t A^t.$

1.3.3 Products of Vectors and Matrices

The product of a row vector $u^t$ of dimension k by a matrix V of dimension k by n is a column vector z of dimension n, i.e.

$$\text{if } u^t = (u_1 \; u_2) \text{ and } V = \begin{pmatrix} v_{11} & v_{12} & v_{13} \\ v_{21} & v_{22} & v_{23} \end{pmatrix}$$

then $z = (z_1 \; z_2 \; z_3) = u^t V =$ $(u_1v_{11} + u_2v_{21} \quad u_1v_{12} + u_2v_{22} \quad u_1v_{13} + u_2v_{23})$ The individual elements of z, $z_i$, is calculated as the dot product of $u^t$ with the individual column vectors of V, $v_i$. The product of a matrix U of dimension f by k with a column vector v of dimension k, is a column vector z which is calculated by taking the dot product of the row vectors of U, $u_i^t$, with v.

$$\text{if } U = \begin{pmatrix} u_{11} & u_{12} \\ u_{21} & u_{22} \\ u_{31} & u_{32} \\ u_{41} & u_{42} \end{pmatrix} \text{ and } v = \begin{pmatrix} v_1 \\ v_2 \end{pmatrix}$$

$$\text{then } z = \begin{pmatrix} z_1 \\ z_2 \\ z_3 \\ z_4 \end{pmatrix} = Uv = \begin{pmatrix} u_{11}v_1 + u_{12}v_2 \\ u_{21}v_1 + u_{22}v_2 \\ u_{31}v_1 + u_{32}v_2 \\ u_{41}v_1 + u_{42}v_2 \end{pmatrix}$$

1.3.4 Square, Diagonal and Unit and Unitary Matrices

A square matrix is a matrix whose two dimensions are equal. The diagonal elements of a matrix are the elements $x_{ii}$. The off-diagonal elements of a matrix are the elements $x_{ij}$ for which $i \neq j$. A diagonal matrix is a matrix for which the off-diagonal elements are zero. A unit matrix, wherein designated as I, is a square, diagonal matrix where all the diagonal elements are equal to one. The product of a matrix with an unit matrix is itself, i.e. AI=A. A unitary matrix is a square matrix U for which $U^t U = U U^t = I.$ The column and row vectors of a unitary matrix are orthonormal sets of vectors.

1.3.5 Matrix Inverse

For a square matrix A of dimension n by n, the inverse of A, $A^{-1}$, is the matrix for which $AA^{-1} = A^{-1}A = I.$ The inverse of A may not exist if the rank of A (see section 1.3.6) is less than n. Various computer algorithms are available for calculating the inverse of a square matrix (1).

A non-square matrix U of dimension f by n may have a right inverse, $UU^{-1} = I \text{ if } f < n$ or it may have a left inverse, $U^{-1}U = I \text{ if } f > n.$ If $f < n$, and $U^{-1}U = I$ then $U^{-1} = U^t(UU^t)^{-1}$.
If $f > n$, and $UU^{-1} = I$ then $U^{-1} = (U^t U)^{-1} U^t$.

1.3.6 Eigenvalues and Eigenvectors

For a square matrix A of dimension n by n, the equation $Av = v\lambda_i$ is called the eigenvalue equation for A. The eigenvalues of A, $\lambda_i$, are the scalars for which the equation possesses nonzero solutions in v. The corresponding nonzero vectors $v_i$ are the eigenvectors of A. The eigenvectors of A form an orthonormal set of vectors. The eigenvalue equation may also be written as $$AV = V\Lambda$$

or as $$V^t A V = \Lambda$$

where $\Lambda$ is a diagonal matrix containing the eigenvalues $\lambda_i$, and V is the unitary matrix whose columns are the individual eigenvectors. The eigenvalues of A can be obtained by solving the equation $$\det(A - \Lambda I) = 0$$

where det indicates the determinant of the matrix. Various computer algorithms are available for solving for the eigenvalues and eigenvectors of a square matrix (1).

The rank of a matrix A is equal to the number of nonzero eigenvalues of A. The rank of a square matrix A of dimension n by n is at most n. If the rank of A is less than n, then A is singular and cannot be inverted.

1.3.7 Singular Value Decomposition of a Matrix

For a non-square matrix X of dimension f by n, the singular value decomposition of X is given by $$X = U \Sigma V^t$$

If f > n, then U (dimension f by n), $\Sigma$ (dimension n by n), and V (dimension n by n) matrices have the following properties:
$Y^t U = I$
$\Sigma$ is a diagonal matrix
$V^t V = V V^t = I$ If f < n, then U (dimension f by f), $\Sigma$ (dimension f by f), and V (dimension n by f) matrices have the following properties:
$U^t U = U U^t = I$
$\Sigma$ is a diagonal matrix
$V^t V = I$ The vectors which make up the columns of U are refered to as the left eigenvectors of X, and the vectors which make up the columns of V are referred to as the right eigenvectors of X. The diagonal element of $\Sigma$, $\sigma_{ii}$, are referred to as the singular values of X, and are in the order $\sigma_{11} > \sigma_{22} > \sigma_{33} > \ldots \sigma_{kk}$ where $k$ is the smaller of f or n.

The singular value decomposition of $X^t$ is $V \Sigma U^t$.

The singular value decomposition is related to the eigenvalue analysis in the following manner. The eigenvalue equation for the square matrix $X^t X$ can be written as $$X^t X V = V \Lambda.$$

By substituting the singular value decomposition for X and $X^t$ we obtain $$X^t X V = V \Sigma^t U^t U \Sigma V^t V = V \Lambda.$$

Using the fact that $U^t U = I$ and $V^t V = I$ and that $\Sigma^t = \Sigma$ we obtain $$X^t X V = V \Sigma^2$$

where $\Sigma^2 = \Sigma \Sigma$. From this it can be seen that V is the matrix of eigenvectors for the $X^t X$ matrix, and that $$\Sigma^2 = \Lambda$$

i.e. the singular values of X are the square roots of the eigenvalues of $X^t X$. Similarly, for the matrix $X X^t$ $$X X^t U = U \Sigma V^t V \Sigma U^t U = U \Sigma^2 = U \Lambda$$

U is the matrix of eigenvectors of the $X X^t$ matrix. Note that if f ≥ n, $X^t X$ and $X X^t$ have at most n nonzero eigenvalues. Similarly if f ≤ n, $X^t X$ and $X X^t$ have at most f nonzero eigenvalues.

If X is of dimension f by n, then the inverse of X is given by $V \Sigma^{-1} U^t$, i.e.

$$X^{-1} X = V \Sigma^{-1} U^t X = V \Sigma^{-1} U^t U \Sigma V^t = V V^t$$

$$X X^{-1} = X V \Sigma^{-1} U^t = U \Sigma V^t V \Sigma^{-1} U^t = U U^t$$

where $\Sigma^{-1}$ is a diagonal matrix containing $1/\sigma_i$ on the diagonal. Similarly, the inverse of $X^t$ is given by $U \Sigma^{-1} V^t$, i.e.

$$X^t (X^t)^{-1} = X^t U \Sigma^{-1} V^t = V \Sigma U^t U \Sigma^{-1} V^t = V V^t$$

$$(X^t)^{-1} X^t = U \Sigma^{-1} V^t X^t = U \Sigma^{-1} V^t V \Sigma U^t = U U^t$$

If X if square and of rank k = f = n, then $$V V^t = I \text{ and } U U^t = I$$

In this case, X and $X^t$ both have right and left inverses.

If f > n, $U U^t$ is not an identity matrix, and the expressions for the right inverse of X and for the left inverse of $X^t$ are only approximate. Similarly, if f < n, $V V^t$ is not an identity matrix, and the expressions given for the left inverse of X and for the right inverse of $X^t$ are only approximate.

If $\Sigma$ contains k nonzero singular values, then $$X = U \Sigma V^t = U \Sigma' V'^t$$

where $\Sigma'$ is the k by k matrix containing the nonzero singular values, and U' and V' are the f by k and n by k matrices obtained from U and V by eliminating the columns which correspond to the singular values that are zero. Similarly, $$X^t = V' \Sigma' U'^t$$

$$X^t = V' \Sigma' U'^t$$

$$X^{-1} = V' \Sigma'^{-1} U'^t$$

$$(X^t)^{-1} = U' \Sigma'^{-1} V'^t$$

Similarly, if the k + 1 through n singular values of X are close to zero, these singular values and the corresponding columns of U and V may be eliminated to provide an approximation to the X matrix $X \approx U' \Sigma' V'^t$. Approximations for $X^t$ and for the inverses of X and $X^t$ are obtained similarly.

In developing regression models, it is generally assumed that small singular values correspond to random errors in the X data, and that removal of these values improves the stability and robustness of the regression models. To simplify the notation in the discussion below, the ' will be dropped, and the symbols U, $\Sigma$, and V will represent the f by k, k by k, and n by k matrices obtained after eliminating the singular values that are at, or close to zero.

The matrix U is can be calculated as $$U = X V \Sigma^{-1}$$

which implies that the column vectors in U are linear combinations of the column vectors in X.

It should be noted that in some versions of Principal Component Analysis, the X matrix is decomposed into only two matrices $$X = LV$$

The L matrix is the product of the U and $\Sigma$ matrices, such that $$L^t L = \Lambda.$$

1.4.1 Multiple Linear Regression, Least Squares Regression

If y is a column vector of length n, and X is a matrix of dimension f by n, then the matrix equation $$y = X^t p + e$$

is a linear regression equation relating the dependent variable y to the independent variables X. p is a column vector of length f containing the regression coefficients, and e is the vector containing the residuals for the regression model. A least square regression is one that minimizes $e^t e$, i.e. the sum of the square of the residuals.

1.4.2 Solution for $f \leq n$

If X if f by n, y is of dimension n, and $f \leq n$, then the solution to the regression equation that minimizes $\|e\|$ is obtained by multiplying both sides of the equation in 1.4.1 by the left inverse of $X^t$, i.e.

$$y = X^t p + e \rightarrow (XX^t)^{-1} Xy = (XX^t)^{-1} XX^t p + (XX^t)^{-1} X e = p + (XX^t)^{-1} X e$$

The quanity $(XX^t)^{-1} Xy$ is the least square estimate of p, and is designated p.

$$\hat{p} = (XX^t)^{-1} Xy$$

The regression vector $\hat{p}$ is a linear combination of the column vectors in X. The estimates of y, i.e. y, are given by $$\hat{y} = X^t \hat{p} = X^t (XX^t)^{-1} Xy$$

The residuals for the model are $$e = y - \hat{y}$$

The Standard Error of Estimate (SEE) for the model is $$SEE = \sqrt{e^t e / (n - f)}$$

The regression model may be used to estimate the scalar value $y_u$ corresponding to a new vector of independent variables $x_u$ $$y_u = x_u^t p = x_u^t (XX^t)^{-1} Xy$$

Based on the model, the probability is $\alpha$ that the true value $y_u$ lies in range $$\hat{y}_u - t \cdot SEE \cdot \sqrt{1 + d^2} \leq y_u \leq \hat{y}_u + t \cdot SEE \cdot \sqrt{1 + d^2}$$

where t is the student's t distribution value for probability $\alpha$ and n-f degrees of freedom, and $d^2$ is given by $$d^2 = x_u^t (XX^t)^{-1} x_u$$

An equivalent solution for this case can be obtained using the singular value decomposition of $X^t$, i.e.

$$U \Sigma^{-1} V^t y = p + U \Sigma^{-1} V^t e$$

The solution can be seen to be equivalent since $$(XX^t)^{-1} X = (U \Sigma V^t V \Sigma U^t)^{-1} U \Sigma V^t = (U \Sigma^{-2} U^t) U \Sigma V^t = U \Sigma^{-1} V^t.$$

1.4.3 Solutions for $f > n$

If $f > n$, the matrix $X^t$ does not possess a left inverse since $XX^t$ is a f by f matrix of rank at most n. In this case, an approximate solution to the regression equations can be derived using methods such as Principal Components Regression or Partial Least Squares.

1.4.3.1 Principal Components Regression

Principal Components Regression (PCR) uses the singular value decomposition of the $X^t$ matrix to approximate a solution to the regression equation, i.e. the equation $$y = X^t p + e$$

is solved as $$U \Sigma^{-1} V^t y = U \Sigma^{-1} V^t X^t p + U \Sigma^{-1} V^t e = p + U \Sigma^{-1} V^t e$$

where U is of dimension f by k, $\Sigma$ and $\Sigma^{-1}$ are k by k, and V is n by k. The estimate of the regression vector is $$\hat{p} = U \Sigma^{-1} V^t y = X V \Sigma^{-2} V^t y$$

p is a linear combination of the column vectors of both U and X. The estimate of y is $$\hat{y} = X^t \hat{p} = X^t U \Sigma^{-1} V^t y = V \Sigma U^t U \Sigma^{-1} V^t y = V V^t y.$$

The residuals from the model are $$e = y - \hat{y} = y - V V^t y$$

The Standard Error of Estimate is $$SEE = \sqrt{e^t e / (n - k)}$$

For a new vector of independent variables $x_u$, the scalar estimate $y_u$ is obtained as $$y_u = x_u^t \hat{p} = x_u^t U \Sigma^{-1} V^t y = v_u^t V^t y \text{ where } v_u^t = x_u^t U \Sigma^{-1}$$

Based on the model, the probability is $\alpha$ that the true value $y_u$ lies in range $$\hat{y}_u - t \cdot SEE \cdot \sqrt{1 + d^2} \leq \hat{y}_u \leq y_u + t \cdot SEE \cdot \sqrt{1 + d^2}$$

where t is the student's t distribution value for probability $\alpha$ and n–k degrees of freedom, and $d^2$ is given by $$d^2 = x_u{}^t(XX^t)^{-1}x_u = v_u{}^t\Sigma U^t(U\Sigma V^tV\Sigma U^t)^{-1}U\Sigma v_u = v_u{}^t\Sigma U^t(U\Lambda U^t)^{-1}U\Sigma v_u$$

$$d^2 = v_u{}^t\Sigma U^tU\Lambda^{-1}U^tU\Sigma v_u = v_u{}^t\Sigma\Lambda^{-1}\Sigma v_u = v_u{}^tv_u$$

An alternative method for conducting Principal Component Regression involves decomposing the X matrix into $U\Sigma V^t$, and regressing y versus V, i.e.

$$X = U\Sigma V^t \text{ and } y = Vb + e$$

where b is a vector of regression coefficients. The solution is $$V^ty = V^tVb + V^te = b + V^te.$$

The estimate of the coefficients is $$\hat{b} = (V^tV)^{-1}V^ty = V^ty$$

The estimate $\hat{y}$ is $$\hat{y} = V\hat{b} = VV^ty$$

which is the same as obtained above. For a new vector of independent variables $x_u$, $v_u{}^t$ is calculated as $$v_u{}^t = x_u{}^tU\Sigma^{-1}$$

and the estimation of the scalar $\hat{y}_u$ is $$\hat{y}_u = v_u{}^t\hat{b} = v_u{}^tV^ty = x_u{}^tU\Sigma^{-1}V^ty = x_u{}^t\hat{p}$$

which is again the same as that obtained above. The residuals, SEE and $d^2$ are also the same as that shown for the first PCR method.

1.4.3.2 Step-wise and PRESS Regression

An advantage to using the alternative method for calculating a Principal Components Regression is that the coefficients $b_i$ which are small and statistically equivalent to zero may be detected and removed from the model (i.e. set to zero) prior to estimation of $\hat{y}$, thereby reducing the variation in the estimate. The coefficients which can be set to zero may be determined using, for example, a step-wise regression algorithm (2).

In the first step of a possible step-wise regression calculation, a series of equations of the form $$y = v_ib_i + e_i$$

where $v_i$ are the column vectors of the V matrix. The scalar coefficient $\hat{b}_i$ $$\hat{b}_i = v_i{}^ty$$

that produces the minimal sum of squares of residuals, $e_1{}^te_1$, is initially chosen. If $b_k$ is the coefficient that produced the minimum sum of square of residual, the 1st and $k^{th}$ columns of V are interchanged. The one variable model at the end of the first step is then $$y = v_1b_1 + e_1$$

In the second step, a series of equations of the form $$y = v_1b_1 + v_ib_i + e_i$$

are then constructed for each column vector $v_i$ where $i$ is not equal to 1. The equations are solved for the various combinations of $b_1$ and $b_i$, and the residual sum of squares $e_i{}^te_i$ is calculated for all the combinations. If $b_k$ is the coefficient that produced the minimum residual sum of squares, then $e_k{}^te_k$ is compared to $e_1{}^te_1$ via an F-test (3). If the inclusion of $b_k$ produces a statistically significant improvement in the sum of the squares of the residuals, the $2^{nd}$ and $k^{th}$ columns of V are interchanged. At the end of the second step, two variable model then becomes $$y = v_1b_1 + v_2b_2 + e_2$$

If no coefficient $b_k$ produces a statistically significant decrease in the sum of squares of the residuals, then the one variable model previously determined is the final model, and the step-wise procedure is completed.

If, at the end of the second step, a two variable model is found, a series of models of the form $$y = v_1b_1 + v_2b_2 + v_ib_i + e_i$$

are tested for all $i$ not equal to 1 or 2. If, in this third step, a coefficient $b_k$ is found such that $e_k{}^te_k$ is less than $e_2{}^te_2$ by a statistically significant amount, then the $3^{rd}$ and $k^{th}$ columns of V are interchanged, and the three variable model becomes $$y = v_1b_1 + v_2b_2 + v_3b_3 + e_3$$

At this point, models of the form $$y = v_1b_1 + v_3b_3 + e_{13}$$

$$y = v_2b_2 + v_3b_3 + e_{23}$$

are formed to test for deletion of variables from the model. If $e_{13}{}^te_{13}$ is less than $e_3{}^te_3$ by a statistically significant amount, then the $2^{nd}$ and $3^{rd}$ column vectors of V are interchanged and a new two variable model is obtained. Similarly, if $e_{23}{}^te_{23}$ is less than $e_3{}^te_3$ then the $1^{st}$ and $3^{rd}$ columns of V are interchanged to produce a new two variable model. At this point procedure then repeats the third step of testing possible three variable models. If a new three variable model which produces a statistically significant reduction in the sum of the squares of the residuals is found, tests are again conducted on deleting one of the three variables. If no new three variable model is found, the two variable model is the final model, and the step-wise procedure is finished. If a three variable model is generated from which no variables can be deleted, the third step is completed, and the procedure continues with a fourth step in which four variable models are tested. If a four variable model is generated from which no variables can be deleted, a fifth step is conducted to test five variable models. This step-wise procedure continues until no variables can be added or deleted to produce a statistically significant change in the residuals, or until all the k variables are included in the model, whichever comes first. Algorithms for efficiently conducting this step-wise procedure have been published (2).

An alternative to the step-wise regression calculation is a step-wise Predictive Residual Sum of Squares (PRESS) algorithm. This algorithm can also be used to determine which coefficients to include in the model. For PRESS, a model is built setting the $i^{th}$ dependent variable $y_i$, and the corresponding row vector, $v_i'$, to zero. The model has the form $$(y-y_i)=(V-v_i')b(i)+e$$

where $(y-y_i)$ is the vector obtained form y by setting $y_i$ to zero, and $(V-v_i')$ is the matrix obtained from V by setting the $i^{th}$ row to zero. For example, $$\text{if } y = \begin{pmatrix} y_1 \\ y_2 \\ y_3 \\ y_4 \end{pmatrix} \text{ and } V = \begin{pmatrix} v_{11} & v_{12} \\ v_{21} & v_{22} \\ v_{31} & v_{32} \\ v_{41} & v_{42} \end{pmatrix}$$

$$\text{then } (y - y_2) = \begin{pmatrix} y_1 \\ 0 \\ y_3 \\ y_4 \end{pmatrix} \text{ and } (V - v_2') = \begin{pmatrix} v_{11} & v_{12} \\ 0 & 0 \\ v_{31} & v_{32} \\ v_{41} & v_{42} \end{pmatrix}$$

The estimate of the coefficient vector for this model is $$\hat{b}(i)=[(V-v_i')'(V-v_i')]^{-1}(V-v_i')(y-y_i)$$

$$\hat{b}(i)=[(V'V)^{-1}+(V'V)^{-1}v_i(1-v_i'(V'V)^{-1}v_i)^{-1}v_i'(V'V)^{-1}](V-v_i')(y-y_i)$$

The estimate of $y_i$ based on this model, $\hat{y}(i)$, is then given by $$\hat{y}(i)=v_i'\hat{b}=v_i'[(V'V)^{-1}+(V'V)^{-1}v_i(1-v_i'(V'V)^{-1}v_i)^{-1}v_i'(V'V)^{-1}](V-v_i')(y-y_i)$$

The estimate may be simplified to yield $$\hat{y}(i)=(1-q_i)^{-1}\hat{y}_i-q_i(1-q_i)^{-1}y_i$$

where $$q_i=v_i'(V'V)^{-1}v_i$$

and $y_i$ is the estimate based on a model including all the variables $$\hat{y}_i=v_i'(V'V)^{-1}V'y.$$

The residual for the $i^{th}$ dependent variable is then $$y_i-\hat{y}(i)=(1-q_i)^{-1}(y_i-\hat{y}_i)$$

The PRESS statistic is the sum of these residuals over all $i=1$ to n.

The first step in the PRESS algorithm, n by 1 matrices $V_j$ are formed from the k columns of V. The n values of $q_i$ are calculated as $$q_i=v_i'(V_j'V_j)^{-1}v_i$$

and the residuals and PRESS values are calculated using the equations above. If $V_k$ is the matrix which yields the minimum value of PRESS, then the $1^{st}$ and the $k^{th}$ columns of V are interchanged.

In the second step, n by 2 matrices, $V_j$ are formed using the $1^{st}$ and $j^{th}$ ($j\neq 1$) columns of V. The $q_i$, residuals and PRESS values are again calculated. If no matrix $V_k$ yields a PRESS value less than that calculated in step 1, then the one variable model from the first step is the final model and the procedure is finished. If a $V_k$ is found that yields a smaller PRESS value, then the $2^{nd}$ and $k^{th}$ columns of V are interchanged, and a third step is conducted.

The third step involves forming n by 3 matrices $V_j$ using the $1^{st}$, $2^{nd}$ and $j^{th}$ ($j\neq 1,2$) columns of V. $q_i$, residuals, and PRESS values are again calculated. If no matrix $V_k$ yields a PRESS value lower than that calculated in step 2, then the two variable is the final model, and the procedure is finished. Otherwise, the $3^{rd}$ and $k^{th}$ columns of V are interchanged and the procedure continues.

The $m^{th}$ step in the n by m matrices $V_j$ using the $1^{st}$, $2^{nd}$, ... (m−1) and $j^{th}$ ($j\neq 1,2,\ldots,m-1$) columns of V, calculating $q_i$, the residuals and PRESS. If no matrices yield PRESS values less than that from the previous step, the model having m−1 variables is the final model, and the procedure is finished. If a matrix $V_k$ yields a PRESS value that is less than that calculated in the previous step, the $m^{th}$ and $k^{th}$ columns of V are interchanged, and another step is initiated.

A computer algorithm for efficiently doing a step-wise PRESS selection of variables was given by Allen (4).

Since the models calculated using these step-wise procedures may contain $k'<k$ nonzero coefficients, the degrees of freedom used in the calculation of SEE becomes $n-k'$, i.e.

$$SEE = \sqrt{e'e/(n-k')}$$

where e are the residuals for the final model. Based on the model, the probability is $\alpha$ that the true value $y_u$ lies in range $$\hat{y}_u - t' \cdot SEE \cdot \sqrt{1+d^2} \leq \hat{y}_u \leq y_u + t' \cdot SEE \cdot \sqrt{1+d^2}$$

where $t'$ is the student's t distribution value for probability $\alpha$ and $n-k'$ degrees of freedom, and $d^2$ is given by $$d^2=v_u'{}'v_u'$$

where v' is a vector of dimension k' obtained from v by deleting the elements whose corresponding coefficients were set to zero during the regression.

1.4.3.2 Partial Least Squares Regression

Partial Least Squares (PLS) Regression is similar to Principal Components Regression in that the f by n matrix X is decomposed into the product of orthogonal matrices, i.e.

$$X=LS'$$

where S is a n by k matrix, L is a f by k matrix. The matrices L and S have the following properties:

$$L'L=I$$

$$S'S=D$$

where D is a diaginal matrix. The dependent variable is regressed against one of these matrices, i.e.

$$y=Sb+e$$

PLS differs from PCR in the way that the matrices are determined. A step in the PLS regression proceeds by the following 10 calculations:

[1] A vector $u_1$ of dimension n is set equal to y, $u_1 = y$

[2] A weighting vector of dimension f is then calculated as $$w'_1 = Xu_1$$

[3] The weighting vector is normalized $$w_1 = w'_1 / \|w'_1\|$$

[4] A scores vector $s'_1$ of dimension n is calculated as $$s'_1 = X^t w_1$$

[5] A loadings vector of dimension f is calculated as $$l'_1 = X s'_1 / \|s'_1\|$$

[6] The loadings vector is normalized as $$l_1 = l'_1 / \|l'_1\|$$

[7] The scores vector is scaled as $$s_1 = s'_1 \|l_1\|$$

[8] The residuals for the X matrix are calculated as $$E_1 = X - ls^t$$

[9] A estimate of the coefficient $b_1$ is calculated from the relationship $$y = s_1 b_1 + e$$

$$\hat{b}_1 = (s_1' s_1)^{-1} s_1' y$$

[10] The residuals from the y vector are calculated as $$e_1 = y - s_1 b_1.$$

At this point, the a new vector $u_2$ is defined as the y residuals from the first step $$u_2 = e_1$$

and X is replaced by the X residuals from the first step, $E_1$. The vectors $w_2$, $s_2$, and $l_2$ and the coefficient $b_2$ are calculated in the same manner. The $i^{th}$ step through the algorithm involves equating $u_i$ to the residual vector from the previous step, $e_{i-1}$, substituting the residual matrix $E_{i-1}$ for the X matrix, and calculating $w_i$, $s_i$, and $l_i$. The procedure continues until the y residuals are sufficiently small, i.e. until $e_1^t e_i$ reaches the desired level of error for the model. The matrices L and S are formed from the column vectors $l_i$ and $s_i$, and the coefficient vector b from the scalars $b_i$.

The residuals from the model are $$e = y - \hat{y} = y - Sb = y - SS'y$$

The Standard Error of Estimate is $$SEE = \sqrt{e'e/(n-k)}$$

For a new vector of independent variables $x_u$, the scalar estimate $y_u$ is obtained as $$x_u = L s_u \rightarrow s_u = (L^t L)^{-1} L^t x_u = L^t x_u$$

$$y_u = s_u^t \hat{b} = s_u^t (S^t S)^{-1} S^t y$$

Based on the model, the probability is $\alpha$ that the true value $y_u$ lies in range $$\hat{y}_u - t \cdot SEE \cdot \sqrt{1 + d^2} \leq y_u \leq \hat{y}_u + t \cdot SEE \cdot \sqrt{1 + d^2}$$

where t is the student's t distribution value for probability $\alpha$ and $n-k$ degrees of freedom, and $d^2$ is given by $$d^2 = s_u^t (SS^t)^{-1} s_u$$

The PLS model can also be expressed in the form $$\hat{y} = X^t \hat{p}$$

where the regression vector $\hat{p}$ is $$\hat{p} = L\hat{b} = L(S^t S)^{-1} S^t y = XS(S^t S)^{-2} S^t y$$

The regression vector is a linear combination of the columns of X.

1.4.3.3 Cross Validation

The number of Principal Components or latent variables (i.e. the k dimension of the matrices U, $\Sigma$ and V for PCR and of L and S for PLS) which are to be used in PCR or PLS models can be tested using a cross validation procedure. The X matrix is split into two matrices $X_1$ and $X_2$ which are of dimension f by $n-j$ and f by j, respectively, where $1 \leq j \leq n/2$. y is similarly split into two corresponding vectors $y_1$ (dimension $n-j$) and $y_2$ (dimension j), e.g.

$$\text{if } X = \begin{pmatrix} x_{11} & x_{12} & x_{13} & x_{14} & x_{15} & x_{16} & x_{17} & x_{18} & x_{19} \\ x_{21} & x_{22} & x_{23} & x_{24} & x_{25} & x_{26} & x_{27} & x_{28} & x_{29} \\ x_{31} & x_{32} & x_{33} & x_{34} & x_{35} & x_{36} & x_{37} & x_{38} & x_{39} \\ x_{41} & x_{42} & x_{43} & x_{44} & x_{45} & x_{46} & x_{47} & x_{48} & x_{49} \end{pmatrix} \text{ and } y = \begin{pmatrix} y_1 \\ y_2 \\ y_3 \\ y_4 \\ y_5 \\ y_6 \\ y_7 \\ y_8 \\ y_9 \end{pmatrix},$$

then $$X_1 = \begin{pmatrix} x_{11} & x_{12} & x_{13} & x_{14} & x_{15} & x_{16} \\ x_{21} & x_{22} & x_{23} & x_{24} & x_{25} & x_{26} \\ x_{31} & x_{32} & x_{33} & x_{34} & x_{35} & x_{36} \\ x_{41} & x_{42} & x_{43} & x_{44} & x_{45} & x_{46} \end{pmatrix}, y_1 = \begin{pmatrix} y_1 \\ y_2 \\ y_3 \\ y_4 \\ y_5 \\ y_6 \end{pmatrix},$$

-continued $$X_2 = \begin{pmatrix} x_{17} & x_{18} & x_{19} \\ x_{27} & x_{28} & x_{29} \\ x_{37} & x_{38} & x_{39} \\ x_{47} & x_{48} & x_{49} \end{pmatrix}, y = \begin{pmatrix} y_7 \\ y_8 \\ y_9 \end{pmatrix}$$

$$X_1 = \begin{pmatrix} x_{11} & x_{12} & x_{13} & x_{17} & x_{17} & x_{19} \\ x_{21} & x_{22} & x_{23} & x_{27} & x_{28} & x_{29} \\ x_{31} & x_{32} & x_{33} & x_{37} & x_{38} & x_{39} \\ x_{41} & x_{42} & x_{43} & x_{47} & x_{48} & x_{49} \end{pmatrix}, y_1 = \begin{pmatrix} y_1 \\ y_2 \\ y_3 \\ y_7 \\ y_8 \\ y_8 \end{pmatrix},$$

$$X_2 = \begin{pmatrix} x_{14} & x_{15} & x_{17} \\ x_{24} & x_{25} & x_{26} \\ x_{34} & x_{35} & x_{36} \\ x_{44} & x_{45} & x_{46} \end{pmatrix}, y = \begin{pmatrix} y_4 \\ y_5 \\ y_6 \end{pmatrix}$$

$$X_1 = \begin{pmatrix} x_{14} & x_{15} & x_{16} & x_{17} & x_{18} & x_{19} \\ x_{24} & x_{25} & x_{26} & x_{27} & x_{28} & x_{29} \\ x_{34} & x_{35} & x_{36} & x_{37} & x_{38} & x_{39} \\ x_{44} & x_{45} & x_{46} & x_{47} & x_{48} & x_{49} \end{pmatrix}, y_1 = \begin{pmatrix} y_4 \\ y_5 \\ y_6 \\ y_7 \\ y_8 \\ y_9 \end{pmatrix},$$

$$X_2 = \begin{pmatrix} x_{11} & x_{12} & x_{13} \\ x_{21} & x_{22} & x_{23} \\ x_{31} & x_{32} & x_{33} \\ x_{41} & x_{42} & x_{43} \end{pmatrix}, y = \begin{pmatrix} y_1 \\ y_2 \\ y_3 \end{pmatrix}$$

would be three possible divisions of the matrices. Various models are built using $X_1$ and $y_1$, i.e. for PCR $$\hat{b} = V_1'y \text{ where } X_1 = U_1\Sigma_1V_1'$$

and for PLS $$\hat{b} = S_1'y_1 \text{ where } X_1 = L_1S_1'$$

The number of columns retained in the $V_1$ and $S_1$ matrices in the models is varied over the range to be tested. The models are used to estimate the values for $y_2$. For PCR, a matrix $V_2$ is calculated from $$X_2 = U_1\Sigma_1V_2', \quad V_2 = X_2'U_1\Sigma_1$$

and the estimates are made as $$\hat{y}_2 = V_2b$$

For PlS, a matrix $S_2$ is calculated from $$X_2 = L_1S_2', \quad S_2 = X_2'L_1$$

and the estimates are made as $$\hat{y}_2 = S_2b$$

The prediction residuals are calculated as $$e_p = y_2 - \hat{y}_2$$

The Predictive REsidual Sum of Squares for this step is $$PRESS = e_p'e_p$$

The procedure is repeated with different splits of X and y until each column of X and corresponding element in y have been in $X_2$ and $y_2$ once, e.g. using all three of the divisions of X and y show above. The total PRESS is the sum of the PRESS values calculated for each division. The optimum number of vectors to use in the model is that which minimizes the total PRESS.

1.4.3.4 Weighted Regression

In applying linear least squares regression techniques to solve the regression equation $$y = X'p + e$$

it is assumed that the elements of the residual vector are independent and normally distributed. In some applications, this assumption may not hold. For instance, if the elements $y_i$ of y are measured quantities, the error associated with the measurement of $y_i$ may depend on the magnitude of $y_i$. Alternatively, some of the individual $y_i$ values in y may represent the average of several measurements. In these cases, a weighted linear least square regression is used to develop the regression model.

If the quanity y is measured n times, then the average value $\bar{y}$ is $$\bar{y} = (y_1 + y_2 + \ldots + y_n)/n$$

The quantity $s^2$, $$s^2 = [(y_1 - \bar{y})^2 + (y_2 - \bar{y})^2 + \ldots + (y_n - \bar{y})^2]/(n-1)$$

is an unbiased estimate of the variance in the measurement of y. s is the standard deviation in the measurement. As n approached $\infty$, $s^2$ approaches the true variance.

If each of the $y_i$ elements in vector y was measured once, and the measurement of $y_i$ is known to have variance $s_i^2$, then the regression equation relating y (dimension n) to V (dimension n by k) that provides for normally distributed residuals is given by $$Wy = WVb + e$$

where W is a n by n diagonal matrix whose elements are $$w_{ii} = 1/s_i$$

The coefficients are estimated as $$\hat{b} = (V'W^2V)^{-1}VW^2y$$

The estimate $\hat{y}$ is $$\hat{y} = V\hat{b} = V(V'W^2V)^{-1}VW^2y$$

The residuals are $$e = y - \hat{y} = y - V(V'W^2V)^{-1}VW^2y = (I - V(V'W^2V)^{-1}VW^2)y$$

If the variance in the measurement of all individual $y_i$ is the same, and $\bar{y}$ is a vector of dimension n whose individual elements $\bar{y}_i$ represent the average of $n_i$ measurements, then the weighting matrix for weighted least squares regression of $\bar{y}_i$ against V is given by $$w_{ii} = \sqrt{n_i}$$

individual measurement of element $y_i$ is $s_i^2$, then the weighting matrix for weighted least squares is defined by $$w_{ii} = \sqrt{n_i}/s_i$$

2.0 Definitions Relating to Quantitative Spectral Measurements

If $i_o(f)$ is the intensity of electromagnetic radiation at frequency (wavelength) f which is incident on a sample, and i(f) is the intensity at the same frequency (wavelength) that is transmitted through the sample, then t(f), the transmission of the sample at frequency f is given by $$t(f) = i(f)/i_o(f)$$

The absorbance of the sample at frequency f is $$a(f) = -\log_{10}[t(f)]$$

The absorption spectrum of a sample will be represented by a vector x of dimension f whose individual elements are the absorbance of the sample at each of f frequencies (wavelengths). For convenience, the elements in x are generally ordered in terms of increasing or decreasing frequency.

Quantitative spectral analysis is based on Beer's Law (4). For a mixture of chemical components, Beer's Law can be represented by the matrix equation $$x = Act \text{ or } x/t = Ac$$

where A is an f by c matrix whose columns are the absorption spectra $a_i$ of the c individual pure components (measured at unit pathlength), where c is a vector whose elements are the concentrations of the components in the mixture, and where t is a scalar representing the pathlength (thickness) of the sample.

Beer's Law implies a linear relationship between the measured absorption spectrum, and the concentrations of mixture components. If the spectra of the components is known, the equation for Beer's Law can be solved for the component concentrations, i.e.

$$(A^tA)^{-1}A^tx/t = c$$

If y is a property of the sample that depends linearly on the concentrations of the sample components, then $$y = r^t c = r^t(A^tA)^{-1}A^tx/t$$

where r is the vector of coefficients that define the linear dependence. This expression indicates that there is a linear relationship between the property and absorption spectrum of the sample.

In general, the vectors in the matrix A are not known, and the relationship between component concentrations and/or properties and the sample spectrum is represented by $$y = p^tx = x^tp$$

where p is vector of dimension f that relates the spectrum to the desired concentration or property. The objective of quantitative spectral analysis is to define the vector p.

2.1 Calibration

Calibration is the process of creating a regression model to relate the component concentration and/or property data to the absorption spectra. The calibration of a spectral model will generally consist of the following steps:

[1] n representative samples of the materials for which the model is to be developed will be collected, their absorption spectra ($x_i$, $i=1,n$) will be obtained, and the component concentrations and/or property data ($y_i$, $i=1,n$) will be measured. The samples that are used in the calibration are referred to as references, and the spectra of these samples are referred to as reference spectra.

[2] A regression model of the form $$y = X^tp + e$$

will be constructed for each component and/or property which is to be modeled, where y is the vector of dimension n containing the individual concentration or property values for the n reference samples, and X if a f by n matrix whose columns are the spectra of the n reference samples measured at f frequencies (wavelengths). The mathematical method that is used in calculating the regression model will depend on the number of reference samples relative to the number of frequencies (wavelengths).

2.1.1 Calibration Models for $f \leq n$

If the number of reference samples, n, used in the calibration exceeds the number of frequencies per spectrum, f, then the calibration model can be obtained via linear least square regression (section 1.4.2).

$$y = X^tp + e \rightarrow (XX^t)^{-1}Xy = (XX^t)^{-1}XX^tp + (XX^t)^{-1}X\text{-}e = p + (XX^t)^{-1}Xe$$

The regression model could also be obtained using PCR or PLS, but in this case, these methods aren't required since the $(XX^t)$ matrix can be inverted.

If the number of frequencies (wavelengths) per spectrum, f, exceeds the number of reference samples, n, then a subset of f' frequencies can be chosen such that $f' \leq n$, and linear least square regression can be used to develop the calibration model.

$$y = X'^tp + e \rightarrow (X'X'^t)^{-1}X'y = p + (X'X'^t)^{-1}X'e$$

where X' is the f' by n matrix obtained from X by deleting the f-f' rows. The choice of the frequencies (wavelengths) that are to be used in developing the regression model can be based on a prior knowledge of the component absorptions present in the spectra (i.e. spectroscopy expertise), or they can be chosen using a statistical wavelength (frequency) selection algortihm (5).

If the concentration and/or property data in y does not have uniform measurement variance, and/or represents the average of differing numbers of experimental measurements, then the calibration model can be developed using a weighted linear least squares regression (section 1.4.3.4).

2.1.2 Calibration Models for $f \geq n$

If the number of frequencies per spectrum, f, exceeds the number of reference spectra used in the calibration, n, then the calibration model can be built using either Principal Components Regression (section 1.4.3.1)

$$y = X^t p + e \rightarrow U\Sigma^{-1} V^t y = U\Sigma^{-1} V^t X^t p + U\Sigma^{-1} V^t e = p + U\Sigma^{-1} V^t e$$

or via Partial Least Square Regression (section 1.4.3.2)

$$y = X^t p + e \rightarrow X = LS^t, \hat{b} = (S^tS)^{-1} S^t y \rightarrow \hat{p} = L\hat{b}$$

For Principal Components Regression, the model may be developed using a two step calculation $$X = U\Sigma V^t, y = Vb \rightarrow \hat{p} = U\Sigma^{-1} V^t y = XV\Sigma^{-2} V^t y = XV\Sigma^{-2} \hat{b}$$

where the nonzero coefficients, $b_i$, which are used in the model may be determined using step-wise or PRESS based regressions (section 1.4.3.2). If the individual component concentrations and/or properties in y are of unequal measurement variance, or represent the average of unequal numbers of experimental determinations, then the step-wise or PRESS based regression may be conducted using the matrices from the weighted least squares regression (section 1.4.3.4).

2.2 Analysis of Unknowns

All of the above mentioned calibration models can be expressed in the form $$\hat{y} = X^t \hat{p}$$

The models differ in the means used to estimate the regression vector p. If $x_u$ represents the spectrum of a new, unknown material, then the component concentrations and/or properties estimated using the model are $$y_u = x_u^t p$$

The use of the calibration model to estimate component concentrations and/or properties is referred to as analysis.

3.0 Constrained Spectral Analysis

The spectrum measured for a sample, x, generally represents the superposition of the absorptions due to the sample components, $x_c$, and signals arising from the process involved in making the spectral measurement, m.

$$x = x_c + m$$

The signal arising from the measurement process may be the sum of various individual signals, $m_i$ $$x = x_c + m_1 + m_2 + \ldots + m_s$$

Examples of these measurement process signals would include, but not be limited to,

[1] reflection and/or scattering loses from the windows of the cell used to contain the sample, or in the case of free-standing samples, from the front surface of the sample;

[2] variations in the spectral baseline arising from variations in the intensity (temperature) of the spectrometer sourse and/or the responsivity of the spectrometer detector;

[3] absorption signals arising from gas phase components (e.g. water vapor and carbon dioxide) that are present in the light path through the spectrometer, but are not sample components. Since the regression vectors calculated from the calibration are in all cases linear combinations of the original spectra, i.e.

for linear least squares, $\hat{p} = X^t(XX^t)^{-1}Xy$
for PCR, $\hat{p} = U\Sigma^{-1} V^t y = XV\Sigma^{-2} V^t y$
and for PLS, $\hat{p} = L\hat{b} = XS(S^tS)^{-1}b$ they will include contribution from the measurement process signals, m. As such, the estimation of component concentrations and/or property values based on $$\hat{y}_u = x_u^t \hat{p}$$

will vary not only with changes in the absorptions due to real sample components, but also with variations in the signals arising from the measurement process. The calibration models are thus not robust relative to variations in the signals arising from the measurement process.

The estimation of component concentrations and/or properties can be expressed $$\hat{y}_u = x_u^t \hat{p} = x_c^t \hat{p} + m^t \hat{p}$$

The estimation will be insensitive to variations in the signals arising from the measurement process if, and only if, the second term, $m^t p$, is equal to zero, i.e. if the regression vector is orthogonal to the signals arising from the measurement process.

2.1 Constrained Linear Least Squares

If X is an f by n matrix containing the spectra of the reference samples, X can be represented as the sum $$X = X_c + MN^t$$

where M is a f by s matrix containing the individual signals arising from the measurement process as columns, and N is a n by s matrix containing the scalar elements $n_{ij}$ which correspond to the level of the $j^{th}$ measurement process signal for the $i^{th}$ reference sample. If $f < n$ (or if $f' < n$ frequencies are chosen), then the solution to the calibration model $$y = X^t p + e$$

which yields a regression vector p which is orthogonal to the measurement process signals M is derived via a constrained least squares regression, where the constrain equation is $$M^t p = 0$$

where 0 is a zero vector. X' is defined as the f by n+s matrix obtained by adding the s columns of M to X, and y' is the vector of dimension n+s obtained by adding a corresponding s zero elements to y. The constrained least square solution is then $$\hat{p} = (XX^t)^{-1}X'y' - (XX^t)^{-1}M(M^tM)^{-1}M^tX'y'$$

$$\hat{p} = (XX^t)^{-1}[I - M(M^tM)^{-1}M^t]X'y'$$

$$\hat{p} = [I - M(M^tM)^{-1}M^t](XX^t)^{-1}X'y'$$

The estimate $\hat{y}$ is then $$\hat{y} = X^t\hat{p} = X_c{}^t\hat{p} + NM^t\hat{p}$$

$$\hat{y} = X_c{}^t[I - M(M^tM)^{-1}M^t](XX^t)^{-1}X'y' \\ + NM^t[I - M(M^tM)^{-1}M^t](XX^t)^{-1}X'y'$$

$$\hat{y} = X_c{}^t[I - M(M^tM)^{-1}M^t](XX^t)^{-1}X'y' + NM^t \\ (XX^t)^{-1}X'y' - NM^tM(M^tM)^{-1}M^t(XX^t)^{-1}X'y'$$

$$\hat{y} = X_c{}^t[I - M(M^tM)^{-1}M^t](XX^t)^{-1}X'y' + NM^t \\ (XX^t)^{-1}X'y' - NM^t(XX^t)^{-1}X'y'$$

$$\hat{y} = X_c{}^t[I - M(M^tM)^{-1}M^t](XX^t)^{-1}X'y'$$

The estimate $\hat{y}$ is constrained to be independent of the presence of the measurement process signals. Similarly, it $x_u$ is a spectrum of a new unknown sample, such that $$x_u = x_c + Mn$$

then the estimation of $\hat{y}_u$ is $$\hat{y}_u = x_u{}^t\hat{p} = (x_c + Mn)^t\hat{p}$$

$$\hat{y}_u = x_c{}^t[I - M(M^tM)^{-1}M^t](XX^t \\ )^{-1}X'y' + nM^t[I - M(M^tM)^{-1}M^t](XX^t)^{-1}X'y'$$

$$\hat{y}_u = x_c{}^t[I - M(M^tM)^{-1}M^t](XX^t)^{-1}X'y'$$

i.e. the estimate is independent of the presence of the measurement process signals in the spectrum $x_u$. The residuals from the model are $$e = y - \hat{y} = y - X^t[I - M(M^tM)^{-1}M^t](XX^t)^{-1}X'y'$$

The Standard Error of Estimate is $$SEE = \sqrt{e^te/(n - f)}$$

Based on the model, the probability is $\alpha$ that the true value $y_u$ lies in range $$\hat{y}_u - t \cdot SEE \cdot \sqrt{1 + d^2} \leq y_u \leq \hat{y}_u + t \cdot SEE \cdot \sqrt{1 + d^2}$$

where t is the student's t distribution value for probability $\alpha$ and $n-f$ degrees of freedom, and $d^2$ is given by $$d^2 = x_u{}^t(XX^t)^{-1}M[M^t(M^tM)^{-1}M]^{-1}M^tx_u$$

2.2 Constrained Principal Components Regression

If $f > n$, then the constrained linear least squares solution in section 2.1 cannot be used since the matrix $XX^t$ is at most of rank n, is singular, and cannot be directly inverted. It is possible to develop a constrained principal components model by following a similar methodology. If $X'$ again represents the f by $n+s$ matrix whose first s columns are measurement process signals, M, and whose last n columns are the reference spectra, then the singular value decomposition of $X'$ is $$X' = U'\Sigma'V'^t$$

where $U'$ is an f by k matrix, $\Sigma'$ is the k by k matrix of singular values and $V'$ is an $n+s$ by k matrix. The s by k matrix $V_m$ corresponds to the first s rows of $V'$, i.e. to the right eigenvectors associated with the signals due to the measurement process. The measurement process signals can be expressed as $$M = U'\Sigma'V_m{}^t$$

If $y'$ is the vector containing the s zeros and the n concentration or property values, then the regression $$y' = Vb + e$$

subject to the constraint $$V_m b = 0$$

yields estimated coefficients of the form $$\hat{b} = [I - V_m{}^t(V_m V_m{}^t)^{-1}V_m](V^tV)^{-1}V^t \\ y' = [I - V_m{}^t(V_m V_m{}^t)^{-1}V_m]V^ty'$$

The regression vector is then $$\hat{p} = U'\Sigma'^{-1}[I - V_m{}^t(V_m V_m{}^t)^{-1}V_m]V^ty'$$

$$\hat{p} = U'\Sigma'^{-1}V^ty' - U'\Sigma'^{-1}V_m{}^t(V_m V_m{}^t)^{-1}V_mV^ty'$$

The estimate $\hat{y}$ for the model is $$\hat{y} = X^t\hat{p} = X_c{}^t\hat{p} + NM^t\hat{p}$$

$$\hat{y} = X_c{}^t[U'\Sigma'^{-1}V^ty' - U'\Sigma'^{-1}V_m{}^t(V_m V_m{}^t \\ )^{-1}V_mV^ty'] \\ + NM^t[U'\Sigma'^{-1}V^ty' \\ - U'\Sigma'^{-1}V_m{}^t(V_m V_m{}^t)^{-1}V_mV^ty']$$

$$\hat{y} = X_c{}^t[U'\Sigma'^{-1}V^ty' - U'\Sigma'^{-1}V_m{}^t(V_m V_m{}^t \\ )^{-1}V_mV^ty'] \\ + NV_m\Sigma'U'^t[U'\Sigma'^{-1}V^ty' - U' \\ \Sigma'^{-1}V_m{}^t(V_m V_m{}^t)^{-1}V_mV^ty']$$

$$\hat{y} = X_c{}^t[U'\Sigma'^{-1}V^ty' - U'\Sigma'^{-1}V_m{}^t(V_m V_m{}^t \\ )^{-1}V_mV^ty'] + NV_m\Sigma'U'^tU'\Sigma'^{-1}V^ty' - NV_m \\ \Sigma'U'^tU'\Sigma'^{-1}V_m{}^t(V_m V_m{}^t)^{-1}V_mV^ty'$$

$$\hat{y} = X_c{}^t[U'\Sigma'^{-1}V^ty' - U'\Sigma'^{-1}V_m{}^t(V_m V_m{}^t \\ )^{-1}V_mV^ty'] + \\ NV_mV^ty' - NV_mV_m{}^t(V_m V_m{}^t)^{-1}V_mV^ty'$$

$$\hat{y} = X_c{}^t[U'\Sigma'^{-1}V^ty' - U'\Sigma'^{-1}V_m{}^t(V_m V_m{}^t \\ )^{-1}V_mV^ty']$$

The estimated concentration and property values are constrained to be independent of the signals that are due to the measurement process.

For an unknown material with spectrum $x_u$, $$x_u = x_c + Mn = x_c + U'\Sigma'V_m{}^tn \rightarrow \hat{y}_u = x_u{}^t\hat{p} = (x_c \\ + Mn)^t\hat{p}$$

$$\hat{y}_u = x_c{}^t[U'\Sigma'^{-1}V^ty' - U'\Sigma'^{-1}V_m{}^t \\ (V_m V_m{}^t)^{-1}V_mV^ty'] + nM^t[U'\Sigma'^{-1}V^ty' - U' \\ \Sigma'^{-1}V_m{}^t(V_m V_m{}^t)^{-1}V_mV^ty']$$

$$\hat{y}_u = x_c{}^t[U'\Sigma'^{-1}V^ty' - U'\Sigma'^{-1}V_m{}^t \\ (V_m V_m{}^t)^{-1}V_mV^ty'] + nV_m\Sigma'U'^tU'\Sigma'^{-1}V^t \\ y' - nV_m\Sigma'U'^tU' \\ \Sigma'^{-1}V_m{}^t(V_m V_m{}^t)^{-1}V_mV^ty'$$

$$\hat{y}_u = x_c{}^t[U^t\Sigma'^{-1}V^ty' - U^t\Sigma'^{-1}V_m{}^t (V_mV_m{}^t)^{-1}V_mV^ty']$$

The estimated concentrations and properties are independent of the measurement process signal. The residuals from the model are $$e = y - \hat{y} = y - X^t\hat{p} = y - X^tU^t\Sigma'^{-1}[I - V_m{}^t(V_mV_m{}^t)^{-1}V_m]V^ty'$$

The Standard Error of Estimate is $$SEE = \sqrt{e^te/(n-k)}$$

Based on the model, the probability is $\alpha$ that the true value $y_u$ lies in range $$\hat{y}_u - t \cdot SEE \cdot \sqrt{1 + d^2} \leq y_u \leq \hat{y}_u + t \cdot SEE \cdot \sqrt{1 + d^2}$$

where t is the student's t distribution value for probability $\alpha$ and $n - f$ degrees of freedom, and $d^2$ is given by $$d^2 = v_u[I - V_m{}^t(V_mV_m{}^t)^{-1}V_m]v_u{}^t$$

The Constrained Principal Components Regression described above will yield a stable calibration model that is robust to variations in the intensity of signals arising from the measurement process provided that the scaling of the measurement process signals in M is sufficiently large that principal components corresponding to these measurement process signals are retained in the first k principal components that are used in the model. If the scaling of the signals in M is too small, then the matrix $V_mV_m{}^t$ will be singular and cannot be inverted.

An alternative, equivalent, and preferred method for developing a Constrained Principal Components model involves orthogonalizing the spectra in X to the measurement process signals in M prior to the development of the model. X is a f by n matrix containing the spectra of the n reference samples at f frequencies. M is a f by s matrix containing the spectra of the s measurement process signals at the f frequencies. The first step in the process is to derive a set of orthogonal vectors, the columns of the matrix $U_m$, that represent the original measurement process signals in M. This can be accomplished by either using a Gram-Schmidt orthogonalization procedure, a singular value decomposition of M, or some combination of the two. For example, the singular value decomposition of M would yield $$M = U_m\Sigma_m V_m{}^t$$

where $U_m$ is f by s, $\Sigma$ is s by s, and $V_m$ is s by s. Each spectrum in X is then orthogonalized to the columns of $U_m$ to obtain the corrected spectra, $X_c$. If $x_1$ is the first spectrum in X, and $u_1, u_2, \ldots u_s$ are the orthogonalized measurement process signals, then the first corrected spectrum, $c_1$, is given by $$c_1 = x_1 - u_1(u_1{}^tx_1) + u_2(u_2{}^tx_1) + \ldots + u_s(u_s{}^tx_1)$$

The matrix form of this orthogonalization is $$X_c = X - U_mU_m{}^tX$$

where the individual corrected spectra, $c_i$, are the columns of the $X_c$ matrix. The original spectral matrix is given by $$X = X_c + U_mU_m{}^tX$$

In the next step, the singular value decomposition of $X_c$ is then obtained as $$X_c = U_c\Sigma_c V_c{}^t$$

The regression model can then be obtained directly as $$y = X_c{}^tp + e \rightarrow \hat{p} = U_c\Sigma_c{}^{-1}V_c{}^ty$$

or indirectly by using the relationship $$y = V_cb + e \rightarrow \hat{b} = V_c{}^ty$$

The estimate $\hat{y}$ from the model is $$\hat{y} = X^t\hat{p} = X^tU_c\Sigma_c{}^{-1}V_c{}^ty = (X_c + U_mU_m{}^tX)^tU_c \Sigma_c{}^{-1}V_c{}^ty$$

$$\hat{y} = X_c{}^tU_c\Sigma_c{}^{-1}V_c{}^ty + X^tU_mU_m{}^tU_c \Sigma_c{}^{-1}V_c{}^ty = X_c{}^tU_c\Sigma_c{}^{-1}V_c{}^ty$$

The term containing the product $U_m{}^tU_c$ is zero since the columns of $U_c$ are linear combinations of the columns of $X_c$ which where generated to be orthogonal to the columns of $U_m$. The estimate is constrained to be insensitive to the intensity of the measurement process signals in X. The residuals for the model are $$e = y - \hat{y} = y - X_c{}^tU_c\Sigma_c{}^{-1}V_c{}^ty$$

The Standard Error of Estimate for the model is $$SEE = \sqrt{e^te/(n-k)}$$

For a new unknown sample with spectrum $x_u$ which unknown measurement process signals nM, the estimate of $\hat{y}_u$ is $$\hat{y}_u = x_u{}^t\hat{p} = (x_c{}^t + Mn)^tU_c\Sigma_c{}^{-1}V_c{}^ty = (x_c{}^t + U_m\Sigma_mV_m{}^tn)^tU_c\Sigma_c{}^{-1}V_c{}^ty$$

$$\hat{y}_u = x_c{}^tU_c\Sigma_c{}^{-1}V_c{}^ty + nV_m\Sigma_mU_m{}^tU_c \Sigma_c{}^{-1}V_c{}^ty = x_c{}^t U_c\Sigma_c{}^{-1}V_c{}^ty = v_c{}^tV_c{}^ty$$

where $$v_c{}^t = x_c{}^tU_c\Sigma_c{}^{-1}$$

The estimate depends only on the portions of the spectra arising from the component absorptions, $x_c$, and is independent of the measurement process signals. Based on the model, the probability is $\alpha$ that the true value $y_u$ lies in range $$\hat{y}_u - t \cdot SEE \cdot \sqrt{1 + d^2} \leq y_u \leq \hat{y}_u + t \cdot SEE \cdot \sqrt{1 + d^2}$$

where t is the student's t distribution value for probability $\alpha$ and n-f degrees of freedom, and $d^2$ is given by $$d^2 = v_c{}^tv_c$$

Individual $b_i$ used in the regression of y versus $V_c$ can be set to zero based on the results of a step-wise or PRESS based regression if doing so does not result in a statistically significant increase in the residual sum of squares. If the individual elements of y represent measurements having differing measurement variance, or are the averages of differing numbers of measurements, the regression of y versus $V_c$ can be accomplished using a weighted regression. In the weighted regression, a step-wise or PRESS based algorithm can again be employed to test whether individual coefficients can be set to zero.

The equivalence of the two methods of calculating a Constrained Principal Components Regression model can be demonstrated as follows: If the first s columns of $X'$ that correspond to the measurement process signals M are scaled by a sufficiently large value such that the variance due to M (the sum of the diagonal elements of $M^tM$) is much larger than the variance due to the reference spectra (the sum of the diagonal elements of $X^tX$) then the first s Principal Components of $X'$ will be $U_m$, and the remaining k Principal Components will be $U_c$, i.e.

$$X' = U\Sigma'V'^t = (U_m, U_c)(\Sigma_m, \Sigma_c)(V_m, V_c)^t$$

where $(U_m, U_c)$ is an f by s+k matrix whose first s columns are $U_m$ and whose last k columns are $U_c$, $(\Sigma_m, \Sigma_c)$ is an s+k by s+k matrix whose first s diagonal elements are from $\Sigma_m$ and whose last k diagonal elements are from $\Sigma_c$, and $(V_m, V_c)$ is an s+k by s+n matrix whose first s columns are $V_m$ and whose last n columns are $V_c$. The regression vector is then $$\hat{p} = U\Sigma'^{-1}V'y' - U\Sigma'^{-1}V_m^t(V_mV_m^t)^{-1}V_mV'y'$$

$$\hat{p} = (U_m, U_c)(\Sigma_m, \Sigma_c)^{-1}(V_m, V_c)^t y' - (U_m, U_c)(\Sigma_m, \Sigma_c)^{-1}V_m^t (V_mV_m^t)^{-1}V_m(V_m, V_c)^t y'$$

$$\hat{p} = U_m\Sigma_m^{-1}V_m^ty_m + U_c\Sigma_c^{-1}V_c^ty - U_m\Sigma_m^{-1}V_m^t(V_mV_m^t)^{-1}V_mV_m^ty_m - U_c\Sigma_c^{-1}V_m^t(V_mV_m^t)^{-1}V_mV_c^ty'$$

$$\hat{p} = U_m\Sigma_m^{-1}V_m^ty_m + U_c\Sigma_c^{-1}V_c^ty - U_m\Sigma_m^{-1}V_m^ty_m = U_c\Sigma_c^{-1}V_c^ty$$

where the term $U_c\Sigma_c^{-1}V_m^t(V_mV_m^t)^{-1}V_mV_c^ty'$ is zero since the columns of $V_m$ and $V_c$ are orthogonal. The Constrained Principal Components model obtained using the constrained regression method is equivalent to that obtained using the preorthogonaliztion method providing the scaling of the measurement process signals is large enough to ensure that they are included in Principal Components that are retained from the singular value decomposition of $X'$. The preorthogonalization method is preferred since it avoids the necessity of determining an appropriate scaling for the measurement process signals, and it avoids potential computer round off errors which can result if the scaling of the measurement process signals is too large relative to the scaling of the spectra.

Constrained Principal Components Regression can be employed in the case where $f \leq n$, but it is not required since the matrices required for solving the constrained linear least squares model can be inverted.

2.2 Constrained Partial Least Squares Regression

If $f > n$, then the constrained linear least squares solution in section 2.1 cannot be used since the matrix $XX^t$ is at most of rank n, is singular, and cannot be directly inverted. It is possible to develop a constrained partial least squares model by following a similar methodology. X is a f by n matrix containing the spectra of the n reference samples at f frequencies. M is a f by s matrix containing the spectra of the s measurement process signals at the f frequencies. The first step in the development of the constrained partial least square model is to derive a set of orthogonal vectors, the columns of the matrix $U_m$, that represent the original measurement process signals in M. This can be accomplished by either using a Gram-Schmidt orthogonalization procedure, a singular value decomposition of M, or some combination of the two. For example, the singular value decomposition of M would yield $$M = U_m\Sigma_m V_m^t$$

where $U_m$ is f by s, $\Sigma$ is s by s, and $V_m$ is s by s. Each spectrum in X is then orthogonalized to the columns of $U_m$ to obtain the corrected spectra, $X_c$. If $x_1$ is the first spectrum in X, and $u_1, u_2, \ldots u_s$ are the orthogonalized measurement process signals, then the first corrected spectrum, $c_1$, is given by $$c_1 = x_1 - u_1(u_1^t x_1) + u_2(u_2^t x_1) + \ldots + u_s(u_s^t x_1)$$

The matrix form of this orthogonalization is $$X_c = X - U_m U_m^t X$$

where the individual corrected spectra, $c_i$, are the columns of the $X_c$ matrix. The original spectral matrix is given by $$X = X_c + U_m U_m^t X$$

A partial least squares model is then developed to relate $X_c$ and y $$X_c = L_c S_c^t \rightarrow y = S_c b + e$$

where S is a n by k matrix, L is a f by k matrix. The model is developed using the methodology described in section 1.4.3.2. The regression vector obtained is $$\hat{p} = L_c \hat{b} = X_c S_c (S_c^t S_c)^{-1} S_c^t y$$

The estimate $\hat{y}$ based on the model is $$\hat{y} = X^t \hat{p} = (X_c + MN)^t \hat{p} = (X_c + U_m\Sigma_m V_m^t N)^t \hat{p}$$
$$\hat{p} = X_c^t \hat{p} + (U_m\Sigma_m V_m^t N)^t \hat{p}$$

$$\hat{y} = X_c^t X_c S_c(S_c^t S_c)^{-1} b + N^t V_m \Sigma_m U_m^t X_c S_c (S_c^t S_c)^{-1} b = X_c^t X_c S_c(S_c^t S_c)^{-1} b$$

where the term $N^t V_m \Sigma_m U_m^t X_c S_c (S_c^t S_c)^{-1} b$ is zero since the columns of $U_m$ are orthogonal to the columns of $X_c$. The estimate y is constrained to be independent of the measurement process signals. The residuals from the model are $$e = y - \hat{y} = y - X_c^t X_c S_c(S_c^t S_c)^{-1} b$$

The Standard Error of Estimate for the model is $$SEE = \sqrt{e^t e/(n-k)}$$

For a new spectrum, $x_u$, which contains component absorptions $x_c$ and measurement process signals Mn, the scalar estimate $y_u$ is obtained as $$s_u = (L_c^t L_c)^{-1} L_c^t x_u = (L_c^t L_c)^{-1} L_c^t (x_c + Mn) = (L_c^t L_c)^{-1} L_c^t (x_c + U_m \Sigma_m V_m^t n)$$

$$s_u = (L_c^t L_c)^{-1} L_c^t x_c = L_c^t x_c$$

$$y_u = s_u^t b = x_c^t L_c (S_c^t S_c)^{-1} S_c^t y$$

The estimate of $y_u$ is constrained so as to be independent of an measurement process signals in $x_u$. Based on the model, the probability is $\alpha$ that the true value $y_u$ lies in range $$\hat{y}_u - t \cdot SEE \cdot \sqrt{1 + d^2} \leq y_u \leq \hat{y}_u + t \cdot SEE \cdot \sqrt{1 + d^2}$$

where t is the student's t distribution value for probability $\alpha$ and $n-k$ degrees of freedom, and $d^2$ is given by $$d^2 = s_u^t (S_c S_c^t)^{-1} s_u$$

3.0 Pathlength and Scaling Constraints

The matrix form of Beer's Law can be represented by the equation $$X = ACT \text{ or } XT^{-1} = AC \text{ or } (A^tA)^{-1}A^tXT^{-1} = C \rightarrow C^t = T^{-1}X^tA(A^tA)^{-1}$$

where X is the f by n matrix containing the reference spectra used in the development of spectral calibrations, A is an f by c matrix hose columns are the absorption spectra $a_i$ of the c individual components (measured at or normalized to unit pathlength), where C is a c by n matrix whose general element $c_{ij}$ is the concentration of the $i^{th}$ component in the $j^{th}$ reference sample, and where T is a diagonal n by n matrix containing the pathlengths for the n samples.

If y is a component concentration or a property that depends linearly on the concentrations of all the sample components, then $$y = C^t r$$

where r is a vector of dimension c which the coefficients relating y to the concentrations of the individual components. If y is the concentration of a single component, the only the one corresponding element of r will be nonzero. If y is the concentration of a "lumped" component (e.g. the total aromatics content of a hydrocarbon which equals the sum of the concentrations of the individual aromatic components), then the elements of r which correspond to the components that were "lumped" will be one, and the remaining elements of r will be zero. If y is a physical property (i.e. a property that depends on the physical state of the samples, e.g. the sample density measured at a specified temperature) or a performance property (i.e. a property that is defined by the use of the sample in an application, e.g. the research octane number of a gasoline as defined by ASTM 2699-84 (6), or the reactivity of the sample under a defined set of conditions), then r contains the coefficients that relate the property to all of the individual components. The regression models that are developed above have the form $$y = C^t r + e = T^{-1} X^t A (A^t A)^{-1} r = T^{-1} X^t p + e \rightarrow A (A^t A)^{-1} r = p$$

If all the reference spectra are collected at the same pathlength, then T and $T^{-1}$ are the products of scalars times the unit matrix I, and the regression equation becomes $$y = T^{-1} X^t A (A^t A)^{-1} r + e = I X^t A (A^t A)^{-1} r t = X^t p + e \rightarrow A (A^t A)^{-1} r t = p$$

where t is the pathlength used in all the measurements. In this case, the scalar t is lumped into the overall regression vector that is determined in the calibration. During the analysis, the unknown spectrum must be collected at the same pathlength, or if it is collected at a different pathlength $t'$, either the spectrum $x_u$ or the estimated value $y_u$ must be scaled by the ratio $t/t'$.

If all the reference spectra are not collected at the same pathlength, then the spectra can be normalized prior to the calibration, $$X_n = XT^{-1}$$

and the regression model can built relating the normalized data $X_n$ to y. In this case, during the analysis, either the unknown spectrum $x_u$ or the initial estimate of $y_u$, must be scaled by $1/t'$ (the pathlength used in the collection of $x_u$) to obtain the final estimate.

The sum of all the individual components in the sample must equal unity, i.e. they must account for the total sample. If r is a vector containing all ones, then y is also $$y = C^t r = C^t 1 = 1$$

where 1 indicates a vector containing all ones. In this case, a regression of the form $$y = 1 = T^{-1} X^t p_t \rightarrow 1 T = X^t p_t \rightarrow t = X^t p_t$$

where t is a vector containing the pathlengths used in the measurement of the n reference samples. $p_t$ is a regression vector that can be used to estimate the pathlength used in the measurement of the spectrum of an unknown, i.e.

$$\hat{t} = x_u^t p_t$$

The use of a regression model to estimate the pathlength at which a spectrum was collected assumes that all the components in the sample contribute a measurable absorption to the spectrum. If a component possesses no absorptions in the spectral range used in the calibration, then an increase or decrease in the concentration of the component produces at most a change in the scaling of the spectrum (via changing the concentrations of the other components where the sum of the component concentrations sums to unity, i.e. dilution effects), and cannot be distinguished from a scaling change associated with varying the pathlength. The assumption required for use of a pathlength regression is valid for mid- and near-infrared spectroscopies where all typical sample components are expected to give rise to some vibrational absorption, but it would not hold for ultraviolet-visible spectroscopy where some components might possess no measurable absorption. If reference and unknown samples are diluted in solvent for the collection of the IR spectra, the pathlength regression can still be applies since the solvent can be considered as an additional sample component.

The results of a pathlength regression model can be incorporated into the calibration models built for the estimation of component concentrations and/or properties. If X is the matrix containing reference spectra collected at pathlengths t, then a regression model can be constructed to estimate $\hat{t}$ $$t = X^t p_t + e \rightarrow \hat{t} = X^t \hat{p}_t$$

where $p_t$ can be estimated using Linear Least Square Regression, Principal Components Regression, Partial Least Squares Regression, or more preferably Constrained Linear Least Squares Regression, Comstrained Principal Components Regression or Contrained Partial Least Squares Regression. The matrix $\hat{T}$ is defined as a diagonal matrix whose element $\hat{t}_{ii}$ is the estimate $\hat{t}_i$ from $\hat{t}$, i.e. the $\hat{t}_{ii}$ is the estimated pathlength for the $i^{th}$ sample. Regression models for component concentrations and/or properties can be developed using the equation $$y = \hat{T}^{-1} X^t p + e = X_t^t p + e$$

where $X_t$ is the reference spectral data scaled by the estimated pathlengths.

For Linear Least Squares Regression, or Constrained Linear Least Squares Regression, the incorporation of the pathlength regression into the calibration is relatively straight forward. A model is built based on the raw reference spectra, X, and the pathlengths, t. The model is applied to the reference spectra to estimate the pathlengths, $\hat{t}$. The estimated pathlengths are used to calculate $\hat{T}$ and to rescale the data to obtain $X_t$. Models are then built for all the components and/or properties y based on the rescaled spectral data, $X_t$. During the analysis, the pathlength used in the collection of the spectrum of the unknown, $\hat{t}_u$, is estimated, and either the spectrum of the unknown, or the initial estimates of the component concentrations and/or properties are scaled by $1/\hat{t}_u$.

In Partial Least Squares Regression and Constrained Partial Least Squares regression, the pathlength, component concentration, or property values are used in the calculation of the decomposition of X. The matrices L and S which are calculated are different for each component, property and for pathlength. Separate models must thus be constructed for pathlength and for components and properties. A general calibration procedure would involve, developing a model for the pathlengths t based on the raw reference spectra X. Using the estimates $\hat{t}$ to construct the $\hat{T}$ matrix and scaling X to obtain $X_t$. Building regression models for each component and/or property y based on $X_t$. In the analysis of a spectrum $x_u$ of an unknown, the pathlength $\hat{t}_u$ would first be estimated, and then either the spectrum or the initial estimates of the components and/or properties would be scaled by $1/\hat{t}_u$.

For Principal Components Regression and Constrained Principal Components regression, a more computationally efficient procedure is preferred. The matrix X (or $X_c$ for Constrained PCR) is decomposed as $$X = U \Sigma V^t$$

The pathlengths are then regressed as $$t = V b_t + e \rightarrow \hat{b}_t = V^t t \rightarrow \hat{t} = V \hat{b}_t$$

The matrix T is formed by placing the elements of t on the diagonal, and the component concentrations and/or properties are regressed as $$y = T^{-1} V b + e \rightarrow \hat{b} = (V^t T^{-2} V)^{-1} V^t T^{-1} y$$

For an unknown material with spectrum $x_u$, the pathlength used in collection the spectrum is estimated as $$x_u = U \Sigma v_c \rightarrow \hat{t}_u = v_c^t b_t$$

The component concentrations and/or properties are then estimated as $$y_u = v_c^t b / t_u$$

The alternative to the above method would involve calculating the singular value decomposition of $X_t$ (the spectra scaled to the estimated pathlengths) to build regression models for y. Since the matrices produced by the singular value decomposition of X (or $X_c$) are required for the pathlength estimation, the singular value decomposition of $X_t$ would produce a second set of matrices which would have to be stored and recalled for the estimation of components and/or properties. By conducting only one singular value decomposition, the above method reduces the computer memory, disk storage, input/output requirements and computation time for conducting the calibrations and analyses.

The regression for the pathlength can be conducted using a step-wise or PRESS based method to detect coefficients that are statistically equivalent to zero. A weighted regression may be employed in the development of the regression models for the component concentrations and/or properties in the case where the individual elements if y are of unequal measurement variance, and/or represent the average of differing numbers of individual experimental determinations. A step-wise or PRESS based method can also be employed to conduct these regressions.

4.0 Preferred Method for Calculating the Measurement Process Signal Matrix

The matrix $U_m$ used in calculation of the Constrained Principal Components Regression and the Constrained Partial Least Square Regression is derived from a matrix M which contains examples of the signals arising from the measurement process. The columns of M will generally consist of two types, calculated spectra which are used to simulate certain types of measurement process signals, and experimental spectra collected so as to provide an example of one or more measurement process signals. The calculated spectra could include, but not be limited to, frequency (or wavelength) dependent polynomials which are used to approximate variations in the baseline of the absorption spectra. Such baseline variations can result from variations in the reflection and/or scattering from the front face of the sample or cell, from variations in the response of the spectrometer detector, or from variations in the intensity of the spectrometer source. An example of the experimental spectra which can be used would include, but not be limited to, the spectra of atmospheric water vapor, and/or carbon dioxide. These type of experimental spectra are referred to as correction spectra.

The following is an example of one computational method for arriving at the $U_m$ matrix. If the reference spectra X are collected over a frequency (wavelength) range from $\nu_1$ to $\nu_2$ at interval $\Delta\nu$, then a set of orthogonal polynomials over the spectral range can be constructed using Legendre polynomials $$P_k(\xi) = \frac{1}{2^k k!} \frac{d^k}{d\xi^k} (\xi^2 - 1)^k$$

where $\xi$ is defined as $$\xi = (\nu - \nu_2)/(\nu_1 - \nu_2)$$

The elements $u_{ij}$ of the $U_p$ polynomial vectors are calculated as $$u_{ij} = P_k(\xi)/\sqrt{f} = \frac{1}{2^k k! \sqrt{f}} \frac{d^k}{k\xi^k} (\xi^2 - 1)^k \text{ where}$$

$$\xi = (\nu_1 + (i - 1) \cdot \Delta\nu - \nu_2)/(\nu_1 - \nu_2)$$

where j is equal to k+1 and the $\sqrt{f}$ is required so that the columns of $U_p$ are normalized. The elements of the first column of $U_p$ correspond to $P_0(\xi)$, and are constants of the value of $1/\sqrt{f}$. The second column of $U_p$ depends linearly on frequency, the third has a quadratic dependency of frequency, etc.. The column vectors of $U_p$ form an orthonormal set, i.e.

$$U_p{}^t U_p = I$$

The matrix $U_p$ is of dimension f by p, where p is the number of polynomial terms being used to model background variations, and p−1 is the highest degree of the polynomial.

Z is an f by z matrix containing z experimental spectra representing measurement process signals for which constraints are to be developed. Z may contain multiple examples of measurement process signals, e.g. several spectra of air with varying water vapor and carbon dioxide levels. The matrix Z is first orthogonalized relative to $U_p$.

$$Z' = Z - Z(Z^t U_p{}^t)$$

The singular value decomposition of Z' is then calculated $$Z' = U_z \Sigma_z V_z{}^t$$

If z' is the number of experimental measurement process signals being modeled, then the first z' columns of $U_z$ are then combined with the $U_p$ to form the f by p+z' matrix $U_m$. Note, for example, if z=10 spectra of air with varying levels of water vapor and carbon dioxide where used in Z, then only z'=2 columns of $U_z$ would be used since only two different process signals are being modeled.

5.0 Spectral Ranges

The spectral data used in developing a Constrained Spectral Regression model may include all of the data points (frequencies or wavelengths) between the normal starting and ending points of a spectrometer scan, or it may be limited to subregions of the spectra, so as to exclude portions of the data. For many spectrometer systems, absorbances above a certain nominal value do not scale linearly with pathlength or component concentration. Since the regression models assume linear response, regions where the absorbance exceeds the range of linear spectrometer response will generally be excluded from the data prior to the development of the model. Subregions can also be excluded to exclude measurement process signals that occur in narrow spectral ranges. For example, in the mid-infrared data where sample components are expected to absorb minimally in the 2300-2400 cm$^{-1}$ range, this spectral range may be excluded to avoid the necessity of adding a carbon dioxide spectrum as a correction spectrum.

I claim:

1. A method of estimating unknown property and/or composition data of a sample, comprising:
   (i) collecting respective spectra of n calibration samples, the spectra being quantified at f discrete frequencies (or wavelengths) and forming a matrix X of dimension f by n;
   (ii) producing a correction matrix $U_m$ of dimension f by m comprising m digitised correction spectra at said discrete frequencies f, said correction spectra simulating data arising from the measurement process itself;
   (iii) orthogonalising X with respect to $U_m$ to produce a corrected spectra matrix $X_c$ whose spectra are each orthogonal to all the spectra in $U_m$;
   (iv) collecting c property data, composition data, or property and, composition data for each of the n calibration samples to form a matrix Y of dimension n by c (c>1);
   (v) determining a predictive model correlating the elements of matrix Y to those of matrix $X_c$;
   (vi) measuring the spectrum of the sample under consideration at said f discrete frequencies to form a matrix of dimension f by 1; and
   (vii) estimating the unknown property and/or composition data of the sample under consideration from its measured spectrum using the predictive model.

2. A method as claimed in claim 1, wherein the predictive model is determined in step (v) using a mathematical technique to solve the equation $Y = X_c{}^t P + E$, where $X_c{}^t$ is the transpose of $X_c$, P is a prediction matrix of dimension f by c, and E is a matrix of residual errors from the model and is of dimension n by c and wherein, for determining the vector $y_u$ of dimension 1 by c containing the estimates of the c property and/or composition data for the sample under consideration, the spectrum $x_u$ of the sample under consideration, $x_u$ being of dimension f by 1, is measured and $y_u$ is determined from the relationship $y_u = x_u{}^t P$, $x_u{}^t$ being the transpose of spectrum vector $x_u$.

3. A method as claimed in claim 2 for which f is less than or equal to n, wherein said mathematical technique is linear least squares regression.

4. A method as claimed in claim 2, wherein said mathematical technique is principal components regression.

5. A method as claimed in claim 2, wherein said mathematical technique in partial least squares regression.

6. A method as claimed in claim 1, wherein the spectra collected in step (i) and the spectrum measured in step (vi) are all absorption spectra.

7. A method as claimed in claim 1, wherein the collected spectra of the calibration samples and the measured spectrum of the sample under consideration are in the near-infrared range.

8. A method as claimed in claim 1, wherein the collected spectra of the calibration samples and the measured spectrum of the sample under consideration are in the mid-infrared range.

9. A method as claimed in claim 1, wherein the m spectra forming the columns of matrix $U_m$ are all mutually orthogonal.

10. A method as claimed in claim 1, wherein step (ii) comprises:
   (iia) modelling baseline variations by a set of orthonormal frequency (or wavelength) dependent polynomials which form the columns of a matrix $U_p$ of dimension f by p where p is the order of the polynomials and the columns of $U_p$ are orthonormal polynomials;
   (iib) supplying at least one ex-sample spectrum which is representative of an anticipated spectral interference due to an ex-sample chemical compound, this ex-sample spectrum or these ex-sample spectra forming the column(s) of a matrix $X_s$ of dimension f by s where s ($>1$) is the number of such ex-sample spectra and is greater than or equal to the number of such ex-sample spectral interferences s';
   (iic) orthogonalising the column(s) of $X_s$ with respect to $U_p$ to form a new matrix $X_s'$;
   (iid) orthogonalising the column(s) of $X_s'$ among themselves to form a new matrix $U_s$;
   (iie) combining matrices $U_p$ and $U_s$ to form a matrix $U_m$ whose columns are the columns of $U_p$ and $U_s$ arranged side-by-side.

11. A method according to claim 1, wherein, for determining any significant change in the measurement process data between the times steps (i) and (vi) were performed, the following steps are carried out:
   (a) a matrix $V_m$ of dimension n by m is formed as the dot product $X^t U_m$, where $X^t$ is the transpose of matrix X;
   (b) the corrected data matrix $X_c$ is formed and its singular value decomposition computed as $U\Sigma V^t$, where U is a matrix of dimension f by n and contains the principal component spectra as columns, $\Sigma$ is a diagonal matrix of dimension n by n and contains the singular values, and V is a matrix of dimension n by n and contains the principal component scores, $V^t$ being the transpose of V;
   (c) a regression of the form $V_m = VZ + R$ is determined;
   (d) a vector $v_m$ is formed as the dot product of the measured spectrum of the sample under consideration, $x_u$, with each of the columns of the correction matrix $U_m$, $v_m = x_u^t U_m$;
   (e) a corrected spectrum $x_c$ is formed as a result of orthogonalising $x_u$ with respect to $U_m$, $x_c = x_u - U_m v_m^t$;
   (f) the scores for the corrected spectrum are calculated as $v = x_c^t U \Sigma^{-1}$ where $x_c^t$ is the transpose of $x_c$;
   (g) the measurement process signals are calculated as $r = v_m - vZ$; and
   (h) the magnitude of the elements of r are compared with the range of values of R, whereby a significant difference indicates a significant change in the measurement process data.

12. A method as claimed in claim 1 for which matrix X is to be corrected only for the effect of baseline variations, wherein said baseline variations are modelled by a set of orthogonal frequency (or wavelength) dependent polynomials which form said matrix $U_m$ of dimension f by m where m is the order of the polynomials and the columns of $U_m$ are orthogonal polynomials.

13. A method as claimed in claim 12, wherein said orthogonal polynomials are Legendre polynomials.

14. A method as claimed in claim 1 for which matrix X is to be corrected only for the effect of chemical compounds which do not form part of the sample whose unknown property data, composition data, or property and composition data is to be determined (hereafter "ex-sample chemical compounds"), wherein the spectra that form the columns of $U_m$ are orthogonal vectors that are representatives of those ex-sample chemical compounds.

15. A method as claimed in claim 10, wherein step (ic) is performed by a Gram-Schmidt orthogonalization procedure.

16. A method as claimed in claim 10, wherein the ex-sample spectrum is that of water vapor.

17. A method as claimed in claim 10, wherein the ex-sample spectrum is that of carbon dioxide vapor.

18. A method as claimed in claim 10, where the ex-sample spectra are those of water vapor and carbon dioxide vapor.

19. A method as claimed in claim 10, wherein in step (id), a singular value decomposition of matrix $X_s'$ is used to generate the orthogonal correction spectra Us, the first s' terms of which correspond to the number of different types of ex-sample spectral interferences being modelled are retained while any remaining terms are eliminated, and the resulting matrix $U_s$ is combined with matrix $U_p$ in step (ie) to form matrix $U_m$.

20. Apparatus for estimating unknown property and/or compositional data of a sample, comprising:
   a spectrometer for generating the spectrum of a plurality of calibration samples n having known properties composition, or properties and composition c, and the spectrum of a sample under consideration having unknown property and/or composition data which is to be estimated; and
   computer means arranged to receive the measured spectrum data from the spectrometer and operable
      (i) in a data correction mode to perform, in conjunction with an operator, steps (i) to (iii) of claim 1;
      (ii) in a storing mode to store the c property data, composition data or property and composition data for each of the n calibration samples to form the matrix Y of dimension n by c ($c \geq 1$);
      (iii) in a model building mode to determine, in conjunction with the operator, a predictive model according to step (v) of claim 1;
      (iv) in a measurement mode to perform step (vi) of claim 12; and
      (v) in a prediction mode to perform step (vii) of claim 12, in order to estimate the unknown property data, composition data, or property and composition data of the sample under consideration according to the determined predictive model correlating the elements of matrix Y to the corrected spectra matrix $X_c$ resulting from the orthogonalization of matrix X with respect to the correction matrix $U_m$.

* * * * *